United States Patent
Trumpp et al.

(10) Patent No.: US 10,669,588 B2
(45) Date of Patent: Jun. 2, 2020

(54) METHODS FOR SUB-TYPING AND TREATING CANCER

(71) Applicant: HI-STEM GGMBH im Deutschen, Heidelberg (DE)

(72) Inventors: Andreas Trumpp, Heidelberg (DE); Martin Ronald Sprick, Heidelberg (DE); Elisa Noll, Heidelberg (DE)

(73) Assignee: HI-STEM GGMBH, Heidelberg (DE)

( * ) Notice: Subject to any disclaimer, the term of this patent is extended or adjusted under 35 U.S.C. 154(b) by 98 days.

(21) Appl. No.: 15/514,812

(22) PCT Filed: Sep. 28, 2015

(86) PCT No.: PCT/EP2015/001916
§ 371 (c)(1),
(2) Date: Mar. 27, 2017

(87) PCT Pub. No.: WO2016/045799
PCT Pub. Date: Mar. 31, 2016

(65) Prior Publication Data
US 2017/0260593 A1 Sep. 14, 2017

(30) Foreign Application Priority Data

Sep. 26, 2014 (EP) .................................... 14003353
Apr. 10, 2015 (EP) .................................... 15001024

(51) Int. Cl.
| | | |
|---|---|---|
| *C12N 15/11* | (2006.01) | |
| *C12Q 1/6886* | (2018.01) | |
| *A61K 31/517* | (2006.01) | |
| *A61K 45/06* | (2006.01) | |
| *C12N 15/113* | (2010.01) | |

(52) U.S. Cl.
CPC .......... *C12Q 1/6886* (2013.01); *A61K 31/517* (2013.01); *A61K 45/06* (2013.01); *C12N 15/1137* (2013.01); *C12N 2310/14* (2013.01); *C12N 2310/531* (2013.01); *C12Q 2600/106* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

2012/0329841 A1* 12/2012 Potter .................. A61K 31/164
514/365

FOREIGN PATENT DOCUMENTS

| EP | 1549771 A2 | 6/2005 | |
|---|---|---|---|
| WO | WO2003013534 A3 * | 2/2003 | ......... A61K 31/4745 |
| WO | 2003057916 A2 | 7/2003 | |
| WO | 2004031412 A2 | 4/2004 | |
| WO | 2014056627 A1 | 4/2014 | |

OTHER PUBLICATIONS

Jiang et al, CYP3A5 Functions as a Tumor Suppressor in Hepatocellular Carcinoma by Regulating mTORC2/Akt Signaling, Apr. 2015, Cancer Res; 75(7): 1470-1481 (Year: 2015).*
Lohr et al, Cationic liposomal paclitaxel plus gemcitabine or genncitabine alone in patients with advanced pancreatic cancer: a randomized controlled phase II trial, Annals of Oncology 23: 1214-1222 (Year: 2012).*
Santos et al, Metabolism of Irinotecan (CPT-11) by CYP3A4 and CYP3A5 in Humans, 2000, Clinical Cancer Research, 6: 2012-2020 (Year: 2000).*
Castell et al., "Metabolism and bioactivation of toxicants in the lung. The in vitro cellular approach", Exp Toxicol Pathol., 2005, 57 Suppl 1:189-204.
Downie et al., "Profiling cytochrome P450 expression in ovarian cancer: identification of prognostic markers", Clin Cancer Res., 2005, 11(20):7369-75.
Kivistoe et al., "Expression of cytochrome P 450 3A enzymes in human lung: a combined RT-PCR and Immunohistochemical analysis of normal tissue and lung tumours", Naunyn Schmiedebergs Arch Pharmacol., 1996, 353(2):207-12.
Leclerc et al., "Profiling gene expression of whole cytochrome P450 superfamily in human bronchial and peripheral lung tissues: Differential expression in non-small cell lung cancers", Biochimie., 2010, 92(3):292-306. doi: 10.1016/j.biochi.2009.12.007.
Li et al., "Differential metabolism of gefitinib and erlotinib by human cytochrome P450 enzymes", Clin Cancer Res., 2007, 13(12):3731-7.
Maguire et al., "Regulation of CYP3A4 and CYP3A5 expression and modulation of "intracrine" metabolism of androgens in prostate cells by liganded vitamin D receptor", Mol Cell Endocrinol., 2012, 364(1-2):54-64. doi: 10.1016/j.mce.2012.08.007.
Yu et al., "Pharmacogenomic modeling of circulating tumor and invasive cells for prediction of chemotherapy response and resistance in pancreatic cancer", Clin Cancer Res., 2014, 20(20):5281-9. doi: 10.1158/1078-0432.CCR-14-0531.
International Search Report issued in PCT/EP2015/001916, dated Dec. 7, 2015, Applicant HI-STEM GGMBH (6 pages).
Written Opinion issued in PCT/EP2015/001916, dated Dec. 7, 2015, Applicant HI-STEM GGMBH (7 pages).
International Preliminary Report on Patentability issued in PCT/EP2015/001916, dated Mar. 28, 2017 (8 pages).

* cited by examiner

Primary Examiner — Ekaterina Poliakova-Georgantas
(74) Attorney, Agent, or Firm — Prismatic Law Group, PLLC

(57) ABSTRACT

This invention relates to a novel approach for the identification and stratification of subtypes of cancer, particularly pancreatic ductal adenocarcinoma (PDAC). The invention furthermore relates to a novel approach with respect to the treatment of cancer, particularly pancreatic ductal adenocarcinoma (PDAC).

17 Claims, 55 Drawing Sheets
Specification includes a Sequence Listing.

Figure 1:
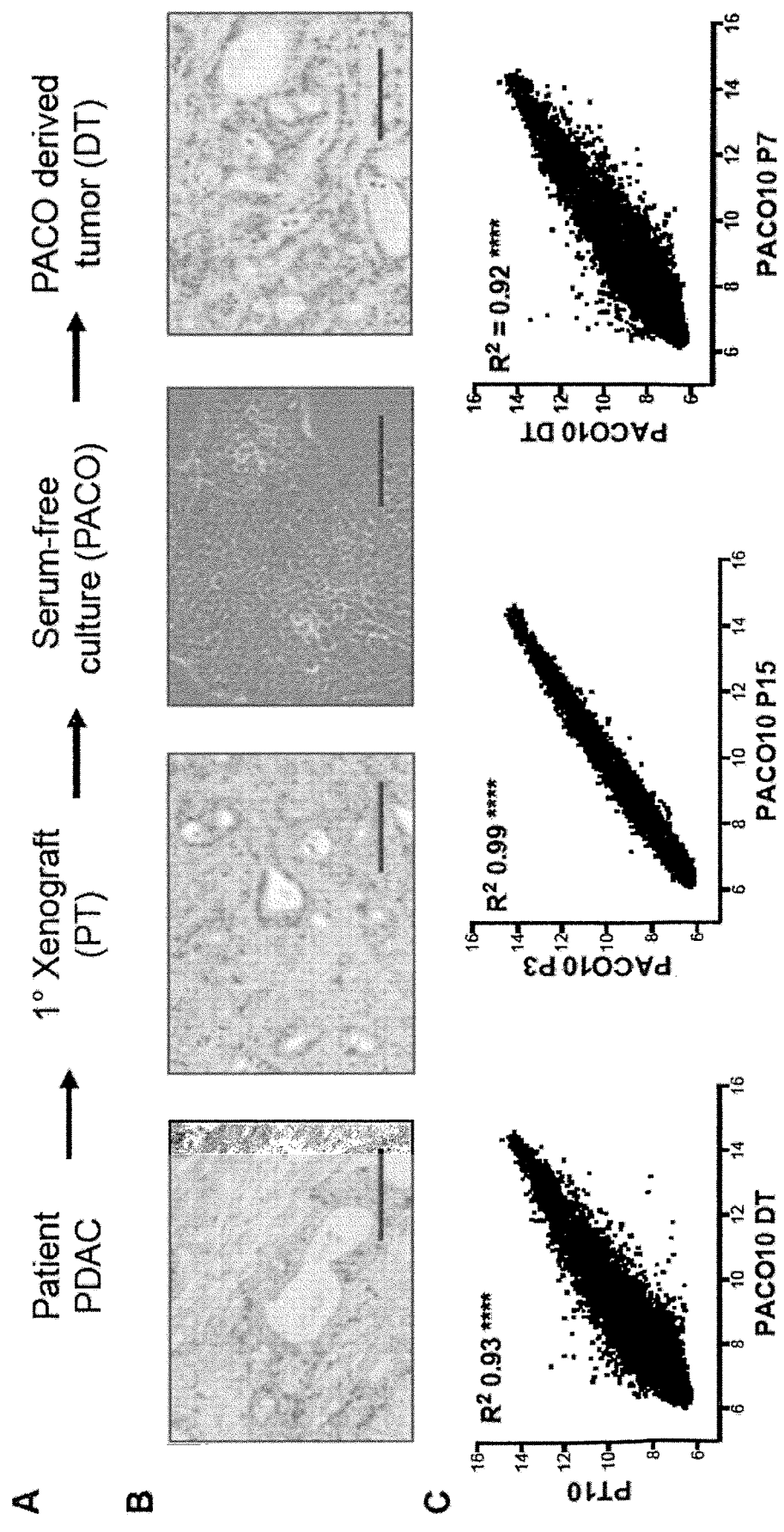
Figure 2:
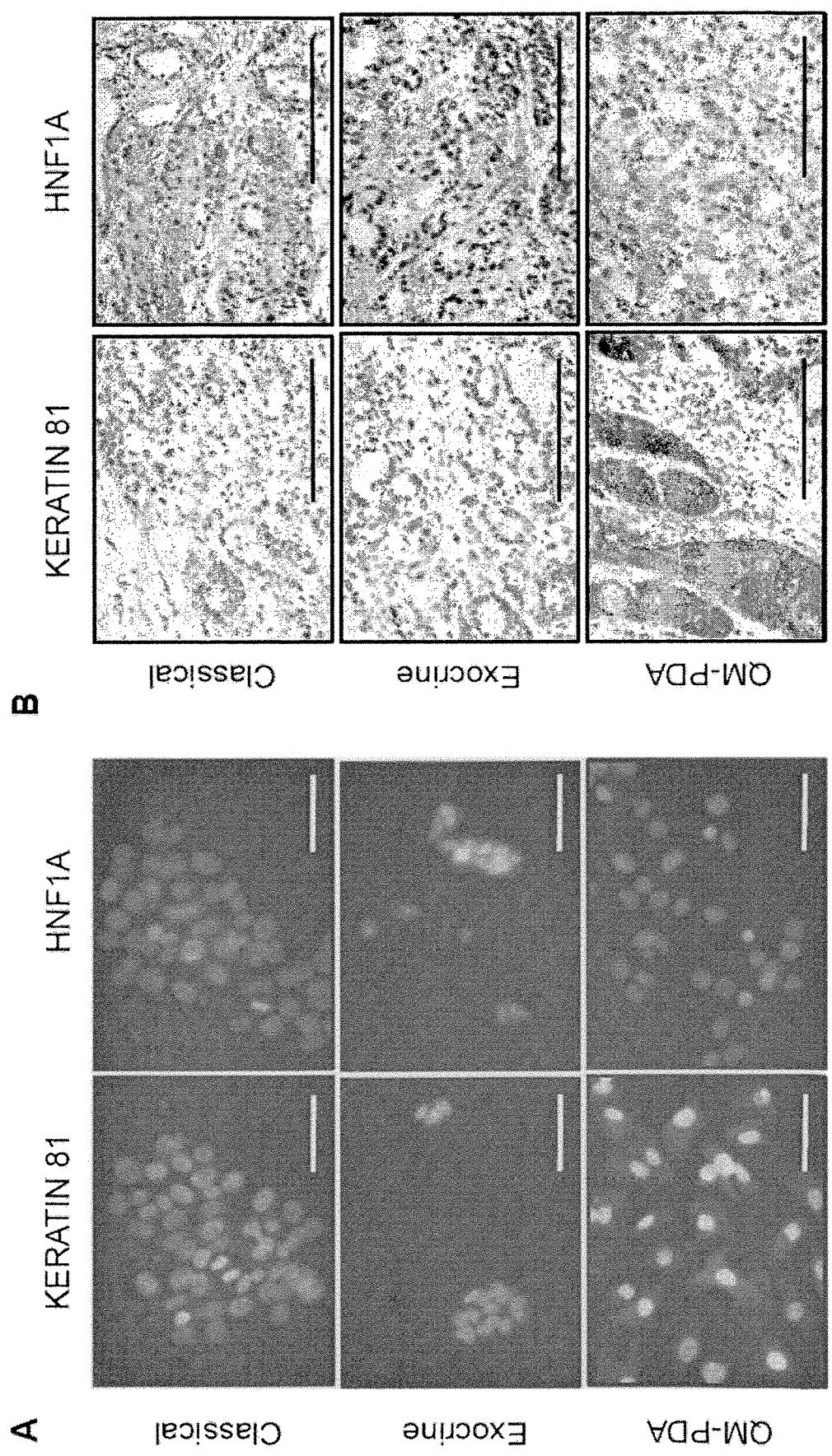

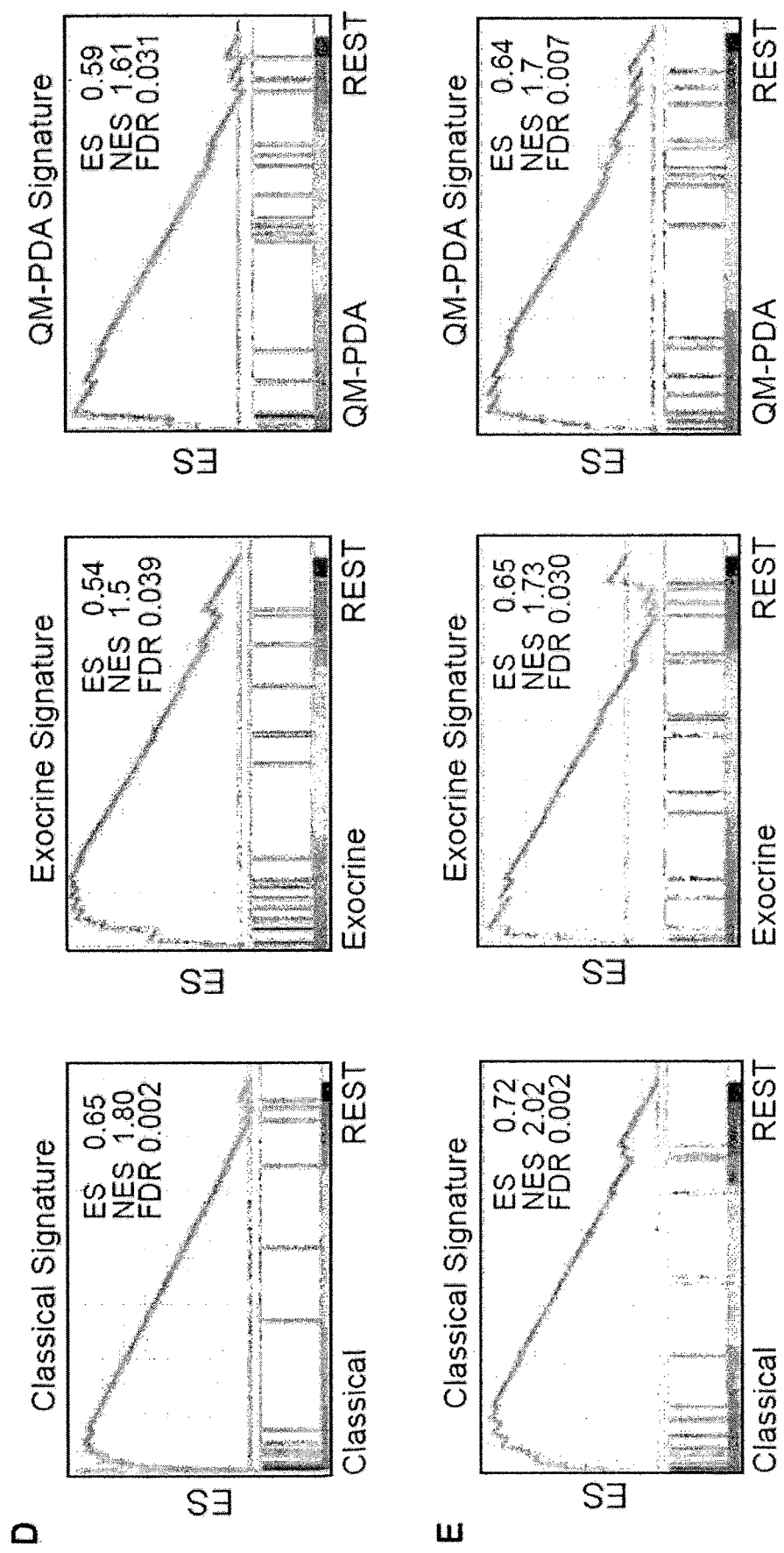
Figure 1 (contd.):

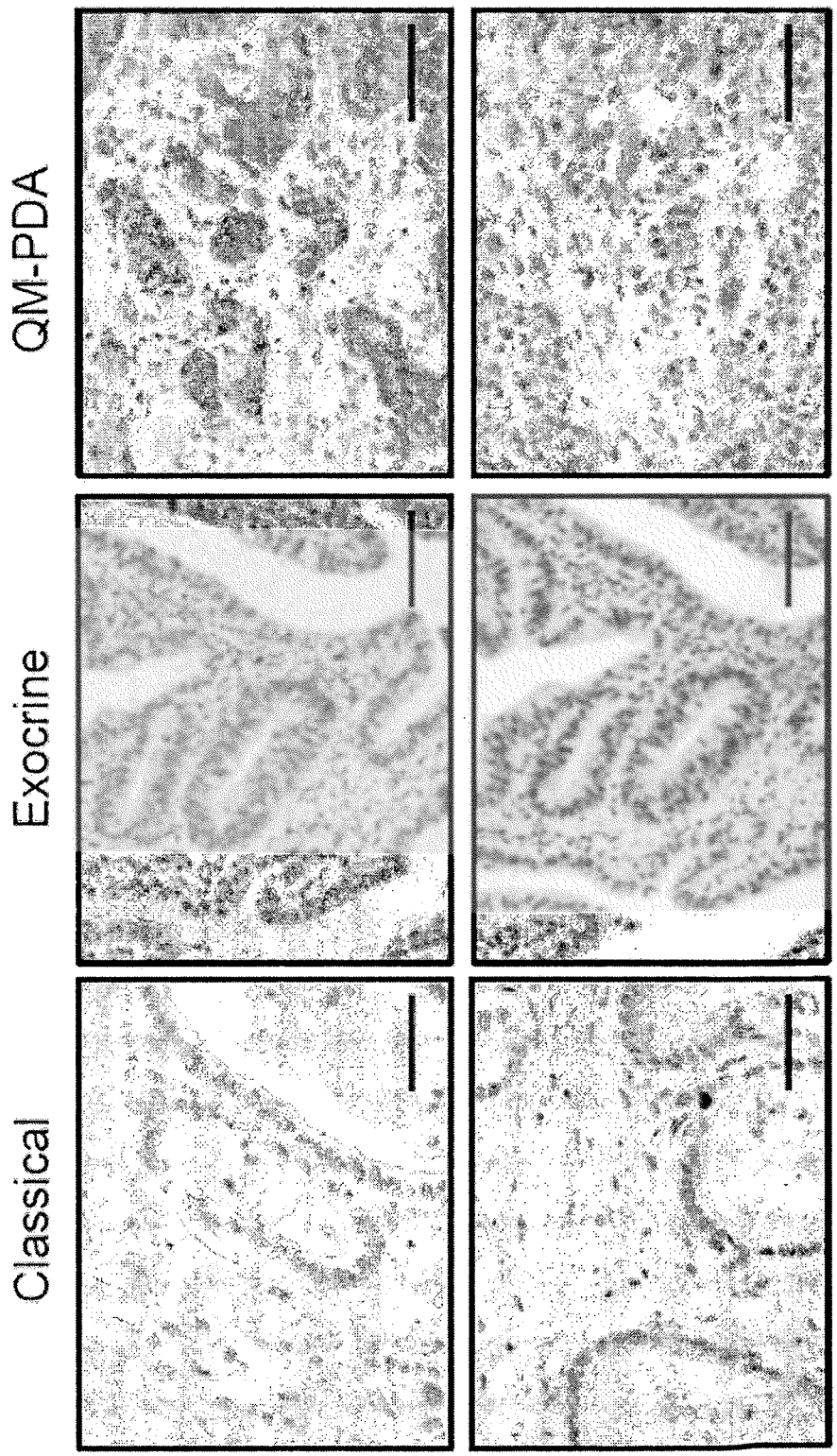
Figure 2 (contd.)

Figure 2 (contd.):
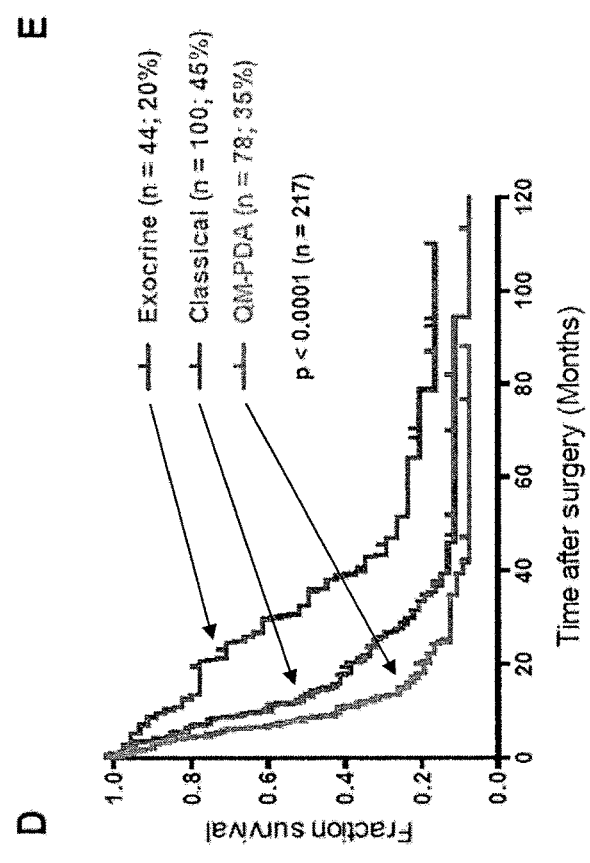

Figure 3:
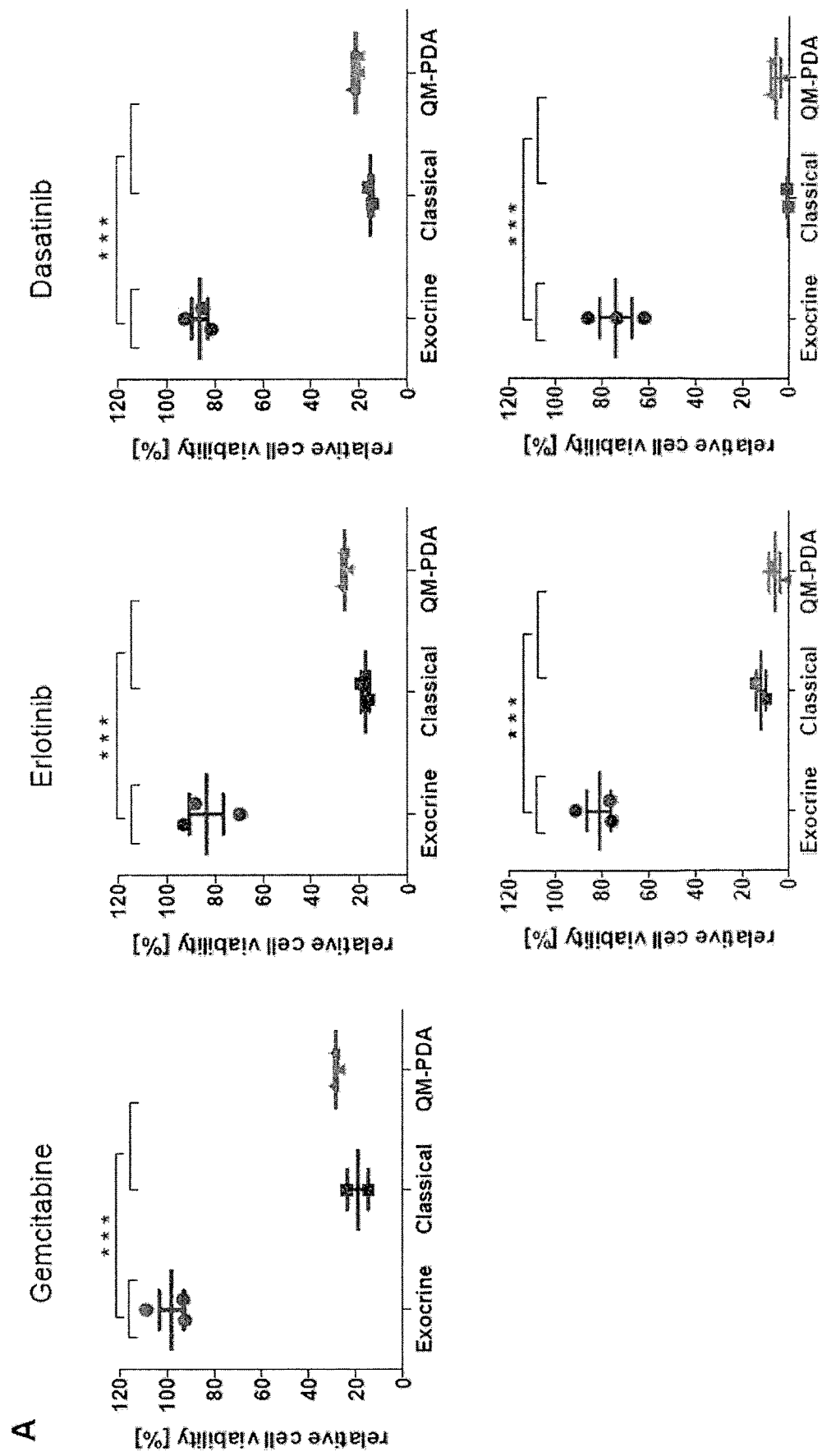

Figure 3 (contd.):
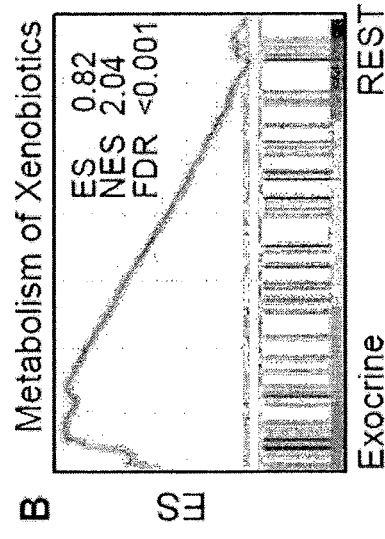
C
| PACO cells: *Exocrine vs. Rest* | NES | FDR |
|---|---|---|
| KEGG_Metabolism of Xenobiotics by Cytochrome P450 | 2.04 | <0.001 |
| KEGG_Drug Metabolism Cytochrome P450 | 1.99 | <0.001 |
| Reactome_Biological Oxidation | 1.93 | 0.010 |
| Reactome_Xenobiotics | 1.72 | 0.044 |
| Reactome_Cyotchrome P450 Arranged by Substrate | 1.74 | 0.041 |

Figure 3 (contd.):
E
| PT + DT: Exocrine vs. Rest | NES | FDR |
|---|---|---|
| Reactome_Biological Oxidation | 1.83 | 0.010 |
| Reactome_Xenobiotics | 1.79 | 0.029 |
| Reactome_Cyotchrome P450 Arranged by Substrate | 1.65 | 0.046 |
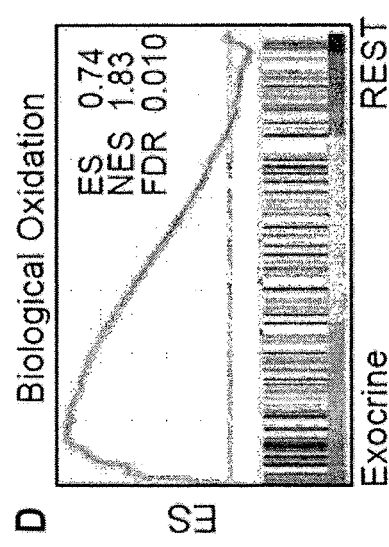
D Biological Oxidation
ES 0.74
NES 1.83
FDR 0.010

Figure 4:
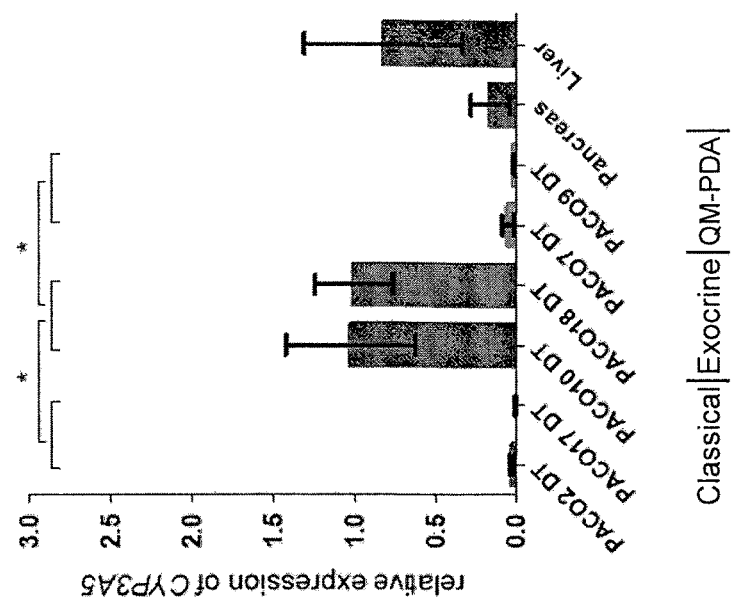
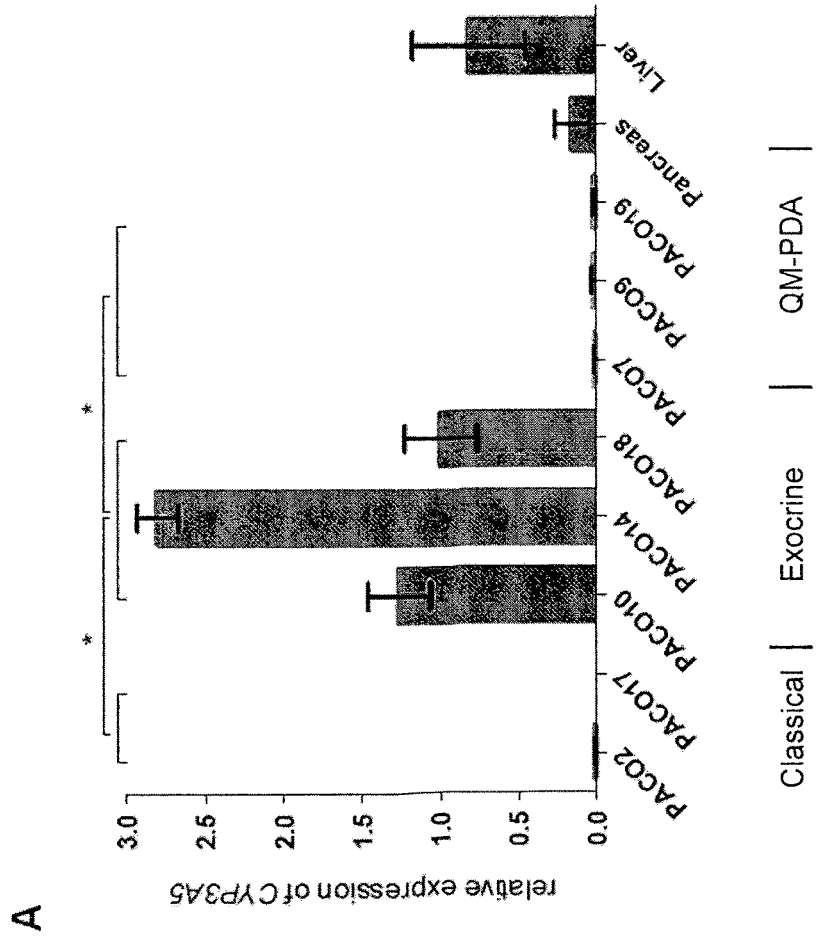

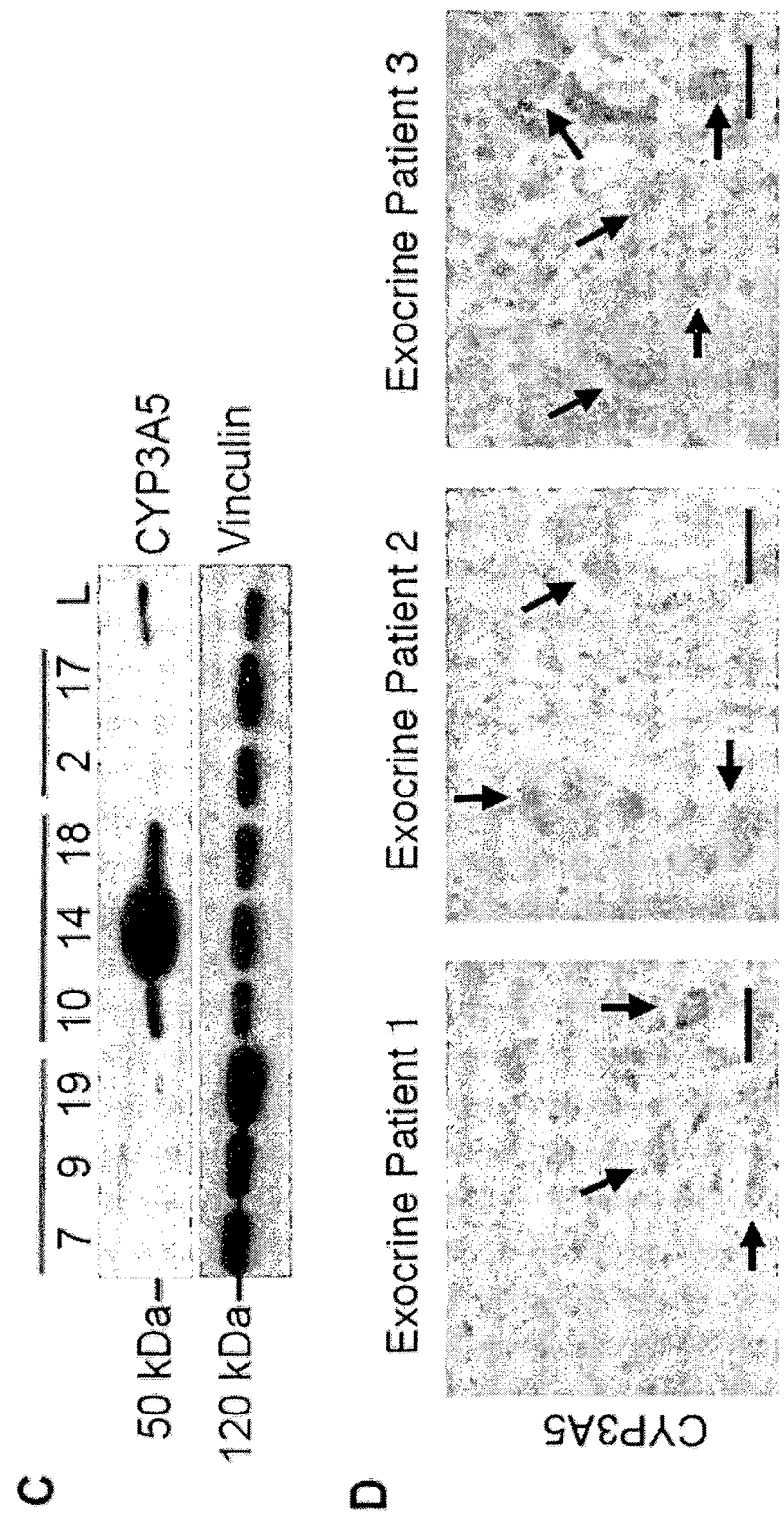

Figure 4 (contd.):
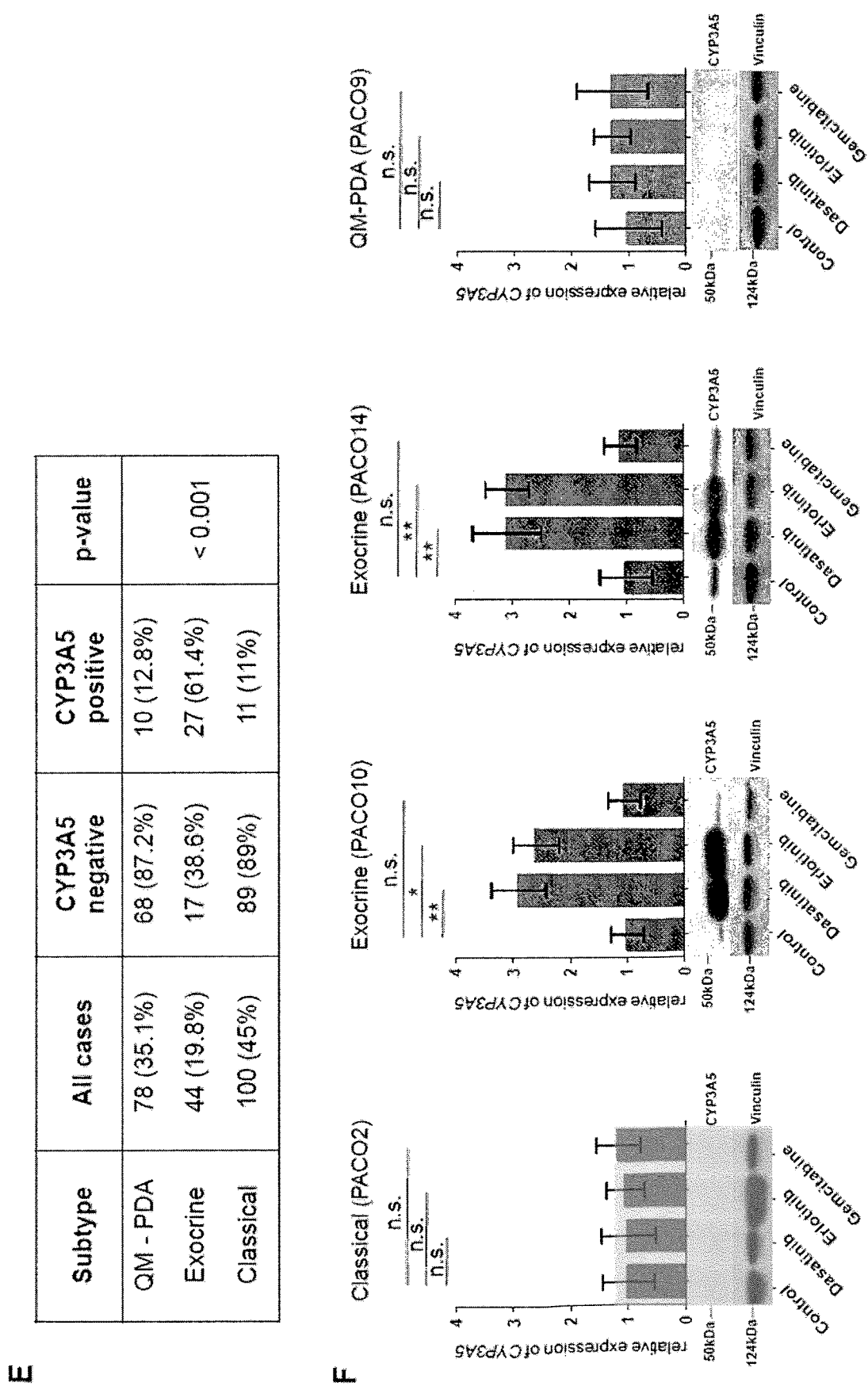

Figure 5:
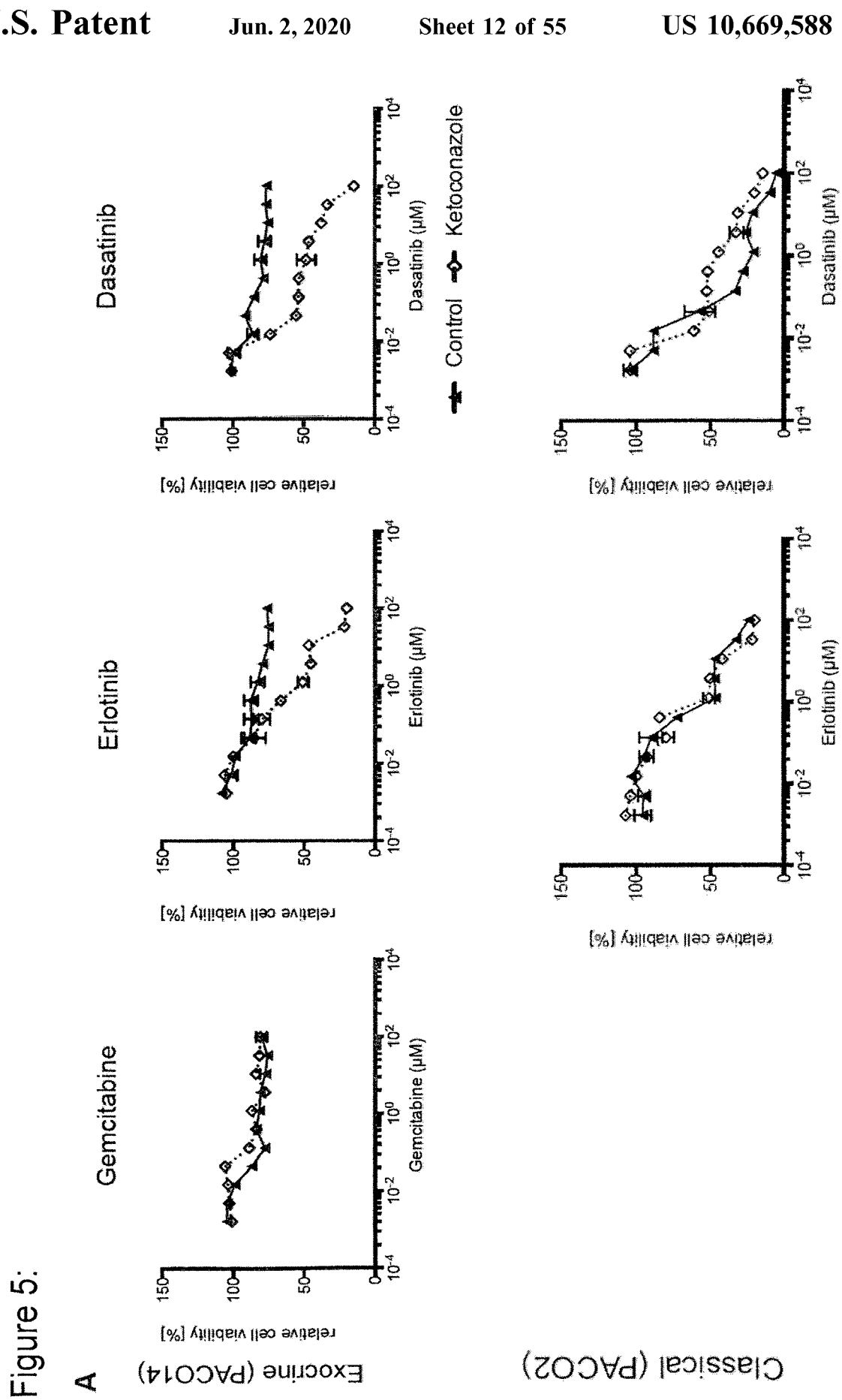

Figure 5 (contd.):
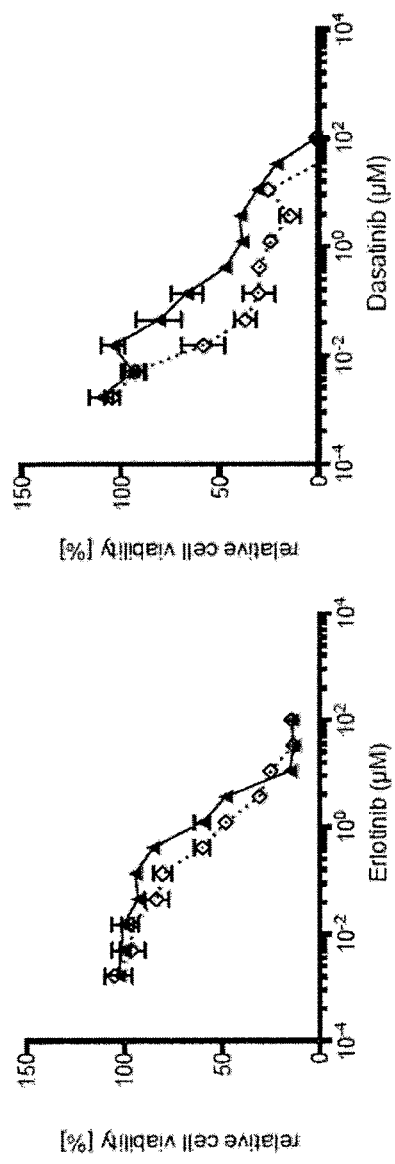
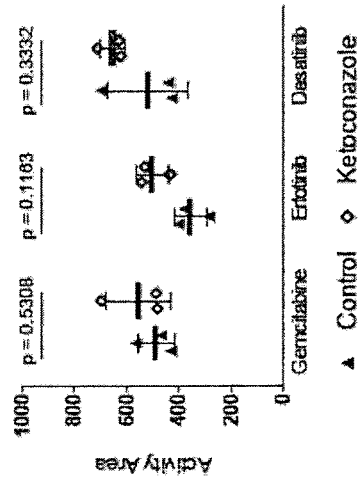
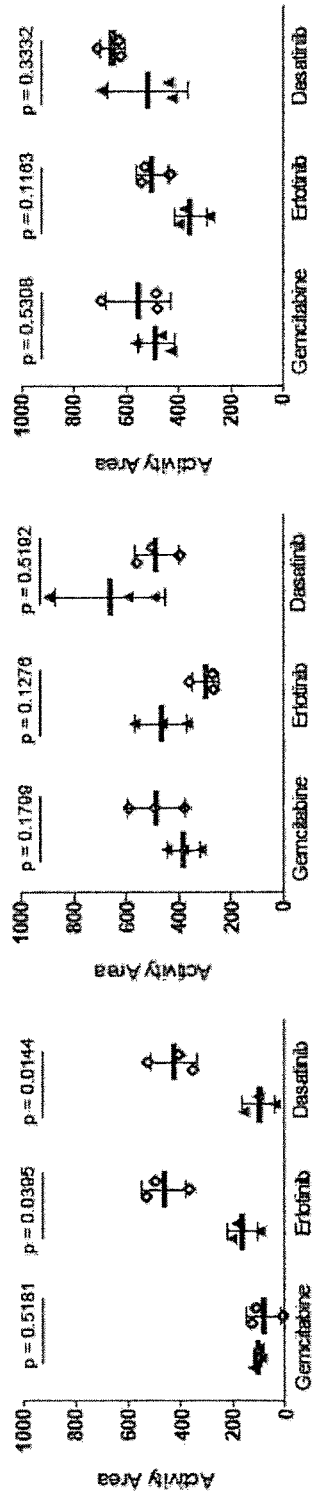

Figure 6:
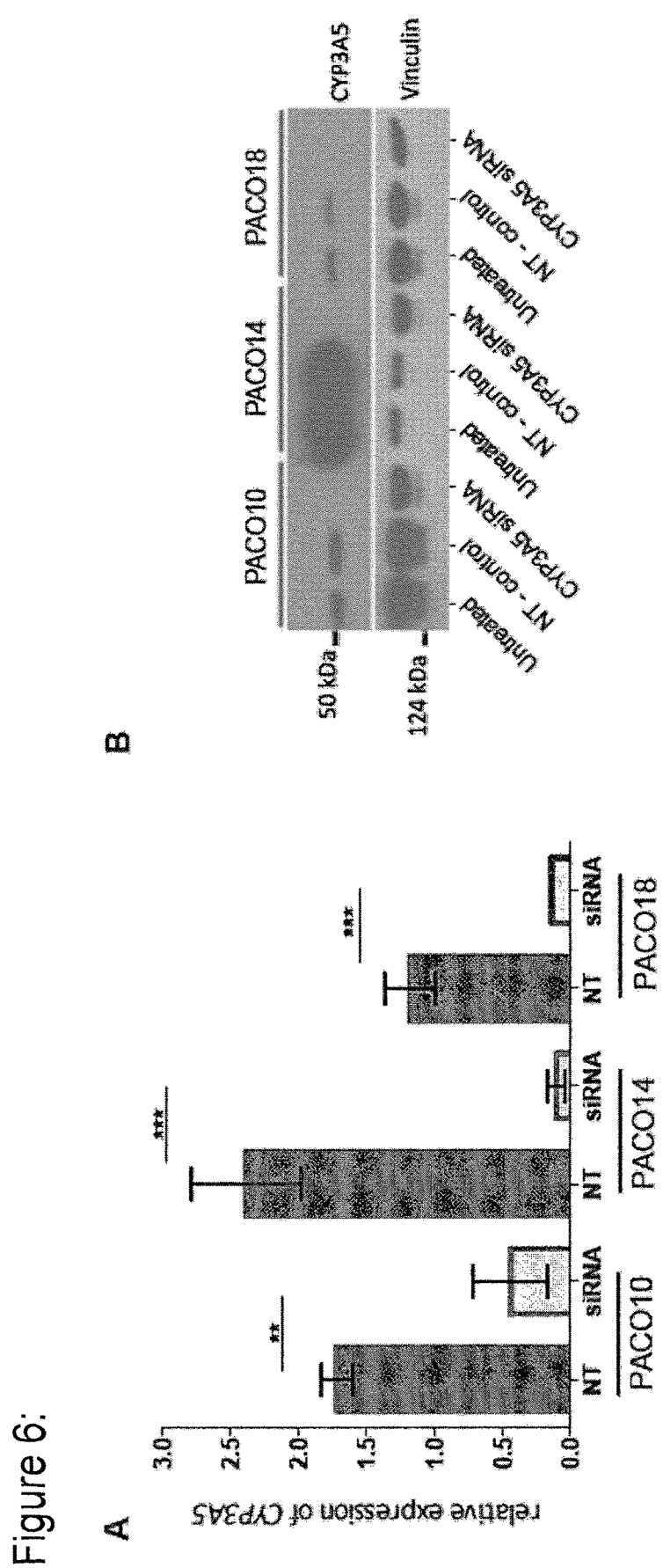
Figure 7:
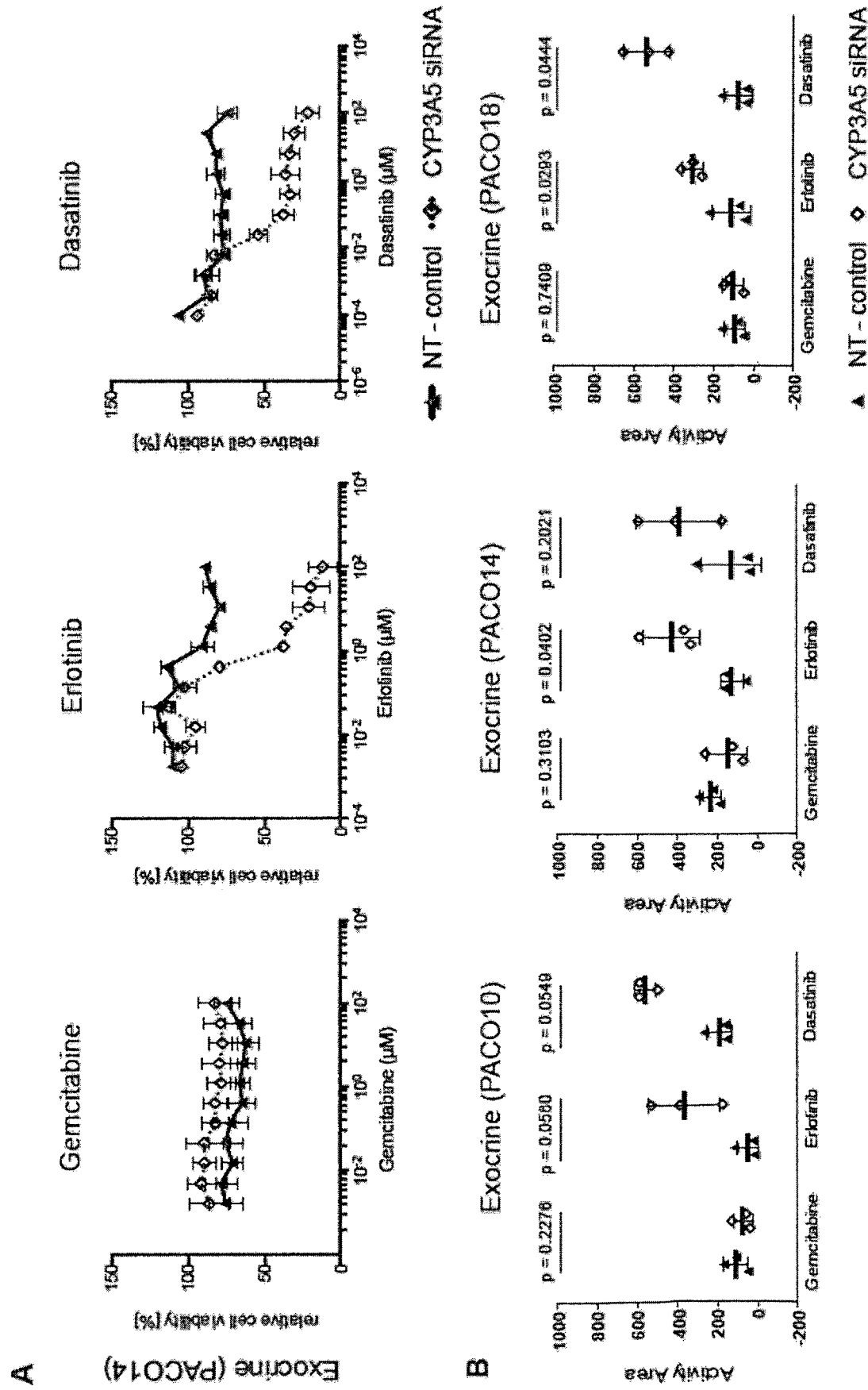

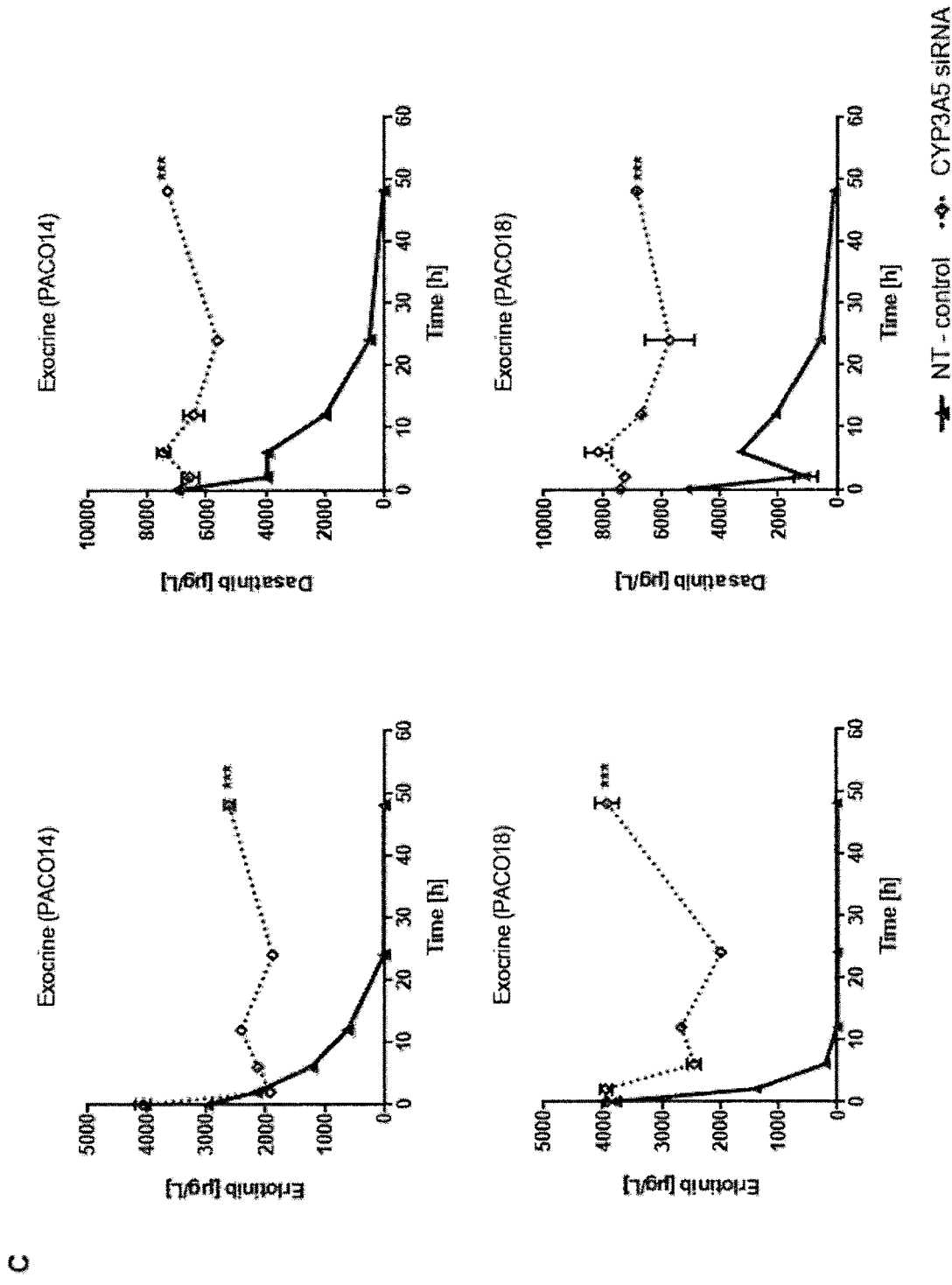
Figure 6 (contd.):

Figure 7 (contd.):
C
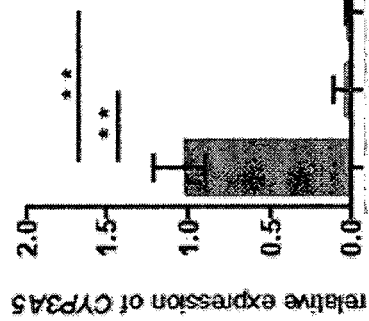
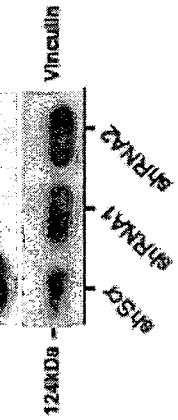
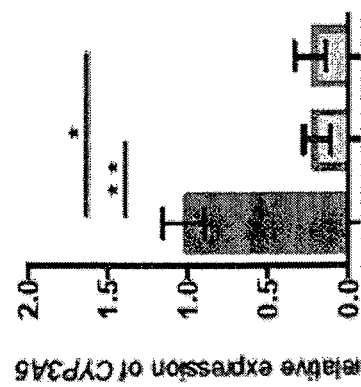
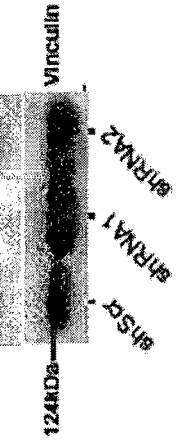
D
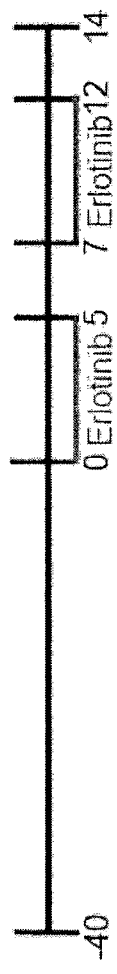

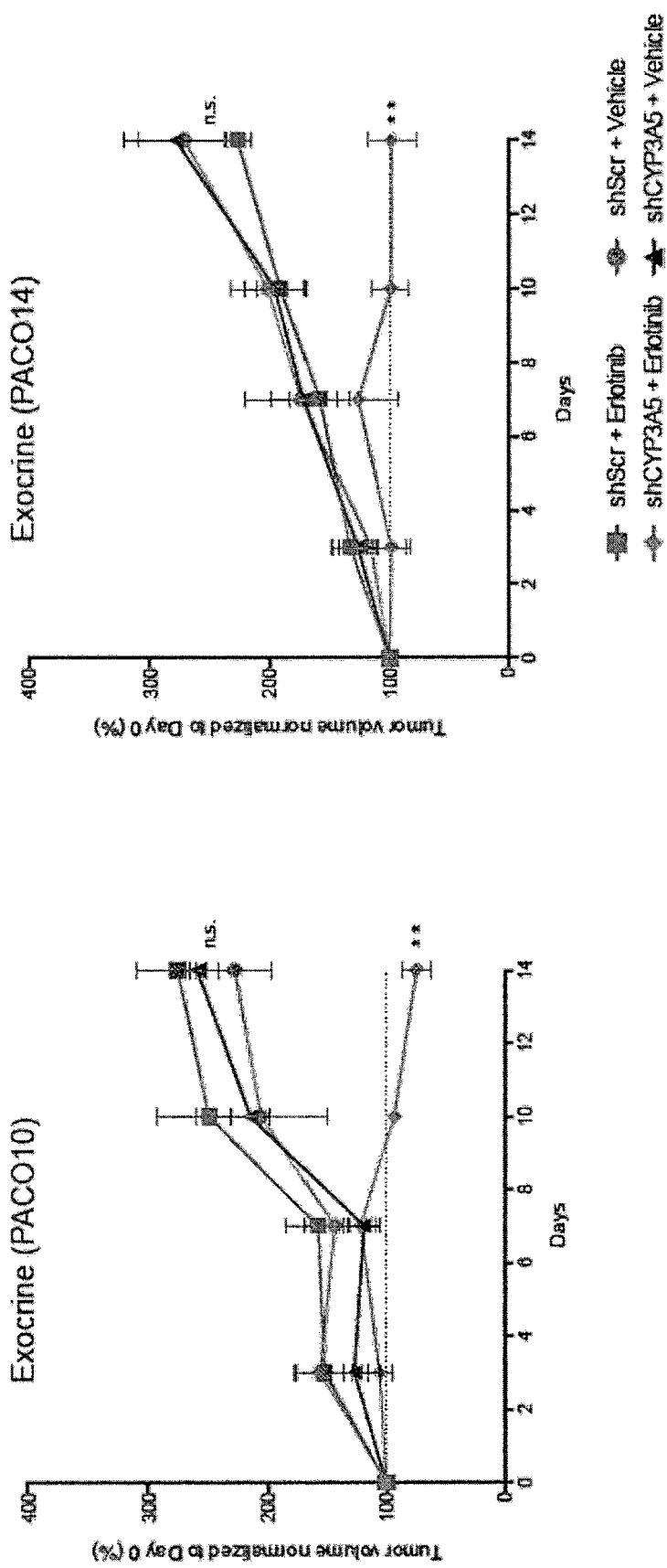
Figure 7 (contd.):

Figure 7 (contd.):
F
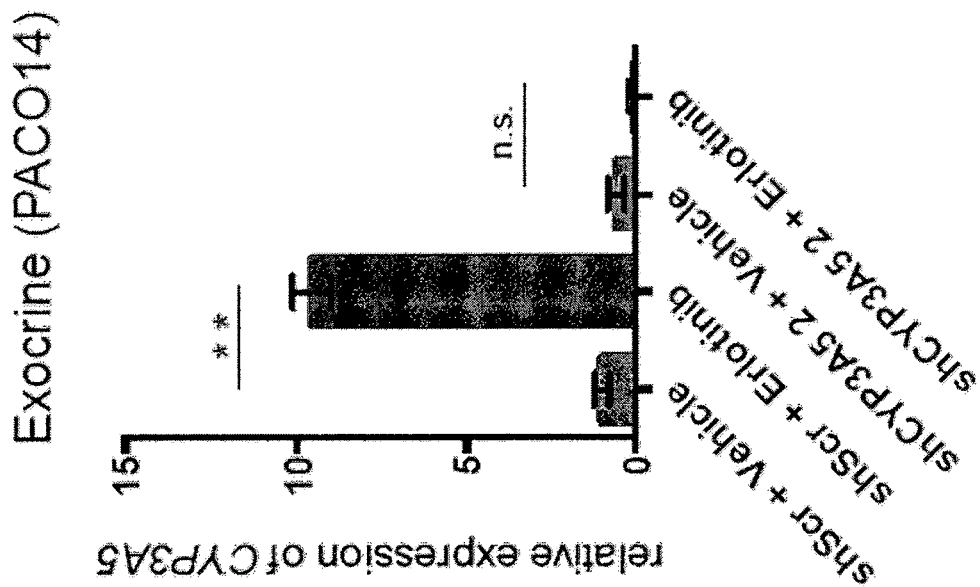
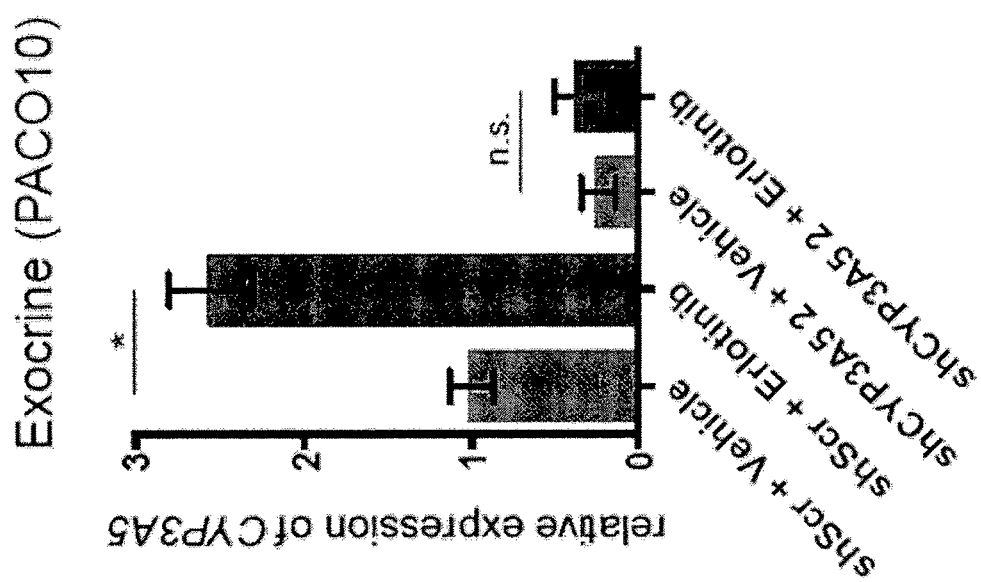

Figure 8 (contd.):

B

| Cell Line ID | Primary Tumor ID | Age | Sex | Stage (TMN) | Grade | Pathological Diagnosis |
|---|---|---|---|---|---|---|
| PACO2 | PT2 | 60 | Female | T3 N1 M1 | G2 | PDAC |
| PACO7 | PT7 | 45 | Male | T3 N1 Mx | G3 | PDAC |
| PACO9 | PT9 | 52 | Male | T3 N1 M0 | G3 | PDAC |
| PACO10 | PT10 | 61 | Male | T3 N1 Mx | G3 | PDAC |
| PACO14 | PT14 | 62 | Female | T3 N1 M0 | G3 | PDAC |
| PACO17 | PT17 | 65 | Male | T3 N1 Mx | G3 | PDAC |
| PACO18 | PT18 | 62 | Male | T3 N1 M0 | G3 | PDAC |
| PACO19 | PT19 | 48 | Male | T3 N1 M0 | G3 | PDAC |

Figure 8 (contd.):

C

| Samples | $R^2$ | p-value |
|---|---|---|
| PT14 vs. PACO14 DT | 0.93 | <0.0001 |
| PT2 vs. PACO2 DT | 0.95 | <0.0001 |
| PT9 vs. PACO9 DT | 0.90 | <0.0001 |
| PACO14 P4 vs. PACO14 P9 | 0.97 | <0.0001 |
| PACO2 P3 vs. PACO2 P10 | 0.96 | <0.0001 |
| PACO9 P4 vs. PACO9 P11 | 0.97 | <0.0001 |
| PACO14 DT vs. PACO14 P10 | 0.93 | <0.001 |
| PACO2 DT vs. PACO2 P8 | 0.91 | <0.001 |
| PACO9 DT vs. PACO9 P7 | 0.87 | <0.001 |

Figure 9:
A

| Markers | Company (Order #) | Designated for subtype | QM-PDA | Classical | Exocrine | Note |
|---|---|---|---|---|---|---|
| CEACAM3 | Sigma (HPA011041) | Classical | - | - | - | Ab did not stain in our hands |
| CEACAM6 | Dako (A0115) | Classical | +/- | - | + | Diffuse staining in few cells |
| S100P | Dako (Z0311) | Classical | - | - | - | Ab did not stain in our hands |
| S100A1 | Assay Biotech (C0318) | Classical | +/- | ++ | +/- | Ab gave a nuclear staining only in the classical subtype |
| TFF3 | SDIX (2994.00.02) | Classical | + | - | - | In patient tumors Ab did not stain exclusively |
| SLC2A3 | Sigma (HPA006539) | QM-PDA | - | - | - | Ab did not stain in our hands |
| AIM2 | Sigma (HPA031365) | QM-PDA | +/- | - | - | diffuse staining in PACO8 DT, rest did not stain |
| SMAD4 | Sigma (HPA019154) | QM-PDA | +/- | +/- | +/- | Ab stained isolated ductal structures in all tumors testes |

Figure 9 (contd.):

A (contd.):

| | | | | |
|---|---|---|---|---|
| VIM | Dako (M7020) | QM-PDA | ++ | | Ab did neither stain classical nor exocrine tumors |
| KRT81 | Santa Cruz (sc-100929) | QM-PDA | ++ | | Ab did neither stain classical nor exocrine tumors |
| CFTR | Abcam (ab2784) | Exocrine | - | | Ab did not stain in our hands |
| SLC4A4 | Millipore (AB3212) | Exocrine | - | | Ab did not stain in our hands |
| REG1A | R&D Systems (431202) | Exocrine | + | | Weak, cytoplasmatic staining |
| CEL3A | Abcam (ab56564) | Exocrine | - | | Ab did not stain in our hands |
| SPINK1 | Sigma (HPA027498) | Exocrine | ++ | ++ | Ab gave a strong cytoplasmic staining in all tumors |
| HNF1 | Santa Cruz (sc-8986) | Exocrine | - | +/- | Ab stained isolated ducts in classical tumors |

++ strong staining; + weak staining; +/- unspecific staining; - no staining

Figure 9 (contd.):

B

| Cell Line ID | Primary Tumor ID | Secondary Tumor ID | KRT81 | HNF1A | CYP3A5 | Subtype |
|---|---|---|---|---|---|---|
| PACO2 | PT2 | DT2 | - | - | - | Classical |
| PACO7 | PT7 | DT7 | + | - | - | QM-PDA |
| PACO9 | PT9 | DT9 | + | - | - | QM-PDA |
| PACO10 | PT10 | DT10 | - | + | + | Exocrine |
| PACO14 | PT14 | DT14 | - | + | + | Exocrine |
| PACO17 | PT17 | DT17 | - | - | - | Classical |
| PACO18 | PT18 | DT18 | - | + | + | Exocrine |
| PACO19 | PT19 | DT19 | + | - | - | QM-PDA |

Figure 9 (contd.):

C

| | | Cases | Events | Mean survival (months) | Standard error | Log-rank-test (p-value) |
|---|---|---|---|---|---|---|
| Age at diagnosis | ≤65 years | 119 | 92 | 42.5 | 6.4 | 0.024 |
| | >65 years | 112 | 97 | 20.3 | 2.3 | |
| Tumor stage | pT1/pT2 | 44 | 35 | 30.8 | 4.9 | 0.124 |
| | pT3/pT4 | 187 | 154 | 28.9 | 4.1 | |
| Nodal status | pN0 | 61 | 42 | 38.4 | 5.7 | 0.003 |
| | pN1 | 170 | 147 | 25.7 | 3.5 | |
| Grade | G1/G2 | 134 | 107 | 28.9 | 3.1 | 0.082 |
| | G3 | 97 | 82 | 25.8 | 5.3 | |
| Subtype | QM | 73 | 64 | 17 | 2.8 | <0.001 |
| | exocrine | 40 | 30 | 43.5 | 5.9 | |
| | classic | 90 | 71 | 32.4 | 6.5 | |
| CYP3A5 | negative | 183 | 149 | 31.7 | 4.5 | 0.046 |
| | positive | 48 | 40 | 32.1 | 4.5 | |

Figure 10:
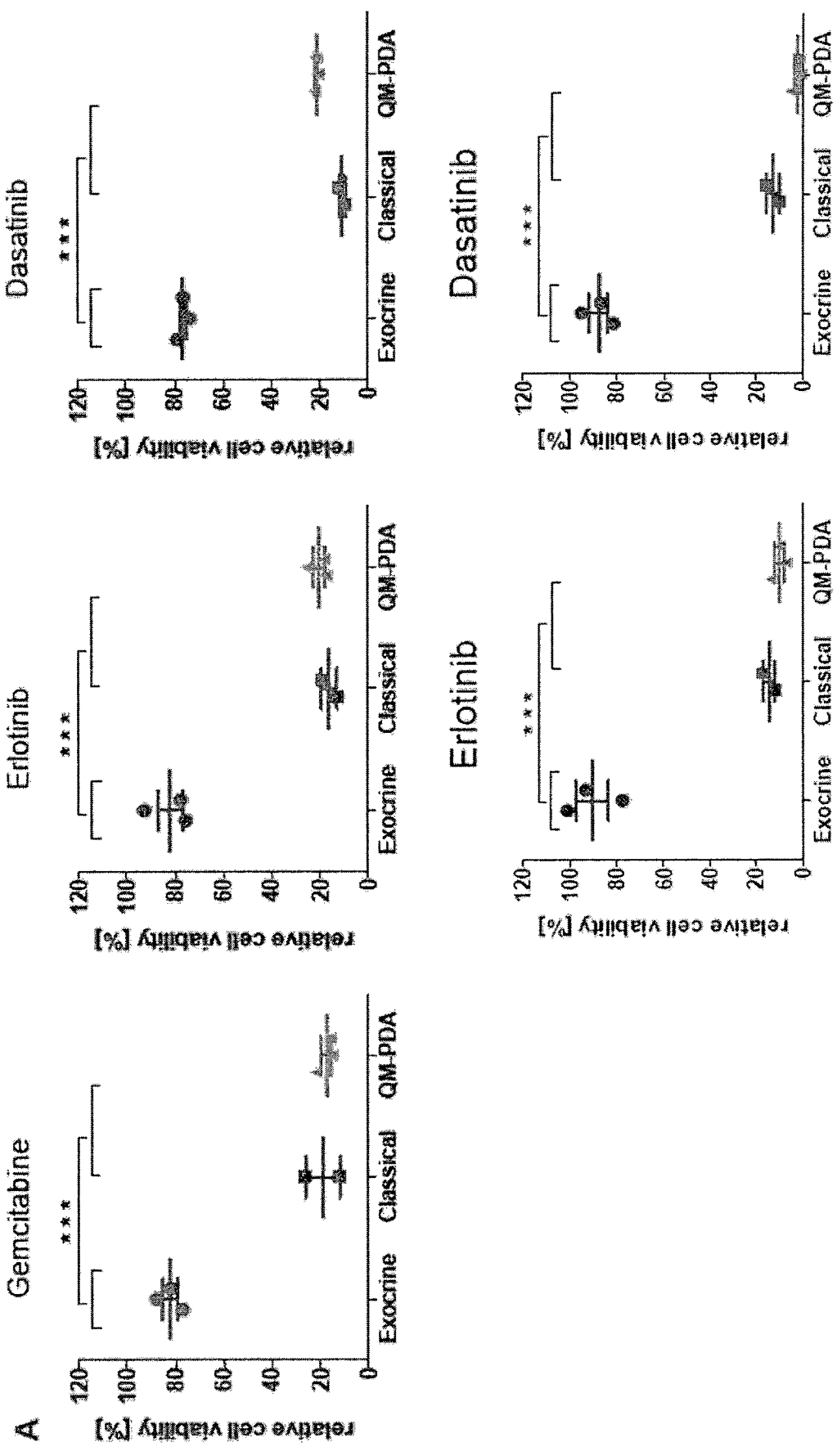

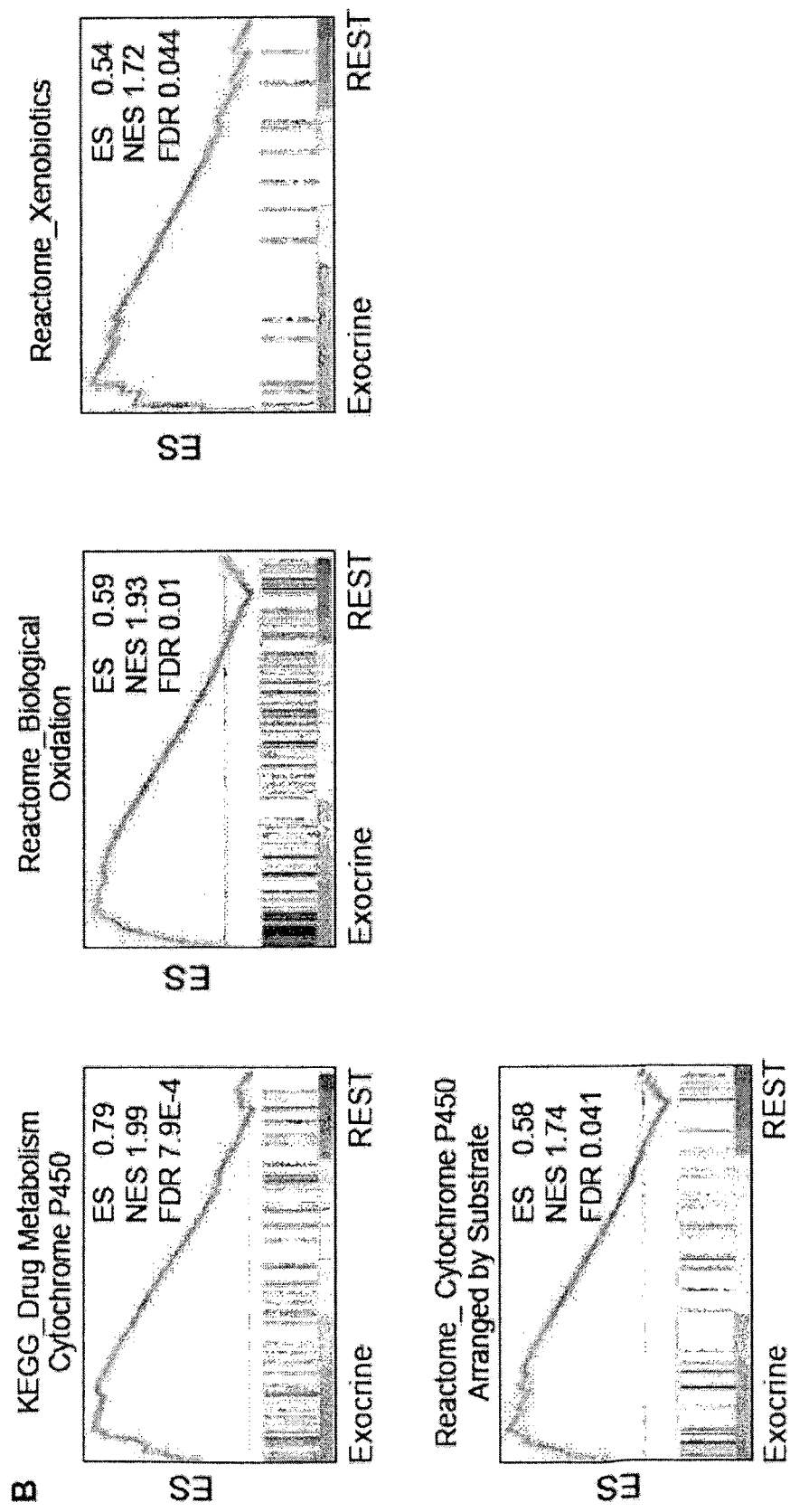
Figure 10 (contd.)

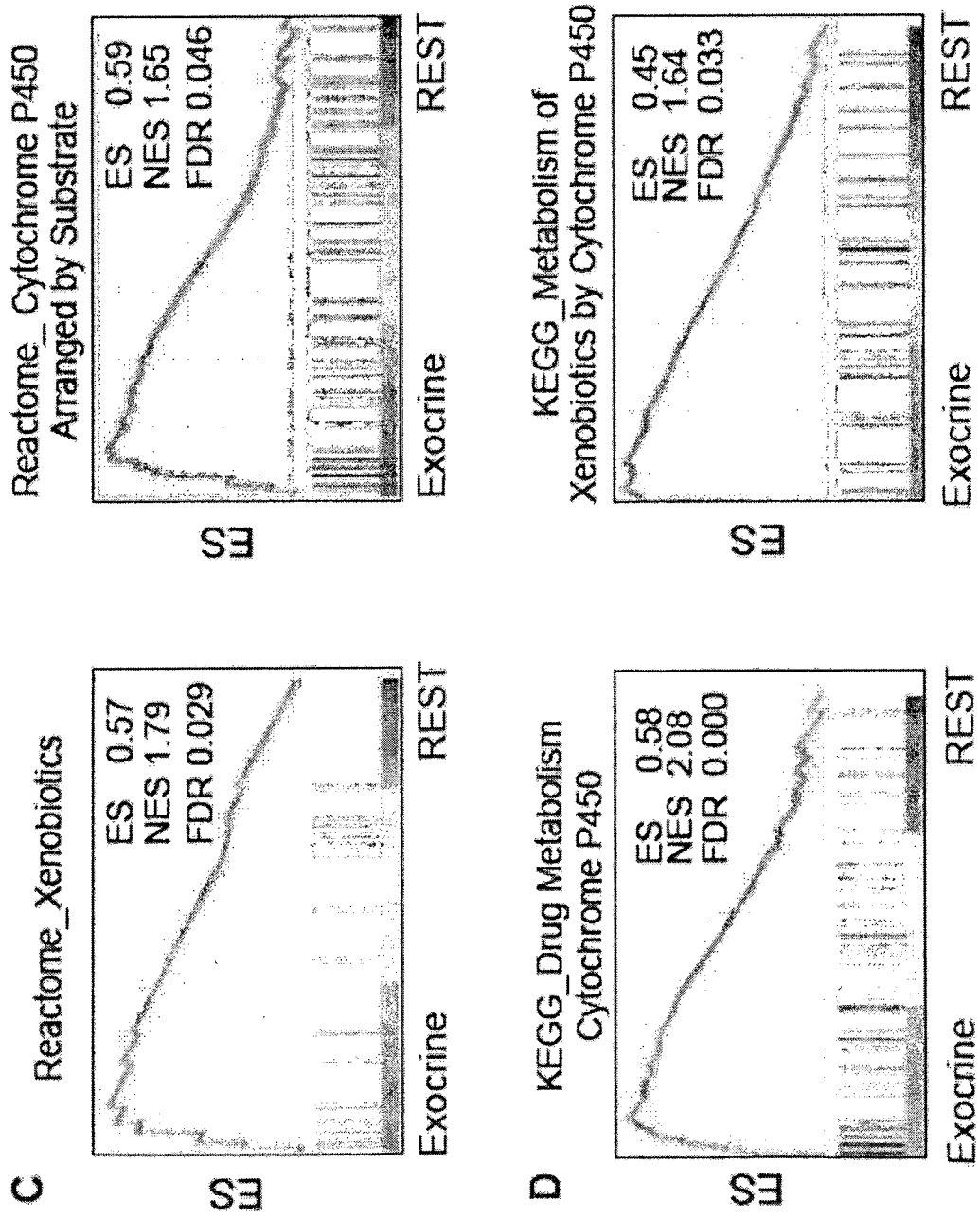
Figure 10 (contd.):

Figure 11:
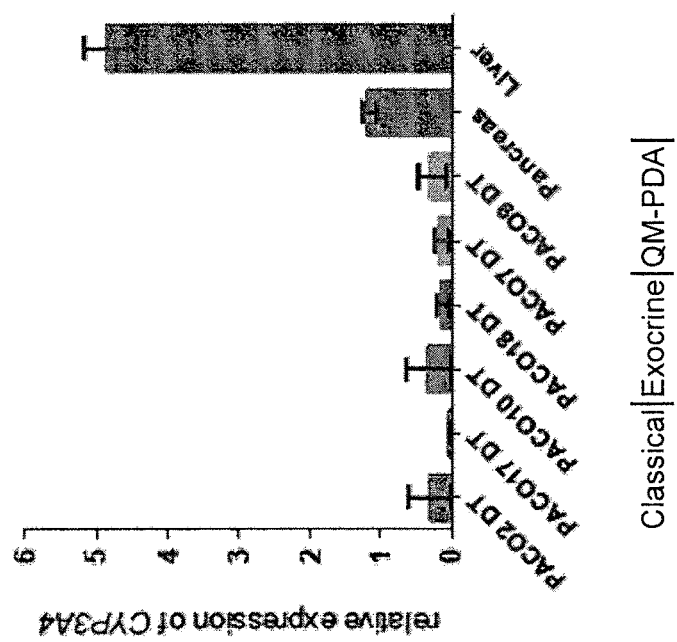
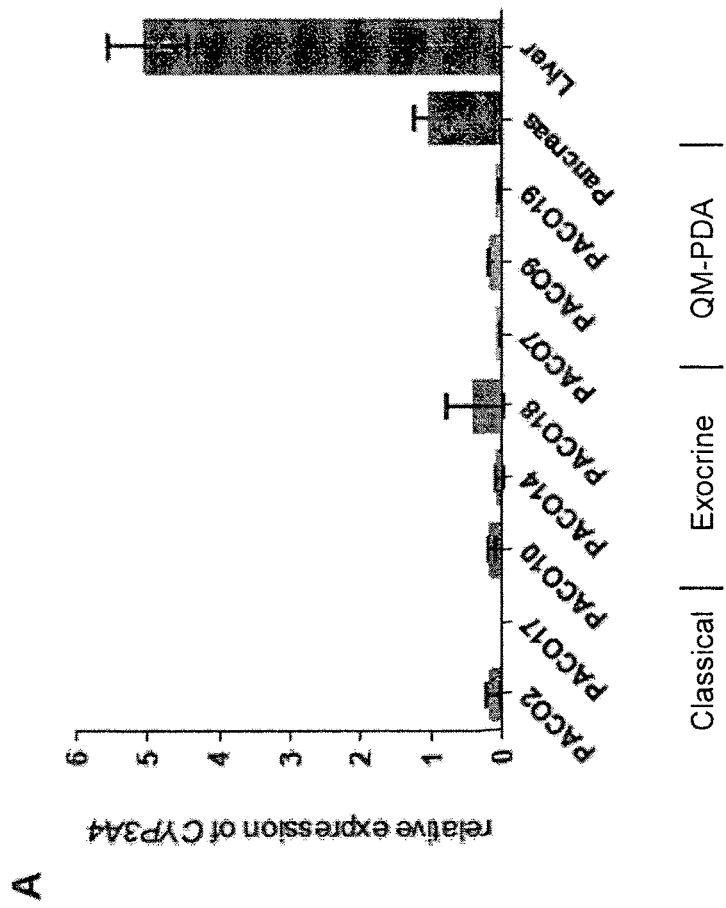

Figure 11 (contd.):
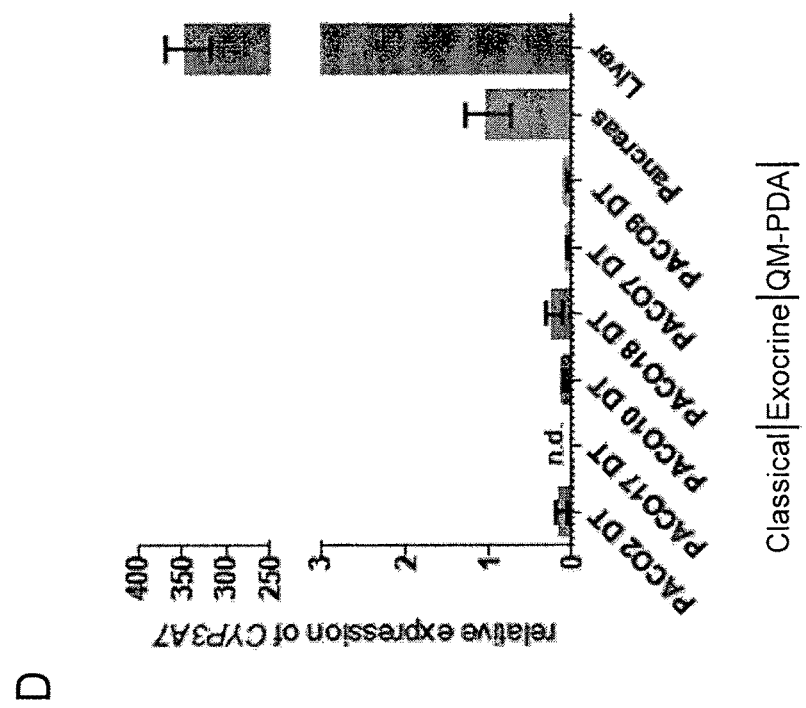
C
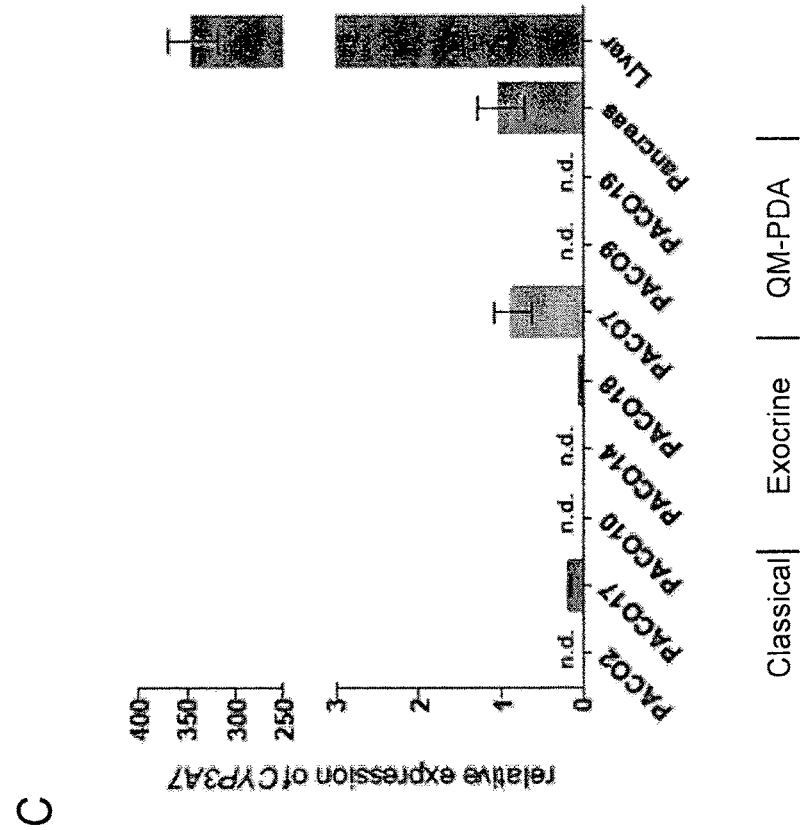
D

Figure 11 (contd.):
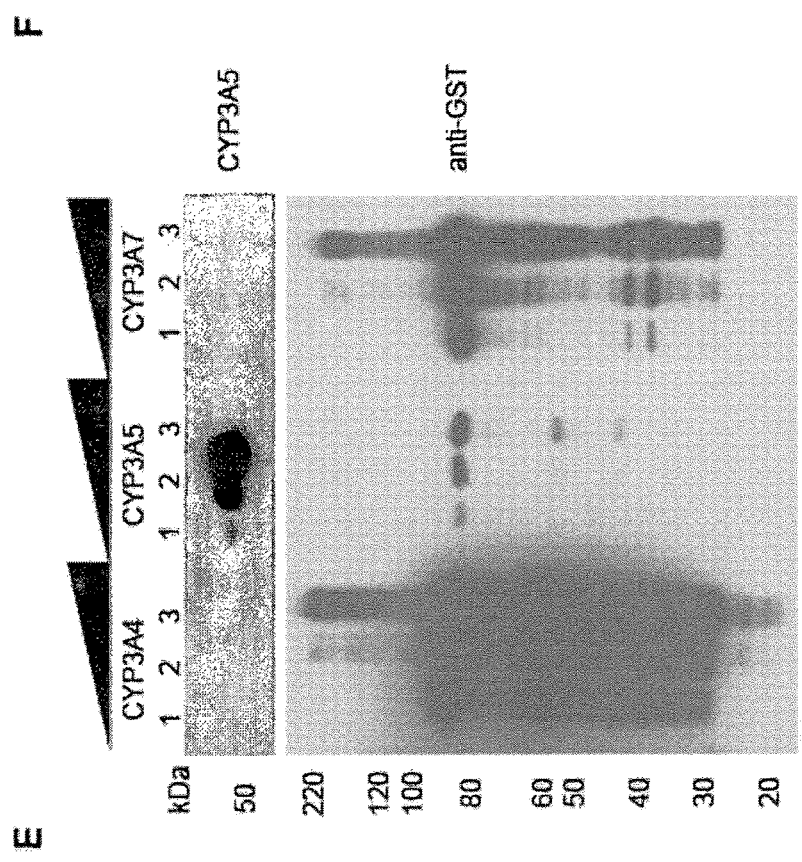
| | All cases | CYP3A5 negative | CYP3A5 positive | p-value |
|---|---|---|---|---|
| All cases | 252 (100%) | 197 (78.2%) | 55 (21.8%) | |
| Age | | | | |
| ≤65 years | 128 (50.8%) | 104 (81.2%) | 24 (18.8%) | 0.147 |
| >65 years | 124 (49.2%) | 93 (75%) | 31 (25%) | |
| Tumor stage | | | | |
| pT1 | 3 (1.2%) | 2 (66.7%) | 1 (33.3%) | 0.701 |
| pT2 | 46 (18.3%) | 39 (84.8%) | 7 (15.2%) | |
| pT3 | 189 (75%) | 144 (76.2%) | 45 (23.8%) | |
| pT4 | 14 (5.6%) | 12 (85.7%) | 2 (14.3%) | |
| Nodal status | | | | |
| pN0 | 68 (27%) | 55 (80.9%) | 13 (19.1%) | 0.327 |
| pN1 | 184 (73%) | 142 (77.2%) | 42 (22.8%) | |
| Grade | | | | |
| G1/G2 | 146 (57.9%) | 112 (76.7%) | 34 (23.3%) | 0.308 |
| G3 | 106 (42.1%) | 85 (80.2%) | 21 (19.8%) | |
| Subtype | | | | |
| QM | 78 (35.1%) | 68 (87.2%) | 10 (12.8%) | <0.001 |
| exocrine | 44 (19.8%) | 17 (38.6%) | 27 (61.4%) | |
| classic | 100 (45%) | 89 (89%) | 11 (11%) | |

Figure 11 (contd.):

G

| Overall survival | | | | |
|---|---|---|---|---|
| | | HR | 95%CI | p-value |
| Age at diagnosis | per year | 1.017 | 1.01-1.03 | 0.033 |
| Tumor stage | pT1/pT2 | 1.00 | | |
| | pT3/pT4 | 1.30 | 0.90-1.89 | 0.166 |
| Lymph node status | pN0 | 1.00 | | |
| | pN1 | 1.84 | 1.29-2.61 | 0.001 |
| Grading | G1/G2 | 1.00 | | |
| | G3 | 1.29 | 0.96-1.72 | 0.91 |
| CYP3A5 | negative | 1.00 | | |
| | positive | 0.65 | 0.46-0.93 | 0.018 |

H

| Total PDAC samples | | sex | | Total | p-value |
|---|---|---|---|---|---|
| | | male | female | | |
| CYP3A5 | negative | 106 | 91 | 197 | 0.337 |
| | positive | 32 | 23 | 55 | |
| Total | | 138 | 114 | 252 | |

| Exocrine-like only | | sex | | Total | p-value |
|---|---|---|---|---|---|
| | | male | female | | |
| CYP3A5 | negative | 6 | 11 | 17 | 0.069 |
| | positive | 17 | 10 | 27 | |
| Total | | 23 | 21 | 44 | |

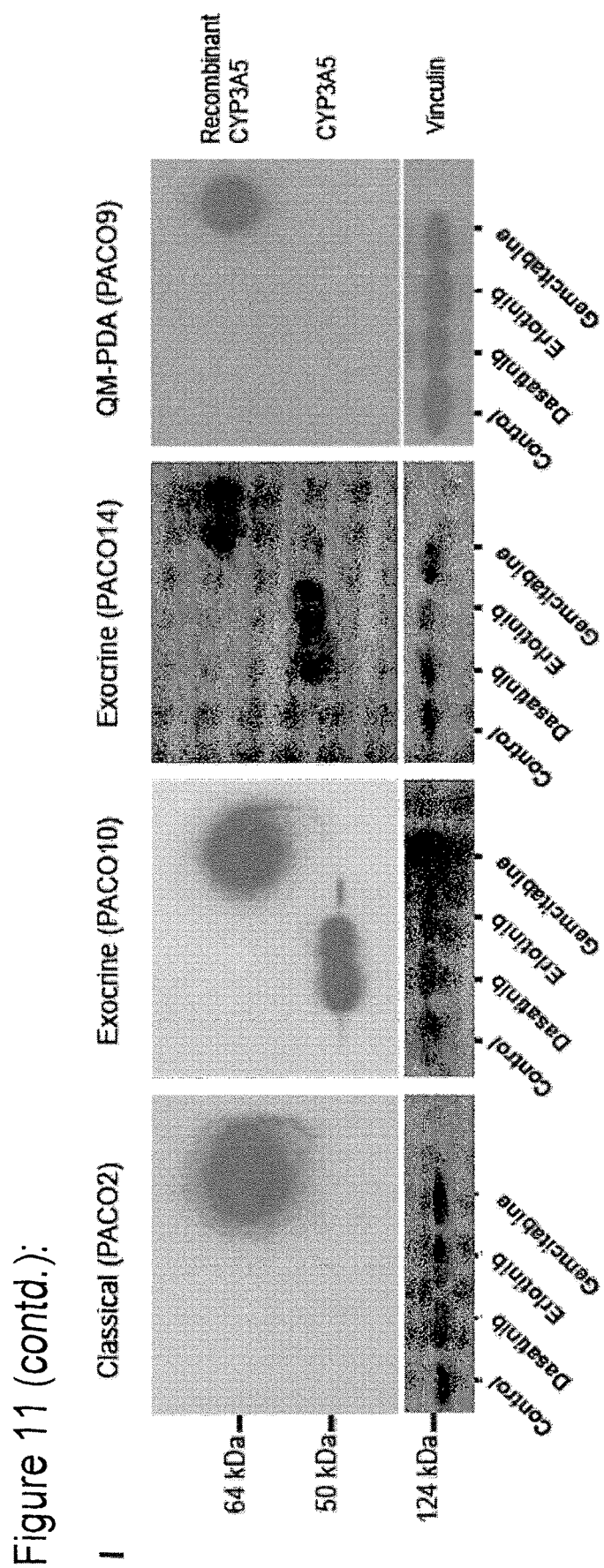
Figure 11 (contd.):

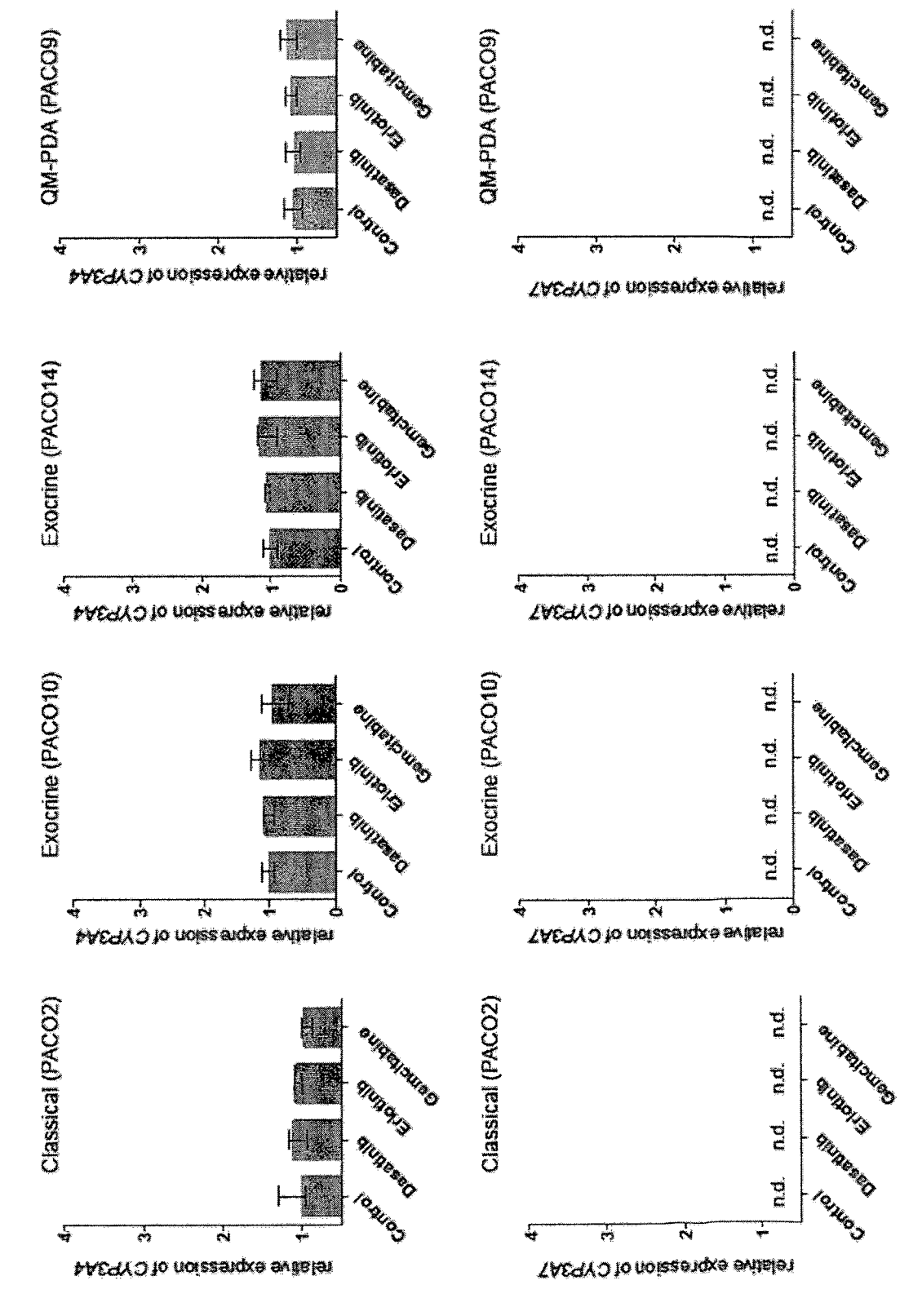
Figure 11 (contd.):
J

Figure 13:
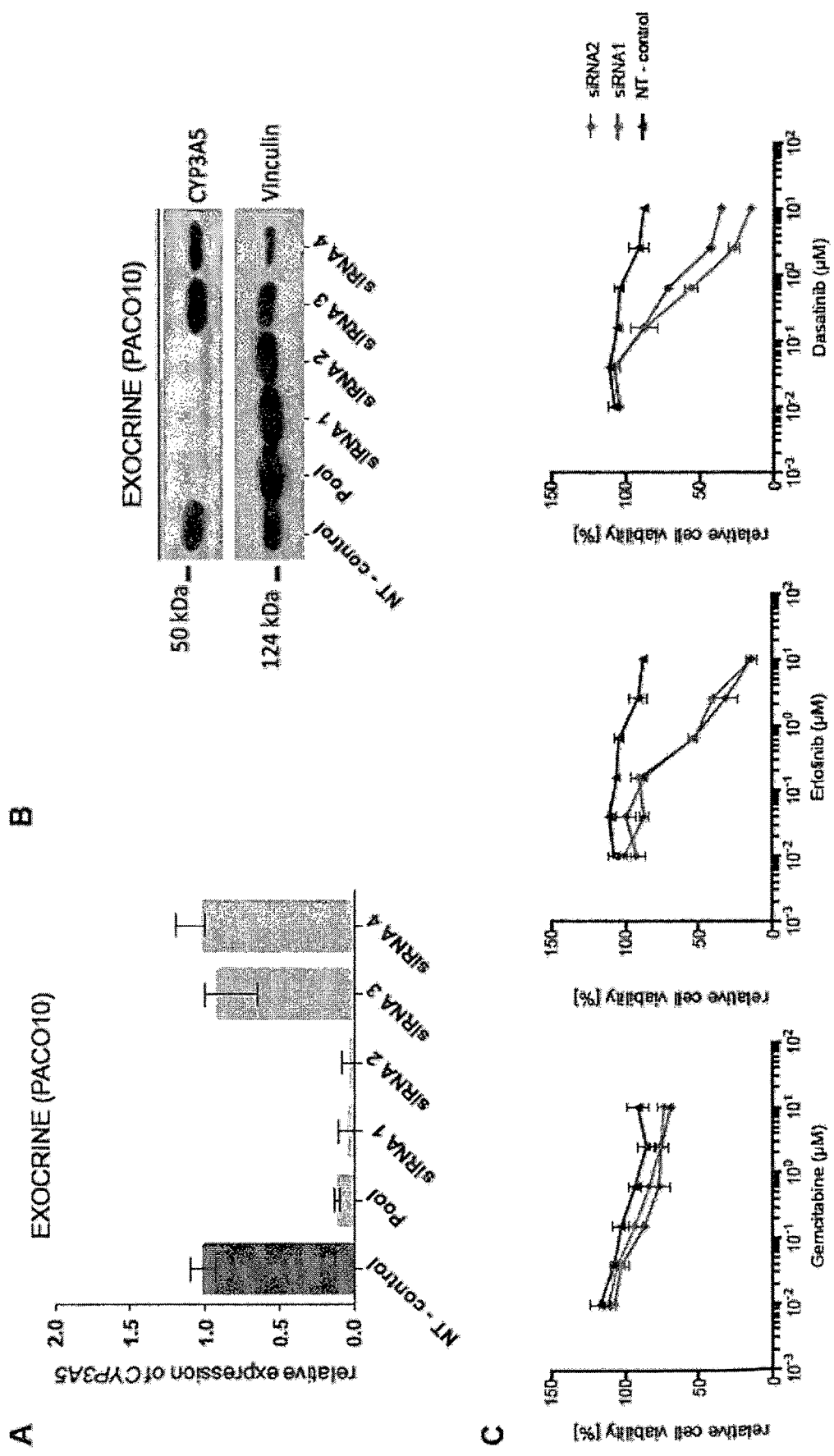
Figure 14:
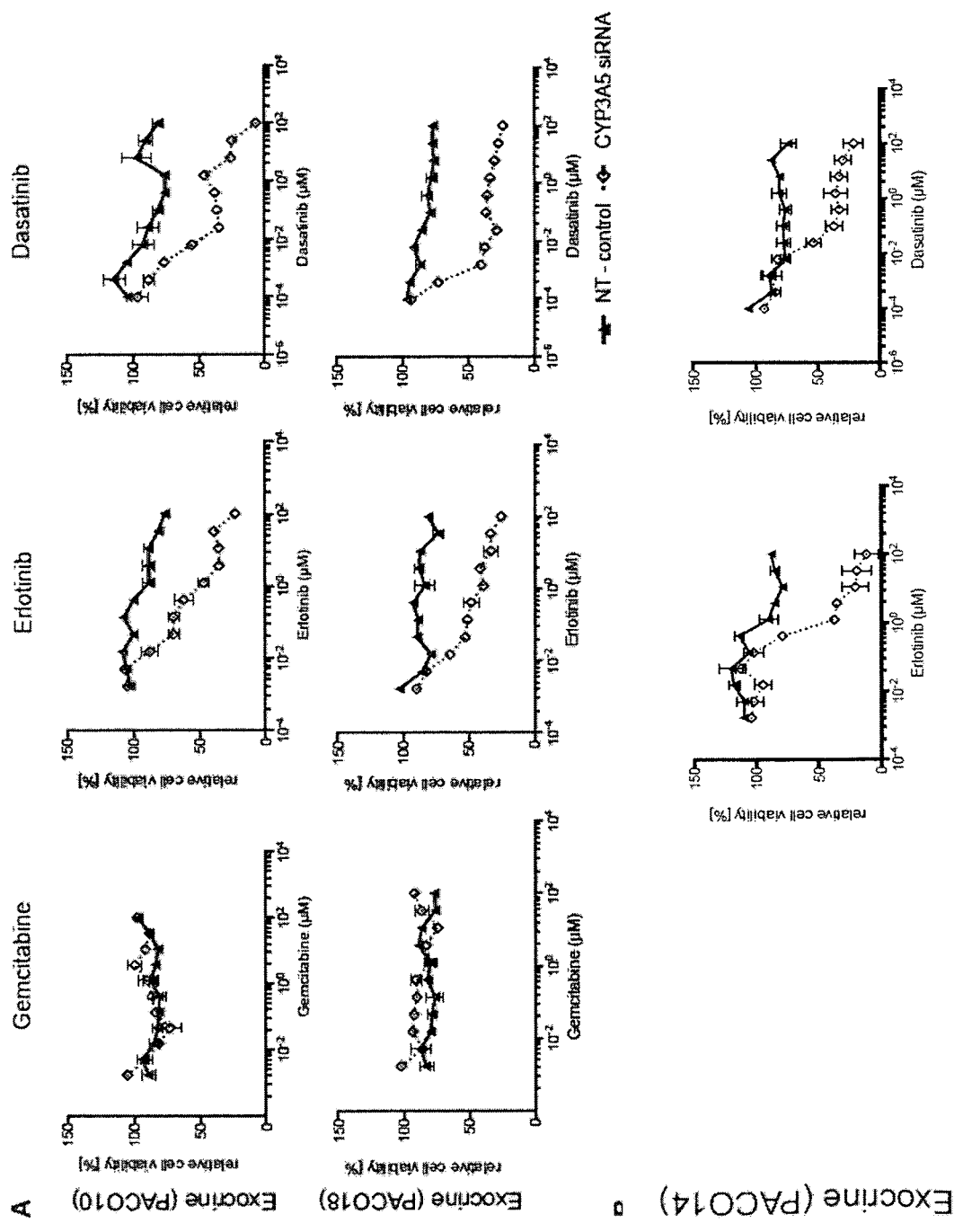

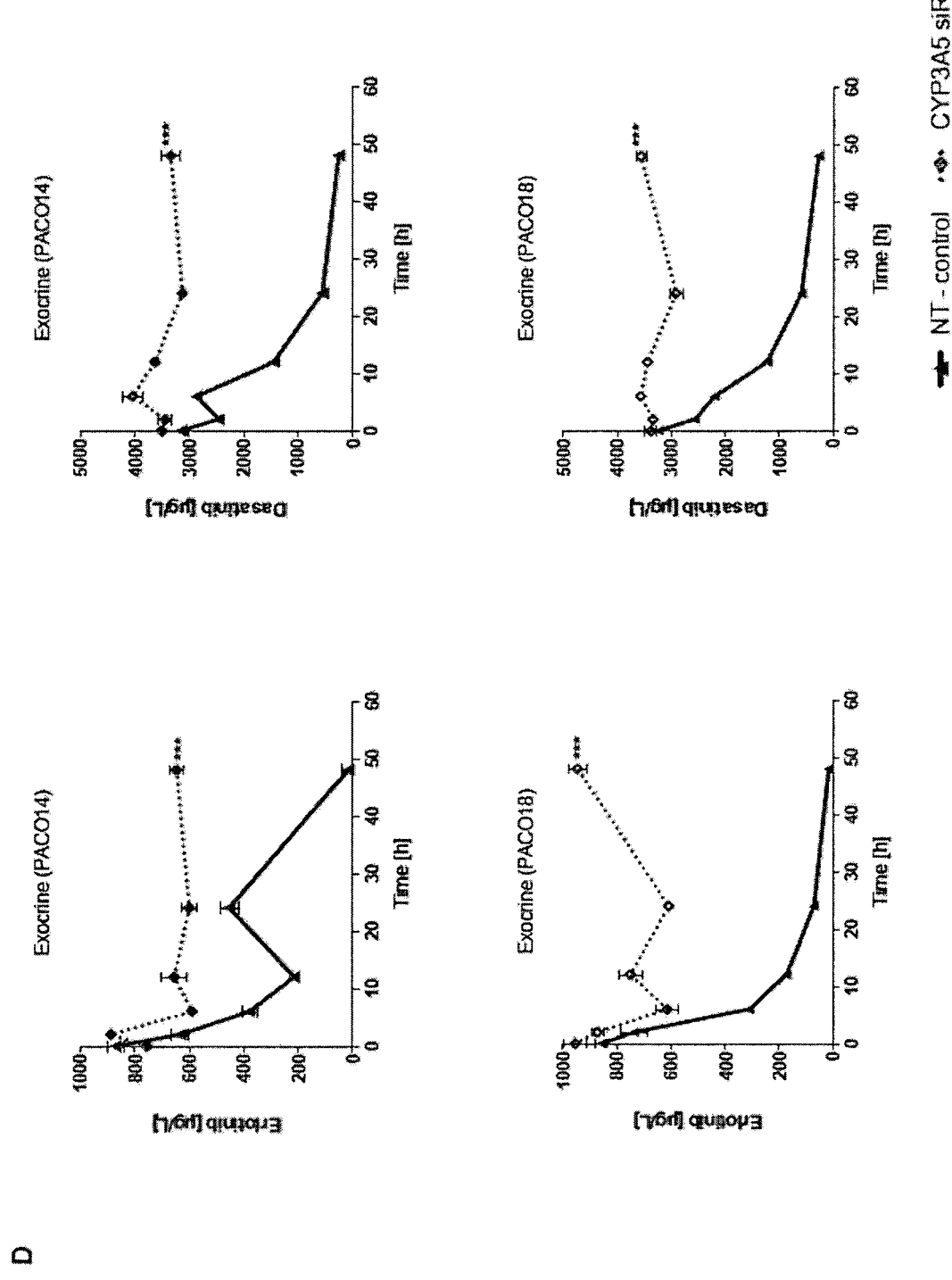
Figure 13 (contd.):

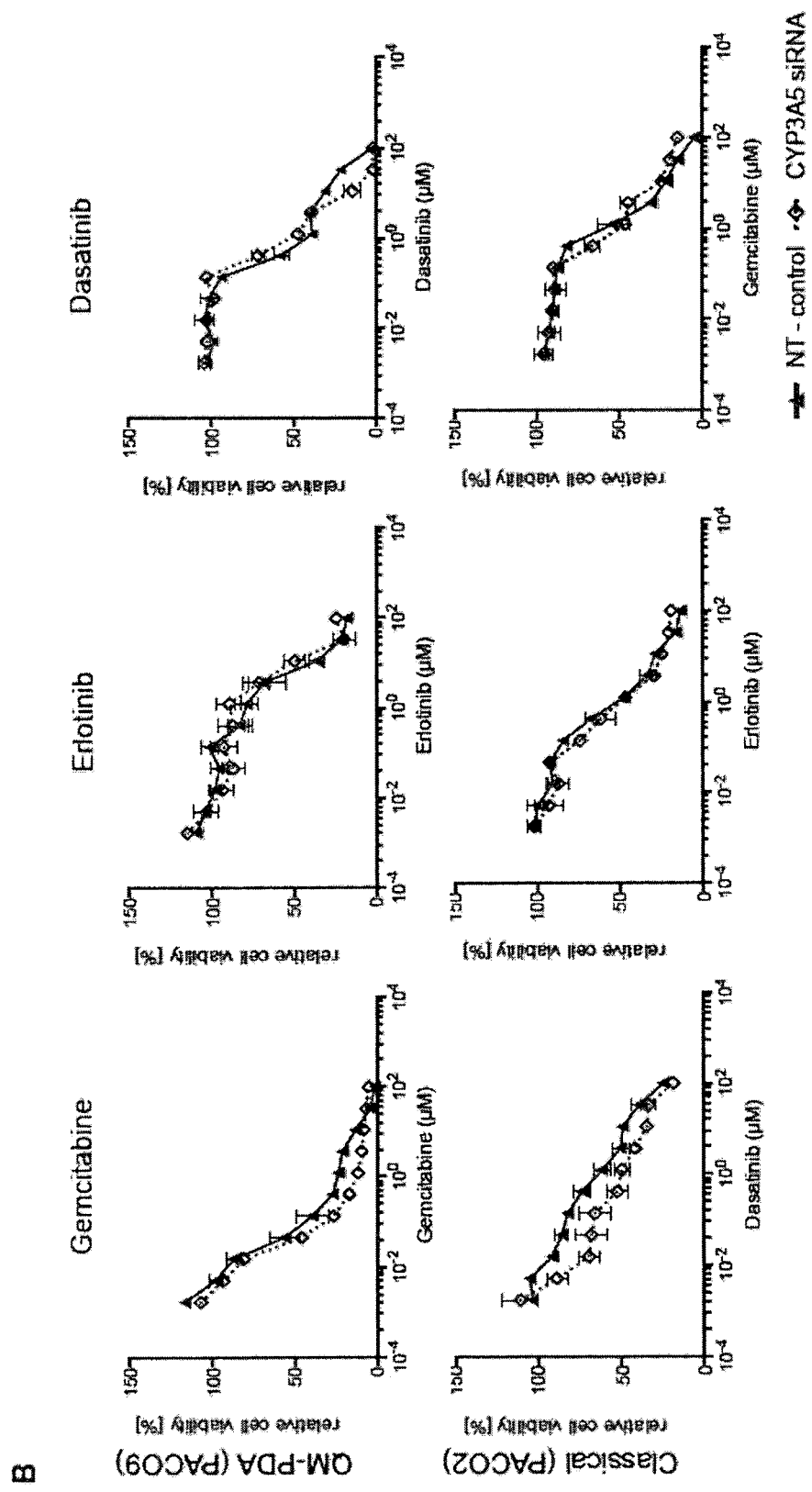
Figure 14 (contd.)

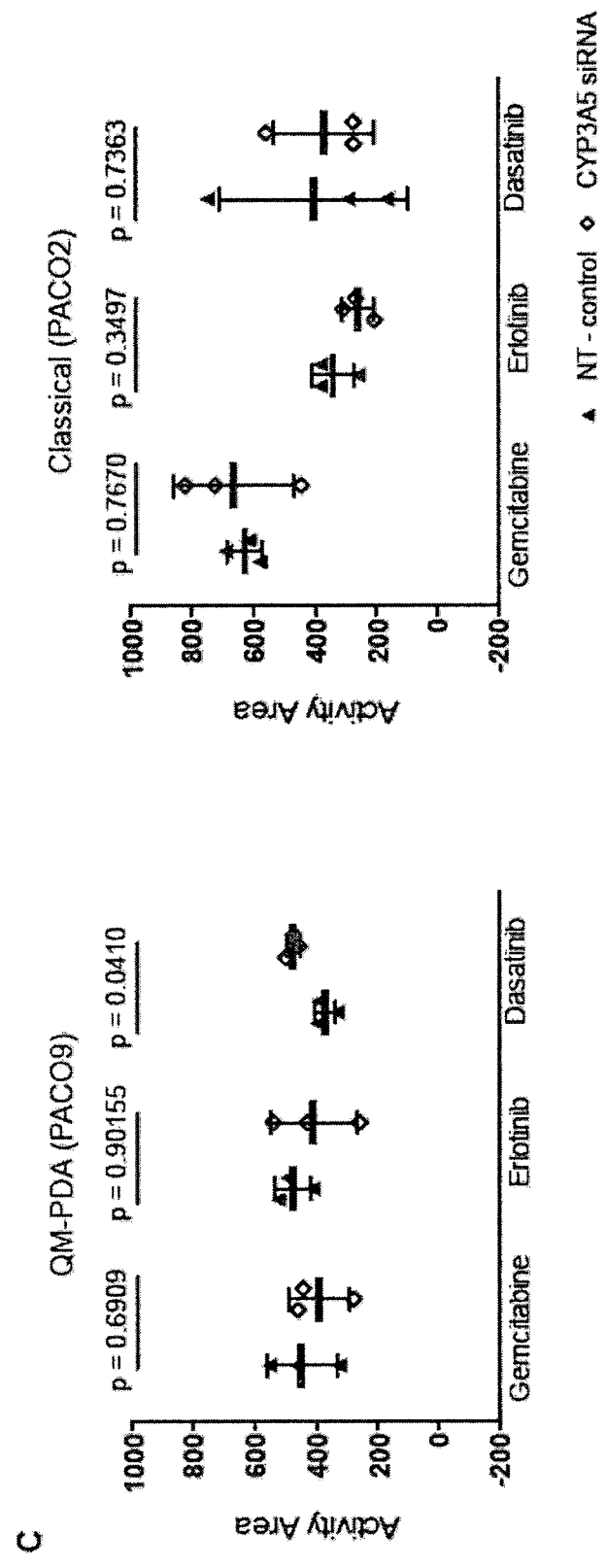
Figure 14 (contd.):

Figure 14 (contd.):
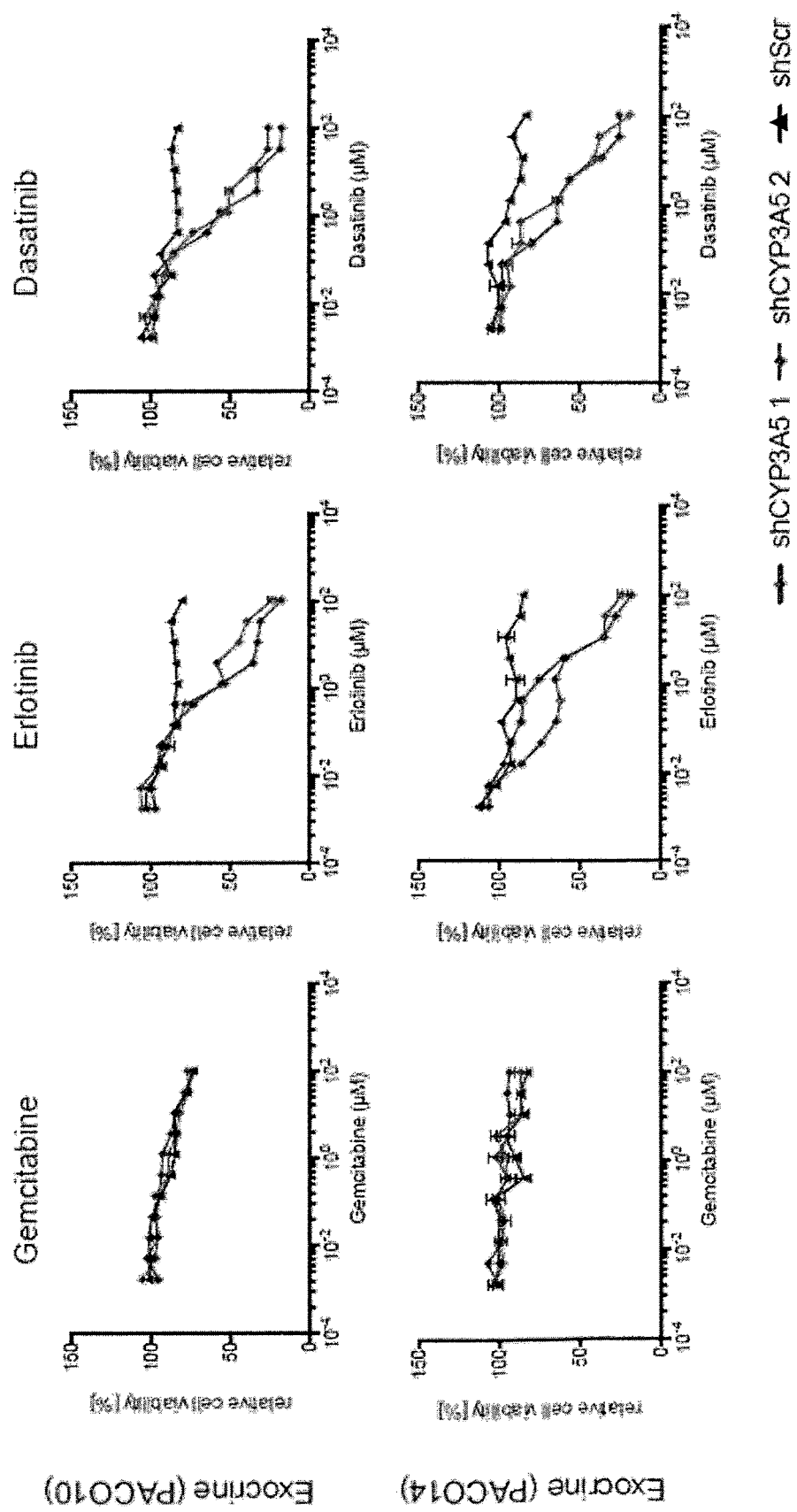

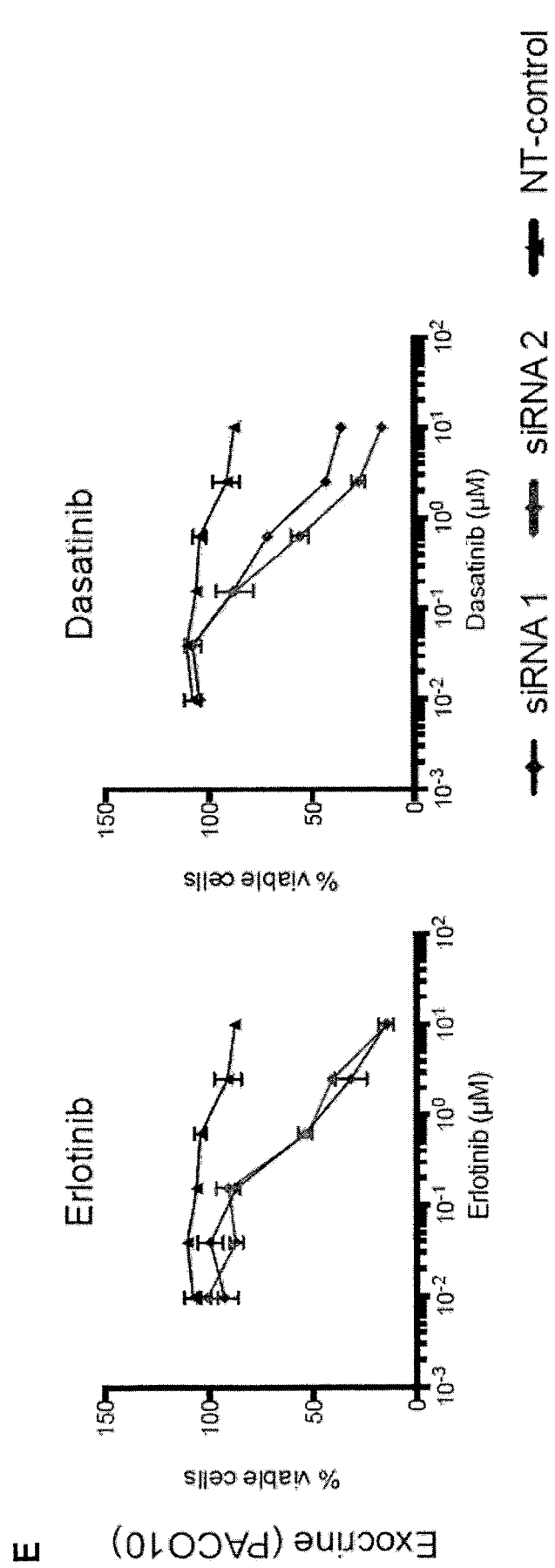
Figure 14 (contd.):

| Tumor type | Staining | % of positive cases | No. of total cases |
|---|---|---|---|
| Adrenal Gland Cortical Carcinoma | ++ | 19 % | 26 |
| Colon Adenoma | + | 32 % | 16 |
| Kidney Transitional Cell Carcinoma | + | 17 % | 18 |
| Hepatocellular Carcinoma | ++ | 56 % | 16 |
| PDAC | + | 60 % | 5 |
| Stomach Adenocarcinoma | +/- | 27 % | 16 |
| Thyroid Papillary Carcinoma | +/- | 40 % | 15 |
| Uterine Cervix Adenocarcinoma | ++ | 12 % | 25 |
| Rectum Adenocarcinoma | + | 38 % | 8 |
| Salivary Glad Parotid | +/- | NA | 1 |
| Melanoma Metastasis to Lymph Node | +/- | 12 % | 9 |
| Melanoma | + | 54 % | 12 |
| Ovary Cyst Adenocarcinoma | + | NA | 1 |
| Thyroid Metastasis to Lymph Node | + | NA | 1 |
| Bile Duct Adenocarcinoma | + | NA | 1 |
| Endometrium Adenocarcinoma | + | 5% | 12 |

Figure 17:
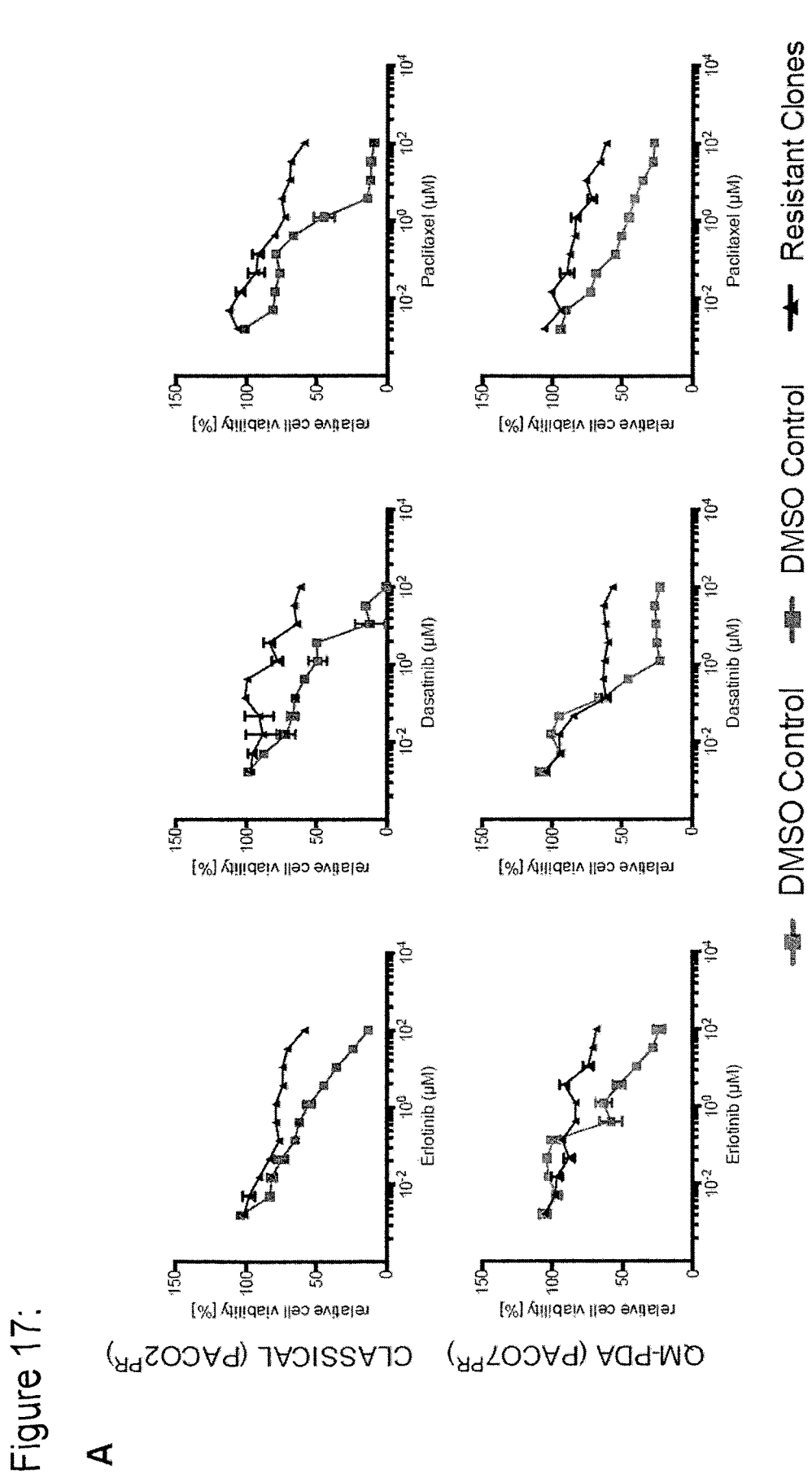

Figure 17 (contd.):
B
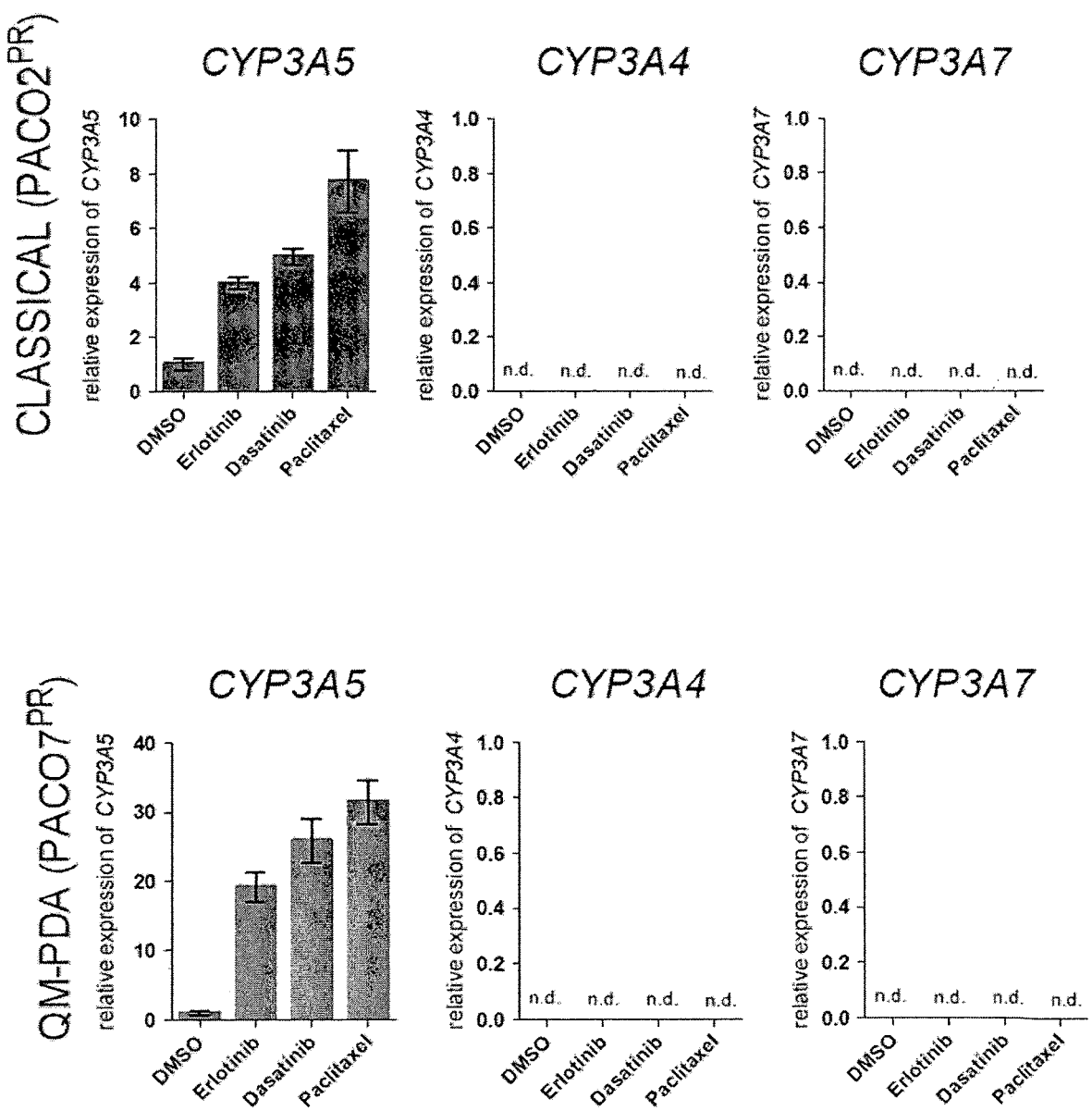

Figure 18:
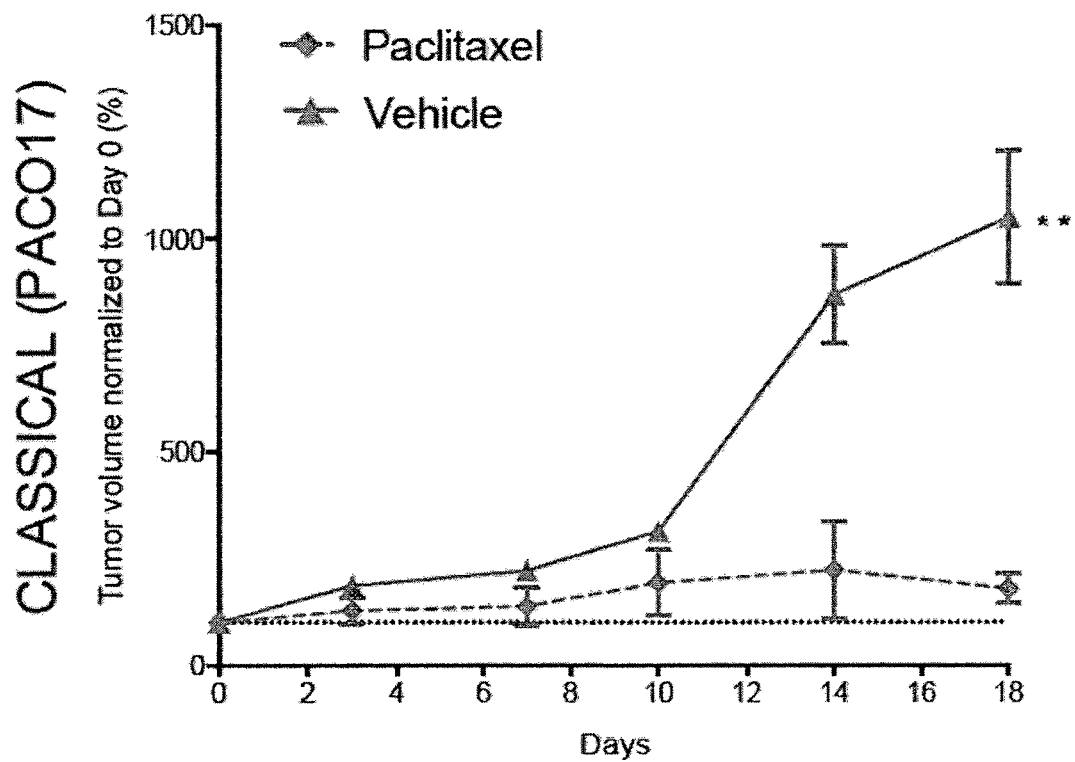
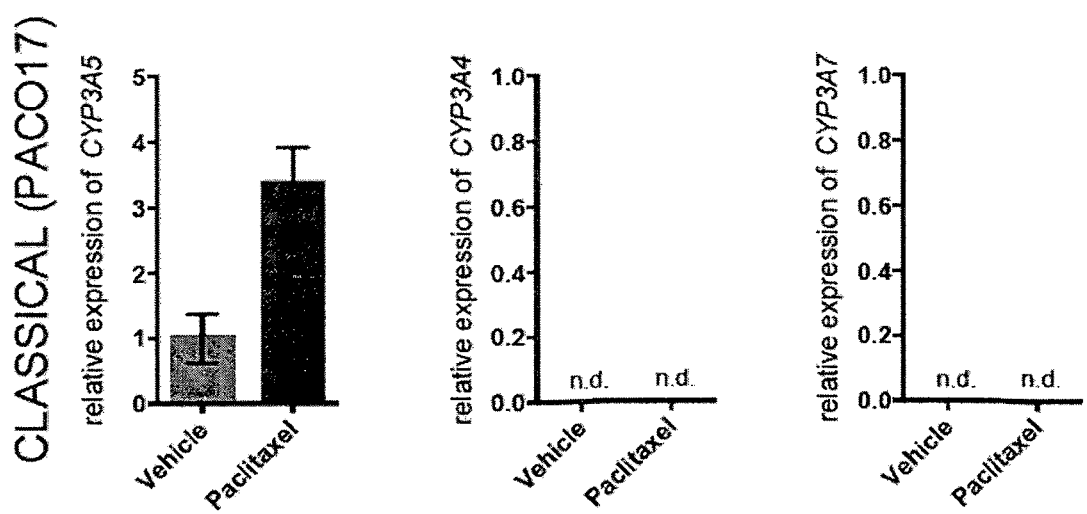

Figure 18 (contd.):
C
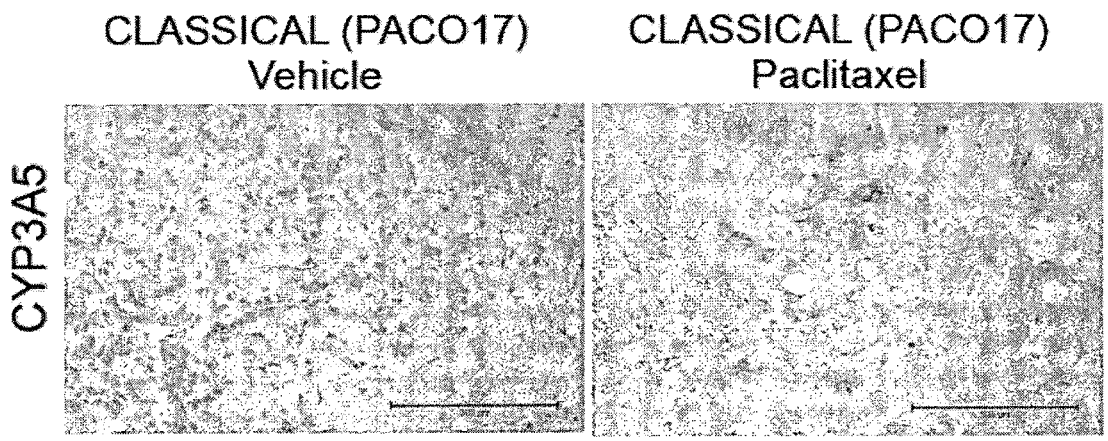
Figure 19:
A
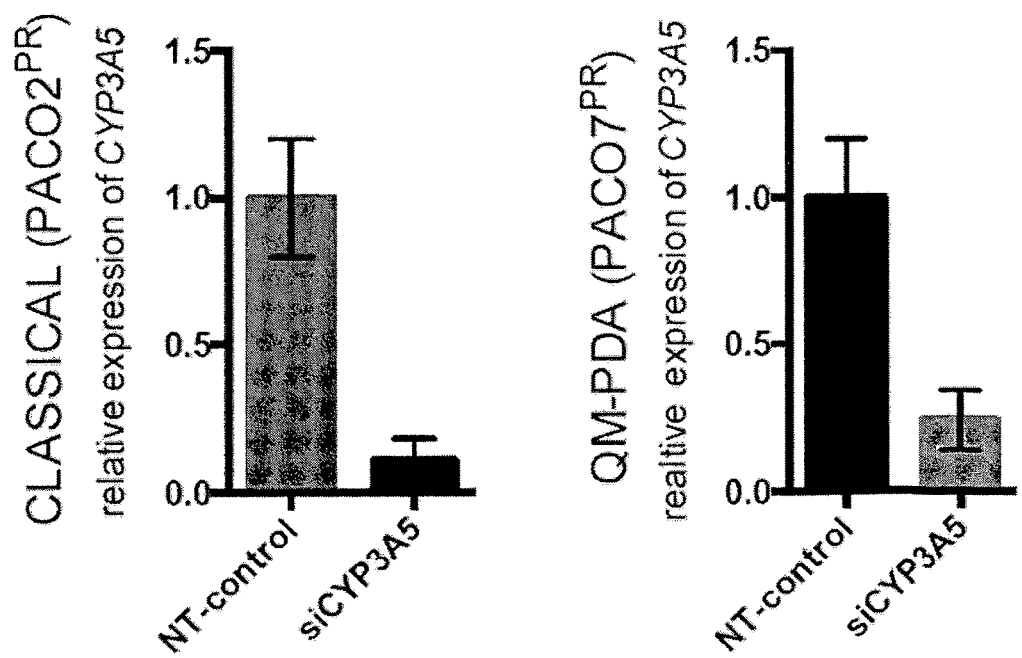

Figure 20:
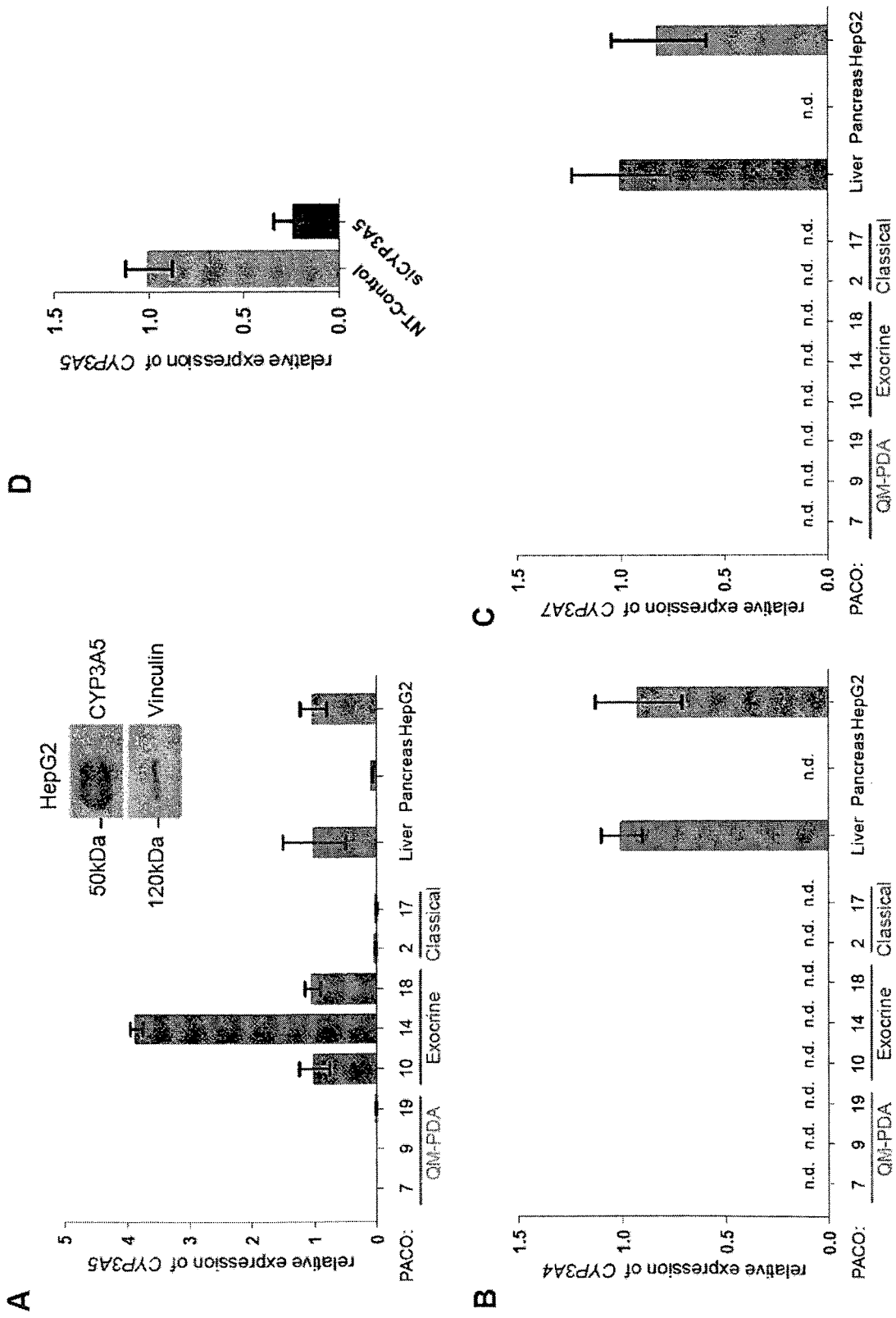

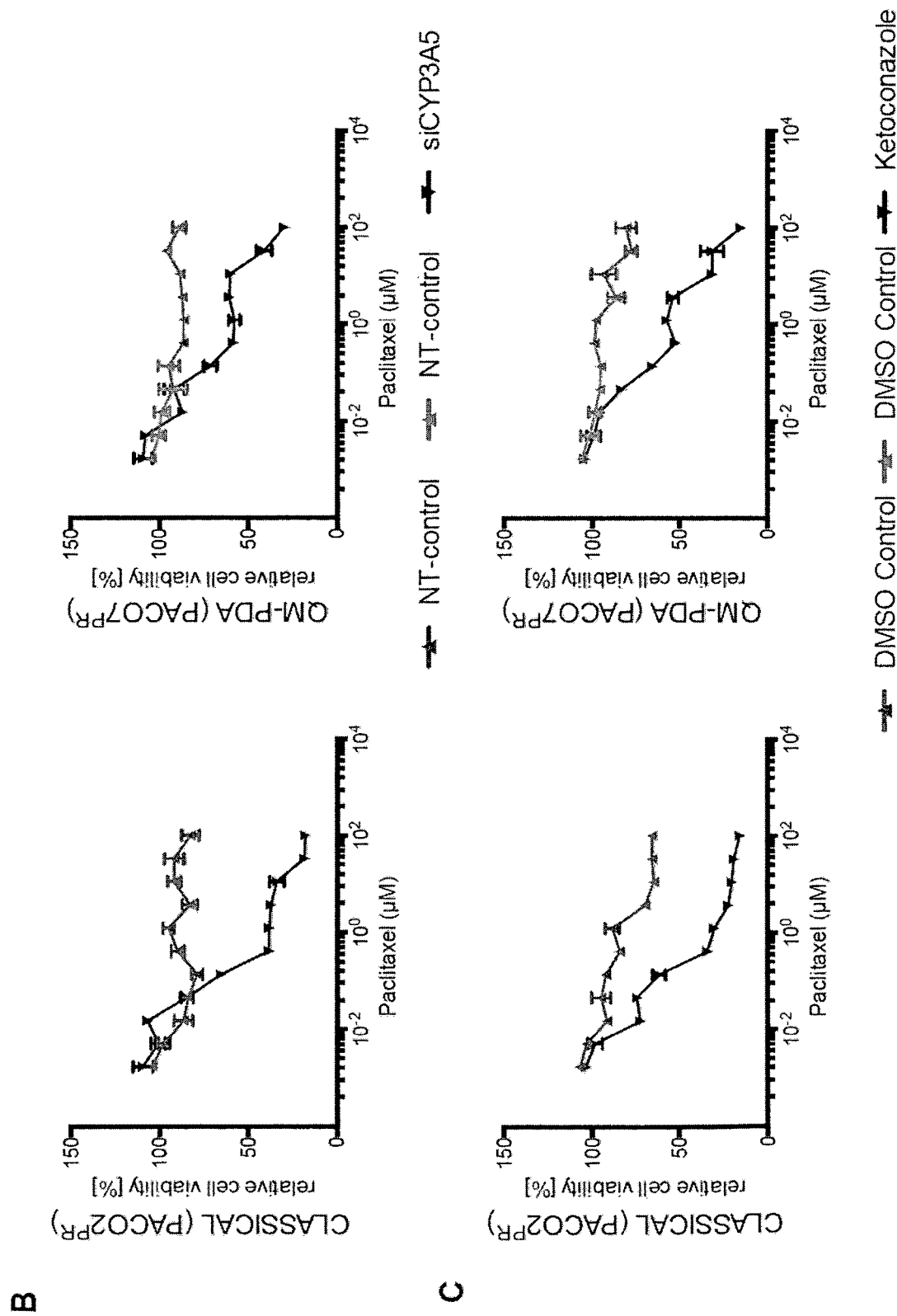
Figure 19 (contd.):

Figure 20 (contd.):
E
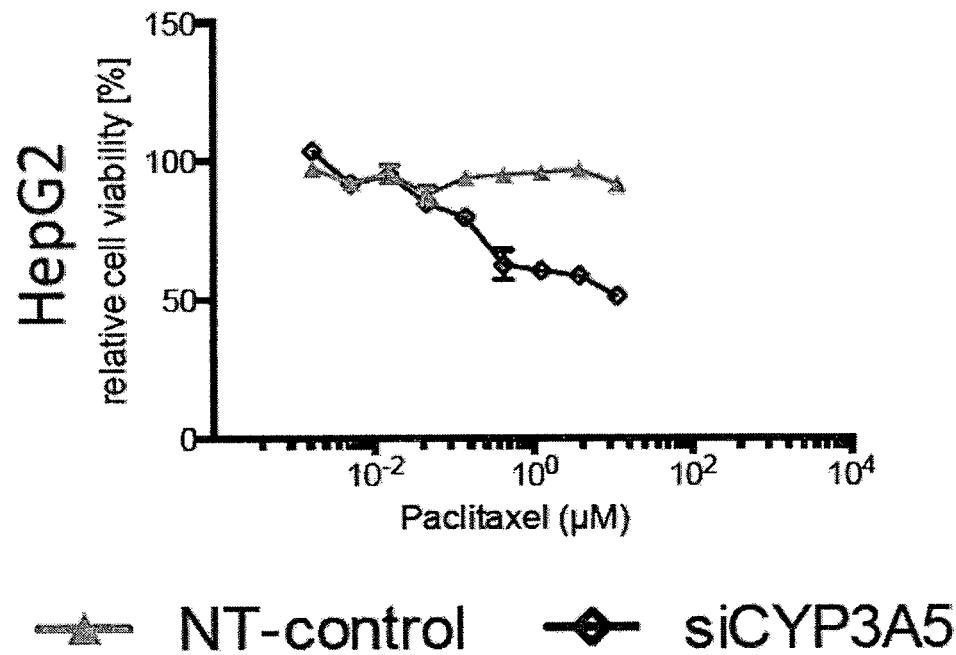
F
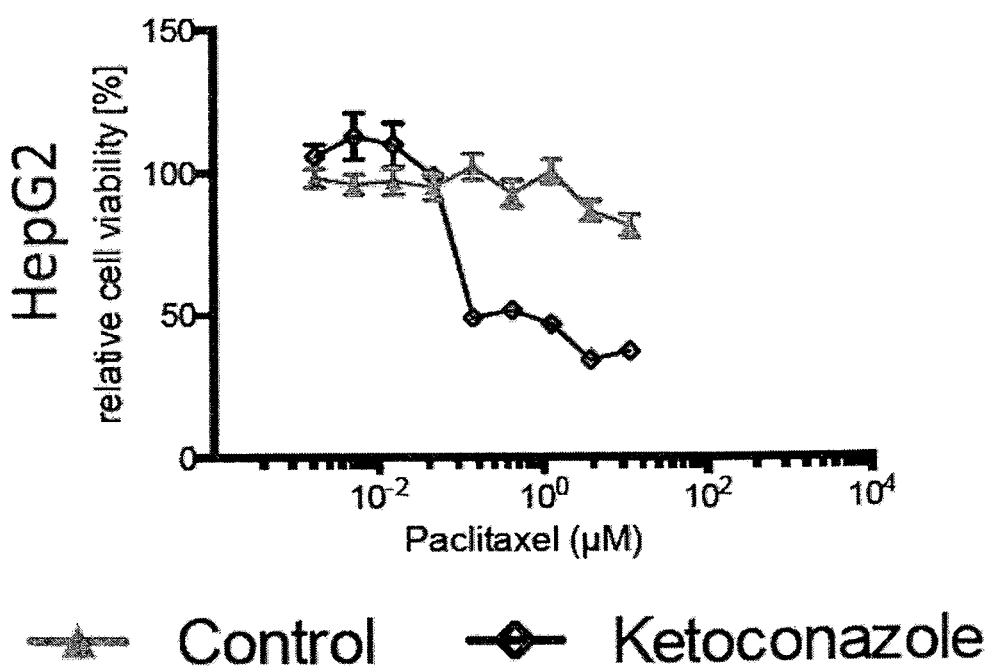

Figure 21:
A
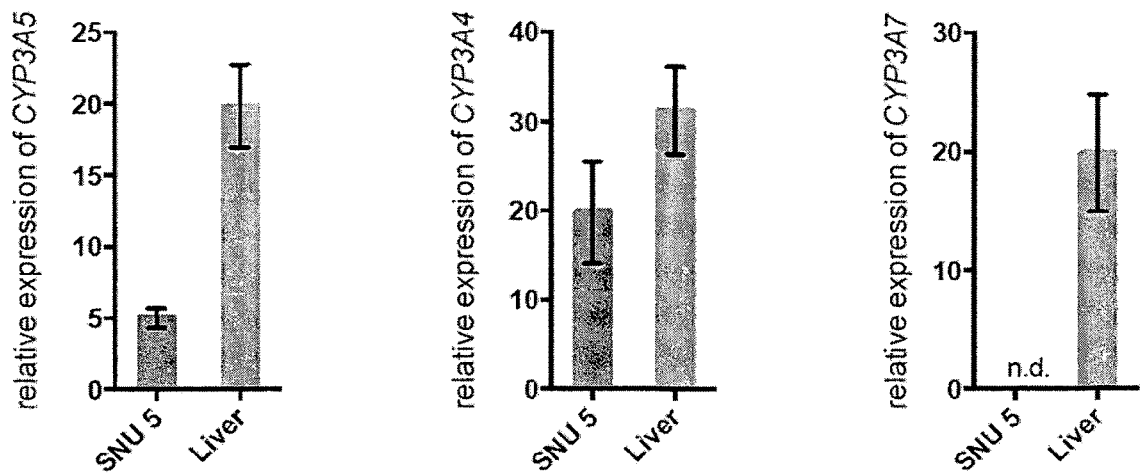
B
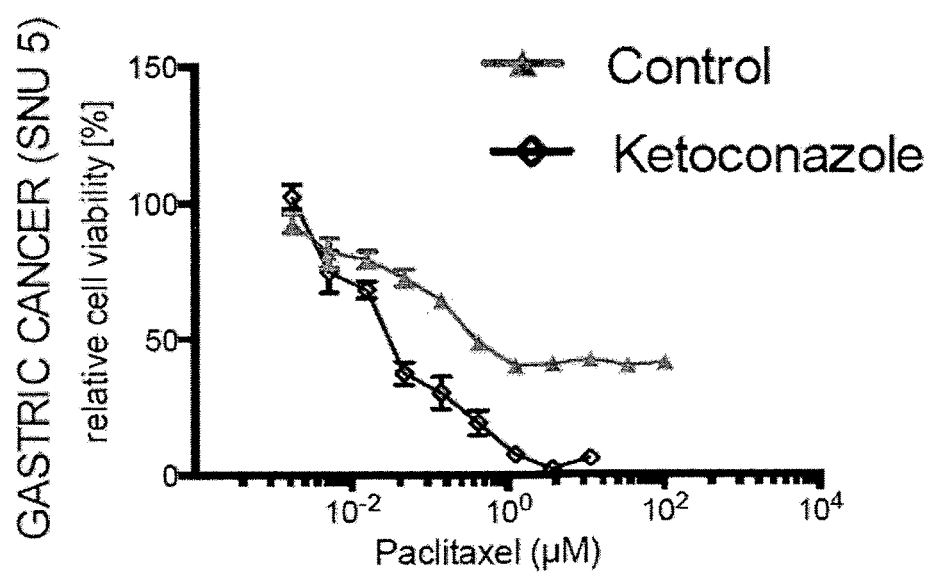

METHODS FOR SUB-TYPING AND TREATING CANCER

CROSS REFERENCE TO RELATED APPLICATIONS

The present invention is filed under 35 U.S.C. § 371 as the U.S. national phase of International Application No. PCT/EP2015/001916, filed Sep. 28, 2015, which designated the U.S. and claims the benefit of priority to European Patent Application No. 14003353.1, filed Sep. 26, 2014, and to European Patent Application No. 15001024.7, filed Apr. 10, 2015 each of which is hereby incorporated in its entirety including all tables, figures and claims.

FIELD OF THE INVENTION

This invention relates to a novel approach for the identification and stratification of subtypes of cancer, particularly pancreatic ductal adenocarcinoma (PDAC). The invention furthermore relates to a novel approach with respect to the treatment of cancer, particularly pancreatic ductal adenocarcinoma (PDAC).

BACKGROUND OF THE INVENTION

Personalized oncology has the potential to revolutionize the way cancer patients will be treated in the future. Different entities of cancer can be divided into subclasses based on molecular differences, including the specific activation of signaling pathways that often determine therapy response and clinical outcome. For various cancer entities including breast, lung and colon cancer, the identification of such subtypes and the possibility to stratify patients into cohorts has already been translated into clinical practice to treat patients in a subtype-specific manner.

PDAC is the most frequent pancreatic cancer and the fourth cause of cancer death in the United States and Europe. Most patients die within 12 months, and only 2% survive five years after prognosis. Little progress in the treatment of PDAC has been made since the approval of gemcitabine in 2000. Apart from gemcitabine (Burris et al., 1997), the recently described FOLFIRINOX scheme (Conroy et al., 2011) and the albumin-paclitaxel conjugate nab-paclitaxel (Von Hoff et al., 2013), treatment options are limited despite extensive research and the discovery of several promising drug candidates (Costello et al., 2012). In a range of tumor types targeted therapies have been successfully implemented (Vanneman and Dranoff, 2012; Zhang et al., 2009). However, these have shown little or no survival benefit for PDAC patients (Hidalgo, 2010; Vincent et al., 2011). One exception is the epidermal growth factor receptor (EFGR) tyrosine kinase inhibitor, erlotinib, which was approved in 2005 and which slightly improves survival in combination treatment with gemcitabine (Moore et al., 2007).

PDAC is still classified as a single cancer entity and is clinically treated as such. However, the existence of three PDAC subtypes termed classical, quasi-mesenchymal (QM-PDA) and exocrine-like has recently been suggested (Collisson et al., Subtypes of pancreatic ductal adenocarcinoma and their differing responses to therapy. Nat. Med. 17 (2011) 500-503). The identification of these subtypes was initially based on comparative gene expression analysis in microdissected epithelial cells form patient specimens. In a large panel of human and murine tumor cell lines only the classical and the QM-PDA subtypes were identified, while no cell line modeled the exocrine-like subtype (Collisson et al., 2011). Recently, a cell line model for the exocrine-like subtype has been developed, and specific biomarkers and/or biomarker patterns have been identified for each of the three subtypes (see WO 2014/056626).

The existence of PDAC subtypes and the possibility to identify such subtypes based on biomarker analysis raises the possibility of identifying inter-subtype specific differences regarding the sensitivity to therapeutic agents. Initially, the classical and the QM-PDA subtype were shown to differ in their response to gemcitabine and erlotinib, while the drug sensitivity of the exocrine-like subtype had yet to be determined (Collisson et al., 2011). The development of a cell line model for the exocrine-like subtype, and the identification of specific biomarkers and/or biomarker patterns (WO 2014/056626) can now be used to stratify patients and to establish individualized therapy approaches for PDAC (see WO 2014/056627).

Thus, despite certain progress that has been made in the characterization and sub-typing of cancers, particularly of PDAC, and the development of stratification and treatment approaches based on such developments, there is still a great need for the development of additional and/or refined methods for cancer patient stratification and the development of more efficient treatment schemes.

The solution to this problem, i.e. the sub-typing of cancers based on the metabolic status of the cancer cells, and the identification of therapeutic approaches that modify and/or interfere with such metabolic status, are neither provided nor suggested by the prior art.

OBJECTS OF THE INVENTION

It was thus an object of the invention to provide a novel approach for the identification and stratification of subtypes of cancer, particularly pancreatic ductal adenocarcinoma (PDAC). Additionally, it was an object of the invention to provide a novel approach with respect to the treatment of cancer, particularly pancreatic ductal adenocarcinoma (PDAC). Such novel approaches would satisfy the great need for quick and reliable patient stratification to greatly improve prognostic evaluation and the introduction of novel cancer treatment approaches exploiting subtype-specific drug vulnerabilities.

SUMMARY OF THE INVENTION

Surprisingly it has been found that a certain enzyme of the cytochrome family is over-expressed and/or upregulated in certain cancer cells. The present finding might be useful to greatly improve prognostic evaluation of patients and cancer treatment approaches by exploitation of subtype-specific drug vulnerabilities. Based on this invention, it is possible (i) to stratify patient populations for clinical studies, which may increase the likelihood that drug development is more successful, since only patients are included in studies that may benefit from the treatment being tested, (ii) to increase the likelihood that a patient receives a treatment that is effective for such a patient, and (iii) to develop new approaches by inhibition of such cytochrome.

Thus, in one aspect, the present invention relates to an in vitro method for the characterization of the metabolic status of tumor cells characterized by the step of measuring expression of cytochrome P450 3A5 (CYP3A5) in said tumor cells.

In another aspect, the present invention relates to a method of stratifying a patient suffering from cancer, particularly of PDAC, particularly PDAC of the exocrine-like subtype, into a treatment cohort, the method comprising the steps of (a) in vitro measuring expression of cytochrome P450 3A5 (CYP3A5) in tumor cells obtained from said patient; (b) determining the metabolic status of said tumor cells as either CYP3A5-positive or CYP3A5-negative; and (c) stratifying said patient into a drug treatment cohort based on the metabolic status determined in step (b).

In another aspect, the present invention relates to a specific inhibitor of cytochrome P450 3A5 (CYP3A5) for use in the treatment of cancer, particularly a cancer comprising CYP3A5-positive cancer cells, particularly of PDAC, particularly PDAC of the exocrine-like subtype.

In another aspect, the present invention relates to a method for the treatment of cancer, particularly a cancer comprising CYP3A5-positive cancer cells, particularly of PDAC, particularly PDAC of the exocrine-like subtype comprising the step of administering a specific inhibitor of cytochrome P450 3A5 (CYP3A5) to a patient in need thereof.

In another aspect, the present invention relates to a drug combination of (i) a specific inhibitor of cytochrome P450 3A5 (CYP3A5) and (ii) one or more additional therapeutic agents, for use in the treatment of cancer, particularly a cancer comprising CYP3A5-positive cancer cells, particularly of PDAC, particularly PDAC of the exocrine-like subtype.

In another aspect, the present invention relates to a method for the combination treatment of cancer, particularly of PDAC of the exocrine-like subtype, comprising the step of administering a specific inhibitor of cytochrome P450 3A5 (CYP3A5) in combination with one or more additional therapeutic agents for use in the treatment of cancer, particularly a cancer comprising CYP3A5-positive cancer cells, particularly of PDAC, particularly PDAC of the exocrine-like subtype, to a patient in need thereof.

FIGURES

FIG. 1 shows the establishment of PDAC models representing all three described PDAC subtypes. (A) Schematic overview of the experimental workflow used to generate orthotopic xenografts and PACO cells. (B) Representative pictures of the specimens depicted in the scheme in (A). H&E staining of a primary human PDAC tumor, the corresponding first passage xenograft (PT), bright field picture of the derived PACO cells (PACO10) and the respective PACO derived tumor (DT). Scale bar=100 μm. (C) Representative Pearson correlation analysis of log 2 gene expression data from PT versus DT xenografts, PACO10 passage 3 (p3) versus passage 15 (p15), and DT versus PACO10 passage 7 (p7) (****p<10-3). (D-E) Gene set enrichment analysis (GSEA) using the PDAssigner geneset (Collisson et al., 2011) on gene expression profiles of the PACO cell lines (PACO2, PACO10, PACO9) (D) and the respective PT and DT xenografts (E). ES, Enrichment Score; NES, Normalized Enrichment Score; FDR, False Discovery Rate.

FIG. 2 shows the identification and prognostic value of a novel two-marker set for PDAC subtypes. (A) Keratin 81 (KRT81) and HNF1A immunofluorescence staining of representative PACO cell lines of the different subtypes: Classical (PACO2), exocrine-like (PACO10), and QM-PDA (PACO7). Scale bar=50 μm. (B) Immunohistochemical staining for KRT81 and HNF1A of the PACO derived xenografts (DT) shown in (A). Scale bar=100 μm. (C) Representative KRT81 and HNF1A stainings of a tissue microarray (TMA) containing 251 primary PDAC patient tumors. (D) Kaplan-Meier curve depicting the overall survival of 217 PDAC patients form the TMA that were grouped according to marker-defined subtypes (p<0.0001 according to Log-rank (Mantel-Cox) Test). (E) Cox proportional hazards multivariate analysis revealed age at diagnosis, lymph node status, and subtype defined by the novel immunohistochemical markers as independent predictors for PDAC patient survival (p<0.001).

FIG. 3 shows that PDAC subtypes differ in drug sensitivity. (A) Scatter plots showing relative cell viability [%] in response to 10 μM gemcitabine, erlotinib and dasatinib, respectively. Each dot represents an individual PACO cell line. Horizontal bars depict mean±SEM (n=2; *p=0.05, grouped One-Way ANOVA, Bonferroni correction); upper part: after 48 hours, lower part: after 7 days. (B-E) GSEA plot of the exocrine-like PACO lines (B) and PT+PD xenografts (D) versus rest (classical and QM-PDA subtype) using the drug metabolism gene signatures illustrated. (C, E) Tables showing enrichment statistics for different metabolic gene signatures tested. Data represent enrichment of the exocrine-like subtype versus the rest. ES, Enrichment Score; NES, Normalized Enrichment Score; FDR, False Discovery Rate.

FIG. 4 shows the subtype-specific expression and induction of CYP3A5 in vitro and in vivo. (A-B) mRNA expression of CYP3A5 in the PACO lines (A), PACO derived xenografts (DT) (B), compared to normal pancreas and liver. Values are relative to PACO18 mRNA expression. Values are mean±SEM (n=3; *p<0.05; grouped One-Way ANOVA, Bonferroni correction). (C) Anti-CYP3A5 immunoblot of whole PACO cell lysates. Vinculin was used as loading control. L=normal human liver protein lysate (D) Representative CYP3A5 staining of human PDAC paraffin sections from the TMA. Arrows indicate CYP3A5 positive cells. Scale bar=100 μm. (E) Percentage of CYP3A5 positive and negative tumors among the different PDAC subtypes as determined by immunohistochemical staining of the TMA. Significance was calculated with the Log-rank (Mantel-Cox) Test (p<0.001). (F) mRNA and western blot analysis of CYP3A5 expression at basal level and in response to 10 μM dasatinib, erlotinib and gemcitabine in PACO cells of the classical (PACO2), exocrine-like (PACO10, PACO14) and QM-PDA (PACO9) subtypes. Values are mean±SEM (n=3; *p<0.05; **p<0.01; One-Way ANOVA, Bonferroni correction). Vinculin was used as loading control.

FIG. 5 shows that pan-cytochrome P450 inhibition sensitizes exocrine-like PDAC cells to tyrosine kinase inhibitors (A) Dose response curves for PACO cells (exocrine-like (PACO14), classical (PACO2), QM-PDA (PACO9)) pretreated with 100 nM ketoconazole or vehicle for 2 hours, followed by the addition of erlotinib or dasatinib at the indicated concentrations. Relative cell viability [%] was determined 48 hours after drug treatment (n=3). (B) Activity area values for ketoconazole or vehicle pre-treated PACO cells (exocrine-like (PACO14), classical (PACO2), QM-PDA (PACO9)), followed by the addition of serial dilutions of the indicated drugs for 48 hours. Each dot represents one biological replicate. Horizontal bars depict mean±SEM (n=3; paired t-Test).

FIG. 6 shows that CYP3A5 metabolizes erlotinib and dasatinib in exocrine-like PDAC cells. (A) mRNA expression of CYP3A5, comparing non-targeting (NT) to CYP3A5 siRNA transfected exocrine-like PACO cells (PACO10, PACO14, PACO18). Values are mean±SEM (n=3; p<0.01; *p<0.001; One-Way ANOVA, Bonferroni correction). (B) Anti-CYP3A5 immunoblot of untreated, non-targeting (NT–control) and CYP3A5 siRNA transfected exocrine-like PACO cells. Vinculin was used as loading control. (C) Erlotinib and dasatinib concentrations [μg/l] in the supernatant of two exocrine-like PACO cell lines (PACO14, PACO18), transfected with CYP3A5 or non-targeting (NT–control) siRNA, and subsequent treatment with 10 μM erlotinib (left panel) or 10 μM dasatinib (right panel). Shown are compound concentrations of supernatants collected at the indicated time points. Values were calculated by mass spectrometric analysis (LC-MS/MS) (n=6; ***p<0.001; Two-Way ANOVA, Bonferroni correction).

FIG. 7 shows that CYP3A5 mediates drug resistance in exocrine-like PDAC cells. (A) Representative dose response curves of CYP3A5 or non-targeting (NT–control) siRNA transfected exocrine-like PACO cell line (PACO14) in response to serial dilutions of gemcitabine, erlotinib and dasatinib. Relative cell viability [%] was determined 48 hours after drug treatment (n=3). (B) Activity area values for CYP3A5 or non-targeting (NT–control) siRNA transfected exocrine-like PACO cells (PACO10, PACO14, PACO18) in response to serial dilutions of gemcitabine, erlotinib or dasatinib for 48 hours. Each dot represents one biological replicate. Horizontal bars depict mean±SEM (n=3; paired t-Test). (C) mRNA and protein expression of CYP3A5, comparing scrambled control (shScr) to CYP3A5 shRNA (shRNA 1 and 2) transduced exocrine-like PACO cells (PACO10, PACO14). Values are mean±SEM (n=3; *p<0.05; p<0.01; One-Way ANOVA, Bonferroni correction). Vinculin was used as loading control. (D) Schematic outline of the treatment experiment shown in (E). (E) Growth kinetics of tumors derived from CYP3A5 stable knockdown (shCYP3A5) or scrambled control cells (shScr) of two exocrine-like PACO lines treated with 100 mg/kg erlotinib for 5 consecutive days followed by two days of rest, for a duration of 14 days. n=6 mice per treatment group. Day 0 was defined as day of treatment start. Data are represented as mean±SEM (p<0.01; n.s.=not significant; one-sided Mann-Whitney U test). (F) CYP3A5 mRNA expression in tumors derived from shCYP3A5 2 or shScr cells of two exocrine-like lines (PACO10, PACO14) post erlotinib or vehicle treatment (E). Values are relative to the vehicle treated shScr group mRNA expression. Values are mean±SEM (n=3; *p<0.05; *p<0.01; Student's T-test).

Figure 8:
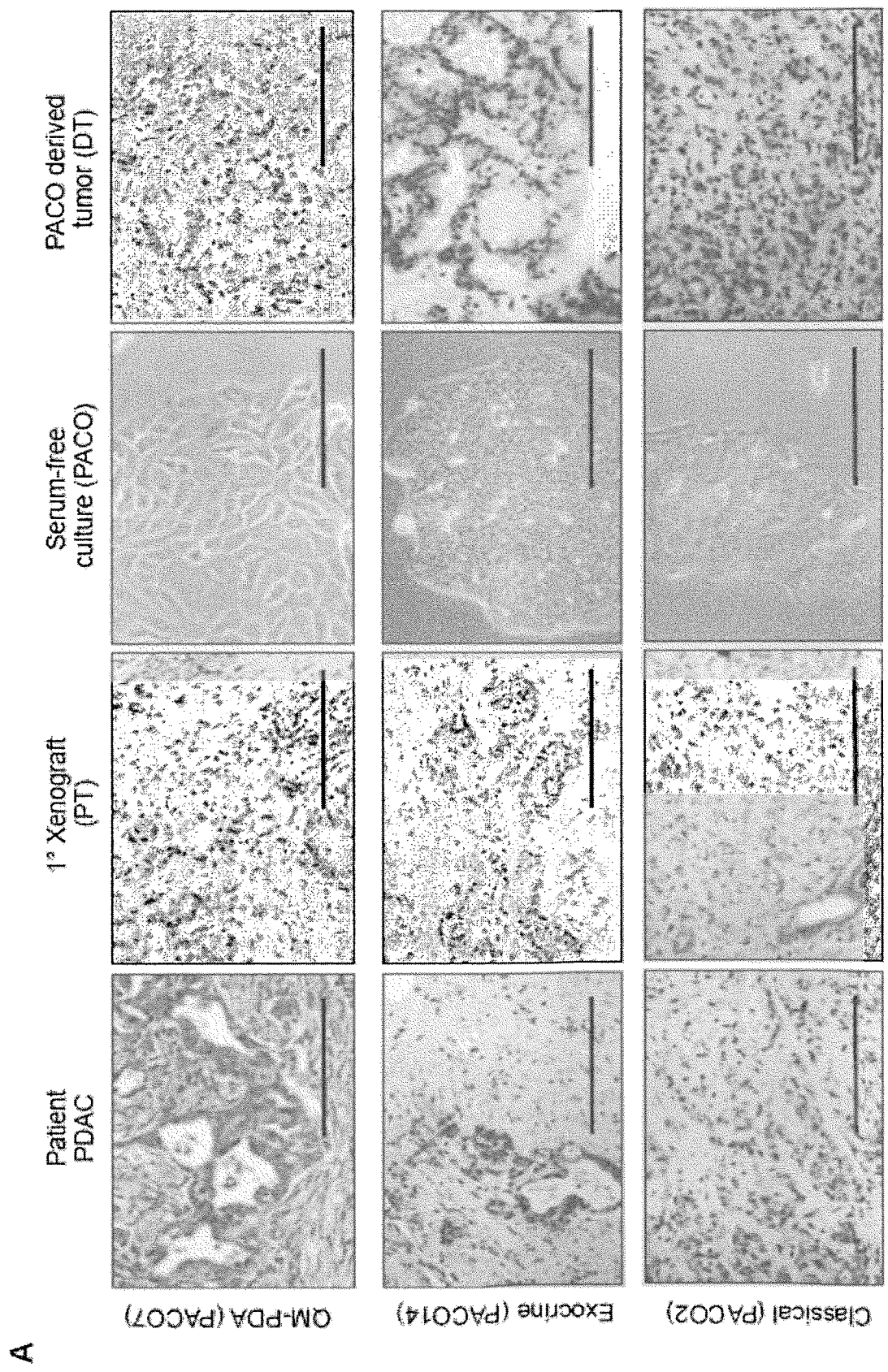

FIG. 8 shows the establishment of PDAC models representing all three described PDAC subtypes. (A) H&E staining of a primary human PDAC tumors, the corresponding xenografts (PT), bright field picture of the derived PACO cells and the respective PACO first passage derived tumors (DT) for the QM-PDA (PACO7), the exocrine-like (PACO14) and the classical (PACO2) subtype. Scale bar=100 μm. (B) Table summarizing PACO derived patient and tumor characteristics. (C) Table summarizing Pearson correlation analyses of log 2 gene expression data from PT versus DT xenografts, early versus late passages of the PACO lines, and DT versus PACO lines (****p<10-3).

FIG. 9 shows the identification and prognostic value of a novel two-marker set for PDAC subtypes. (A) Overview of the markers tested for subtype specificity. Markers were tested on slides representing all PDAC subtypes and scored for staining by a pathologist. (B) Table summarizing marker expression and subsequent subtype stratification of primary xenografts (PT), PACO cell lines and PACO derived xenografts (DT), as defined by a pathologist. (C) Table summarizing descriptive statistics of the tissue microarray containing 251 primary PDAC patients.

FIG. 10 shows that PDAC subtypes show differences in drug sensitivity. (A) Scatter plots showing relative cell viability [%] in response to 1 μM gemcitabine (upper part only), erlotinib and dasatinib, respectively. Each dot represents an individual PACO line. Horizontal bars depict mean±SEM (*p=0.05, One-Way ANOVA, Bonferroni correction); upper part: after 48 hours, lower part: after 7 days. (B) Gene Set Enrichment Analysis (GSEA) plots of the PACO lines, (C) of the PT+DT xenografts and (D) of the. Collisson et al gene dataset, using the drug metabolism gene signatures indicated (Collisson et al., 2011). Data represent enrichment of the exocrine-like subtype versus the rest. ES, Enrichment Score; NES, Normalized Enrichment Score; FDR, False Discovery Rate.

FIG. 11 shows the subtype-specific expression and induction of CYP3A5 in vitro and in vivo. (A-D) mRNA expression of CYP3A4 (top panel) and CYP3A7 (bottom panel) in PACO lines (A, C) and PACO derived xenografts (DT) (B, D) compared to normal pancreas and liver. Shown values are relative to normal pancreas mRNA expression. n.d.=not detected. Values are ±SEM (n=3). (E) Anti-CYP3A5 immunoblot of GST tagged recombinant CYP3A4, CYP3A5 and CYP3A7 protein at three different concentrations (0.5 μg, 1 μg, 3 μg) as indicated. Anti-GST was used as loading control. (F) Percentage of CYP3A5 positive and negative tumors as calculated for the parameters indicated, including PDAC subtypes, by immunohistochemical staining of the TMA. Significance was calculated with the Log-rank (Mantel-Cox) test. (G) Cox proportional hazards multivariate analysis revealed age at diagnosis, lymph node status, and CYP3A5 expression defined by immunohistochemistry as independent predictors for PDAC patient survival. (H) Pearson chi-squared test was used to determine independence of CYP3A5 expression from gender amongst all samples and also only the exocrine-like PDAC patient samples. (I) Anti-CYP3A5 immunoblot of CYP3A5 expression at basal level and in response to 10 μM dasatinib, erlotinib and gemcitabine in PACO cells of the classical (PACO2), the exocrine-like (PACO10, PACO14) and the QM-PDA (PACO9) subtype. GST tagged recombinant CYP3A5 was used as positive control and vinculin was used as loading control. (J) mRNA expression of CYP3A4 (top panel) and CYP3A7 (bottom panel) at the basal level and in response to 10 μM dasatinib, erlotinib and gemcitabine in PACO cells of the classical (PACO2), the exocrine-like (PACO10, PACO14) and the QM-PDA (PACO9) subtype. n.d.=not detected. Values are mean±SEM (n=3).

Figure 12:
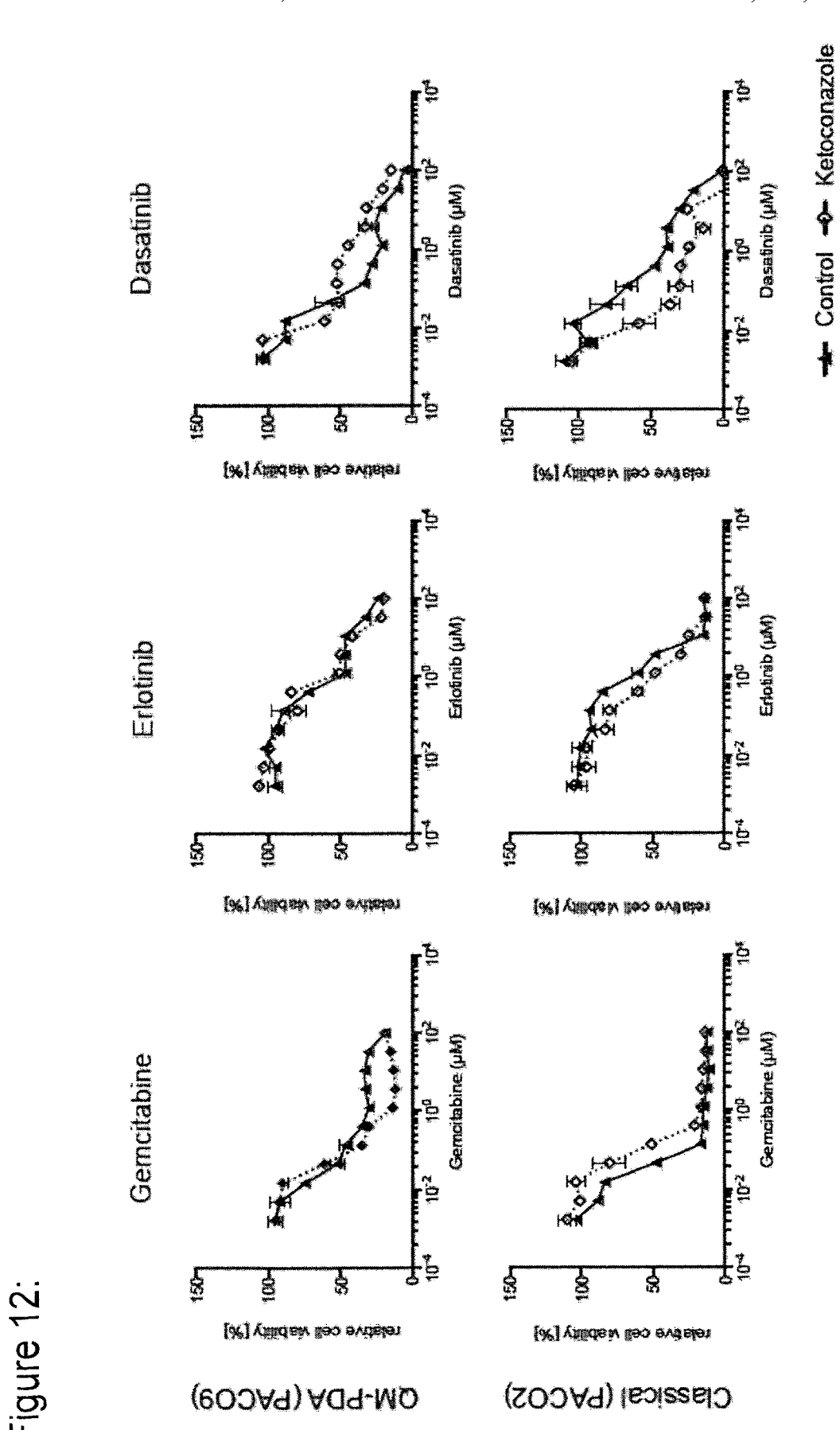

FIG. 12 shows that pan-cytochrome P450 inhibition sensitizes exocrine-like PDAC cells. Representative dose response curves for PACO cells (QM-PDA (PACO9), classical (PACO2)) pre-treated with 100 nM ketoconazole or vehicle for 2 hours, followed by the addition of gemcitabine, erlotinib or dasatinib at the indicated concentrations. Relative cell viability [%] was determined 48 hours post drug treatment (n=3).

FIG. 13 shows that the inactivation of erlotinib and dasatinib by CYP3A5 mediates drug resistance in the exocrine-like PDAC subtype. (A) mRNA expression of CYP3A5 comparing non-targeting (NT) to CYP3A5 (siRNA) siRNA transfected exocrine-like PACO cells (PACO10), using a pool of four or single siRNAs (siRNA1, 2, 3, 4). Values are mean±SEM (n=3). (B) Anti-CYP3A5 immunoblot of non-targeting (NT) and CYP3A5 (pool, si1-4) siRNA transfected exocrine-like PACO cells (PACO10), using a pool of four or single siRNAs (siRNA1, 2, 3, 4). Vinculin was used as loading control. (C) Representative dose response curves of single CYP3A5 (siRNA1 and 2) or non-targeting (NT) siRNA transfected exocrine-like PACO cells (PACO10) in response to serial dilutions of gemcitabine, erlotinib and dasatinib. Relative cell viability [%] was determined 48 hours after drug treatment (n=1). (D)

Erlotinib and dasatinib concentrations [µg/L] in the supernatant of two exocrine-like PACO cell lines (PACO14, PACO18) transfected with CYP3A5 (siRNA) or non-targeting (NT) siRNA and treated with 1 µM erlotinib (left panel) or dasatinib (right panel). Shown are compound concentrations of supernatants collected at the indicated timepoints. Values were calculated by mass spectrometric analysis (LC-MS/MS) (n=3; *p<0.05; Two-Way ANOVA, Bonferroni correction).

FIG. 14 shows that CYP3A5 mediates drug resistance in exocrine-like PDAC cells (A, B) Representative dose response curves of CYP3A5 or non-targeting (NT–control) siRNA transfected exocrine-like (PACO10, PACO18, PACO14), classical (PACO2) and QM-PDA (PACO9) cells, in response to serial dilutions of gemcitabine, erlotinib or dasatinib. Relative cell viability [%] was determined 48 hours after drug treatment (n=3). (C) Activity area values for CYP3A5 or non-targeting (NT–control) siRNA transfected classical (PACO2) and QM-PDA (PACO9) cells, in response to serial dilutions of the indicated drugs for 48 hours. Each dot represents one biological replicate. Horizontal bars depict mean±SEM (n=3; paired t-Test) (D) Representative dose response curves for shCYP3A5_1 and shCYP3A5_2 or shScr exocrine-like PACO lines (PACO10 and 14) treated with gemcitabine, erlotinib or dasatinib at the indicated concentrations. Relative cell viability [%] was determined 48 hours after drug treatment (n=2). (E) Representative dose response curves for siRNA_1 and siRNA_2 exocrine-like cell line PACO10 treated with erlotinib or dasatinib at the indicated concentrations. Relative cell viability [%] was determined 48 hours after drug treatment.

Figure 15:
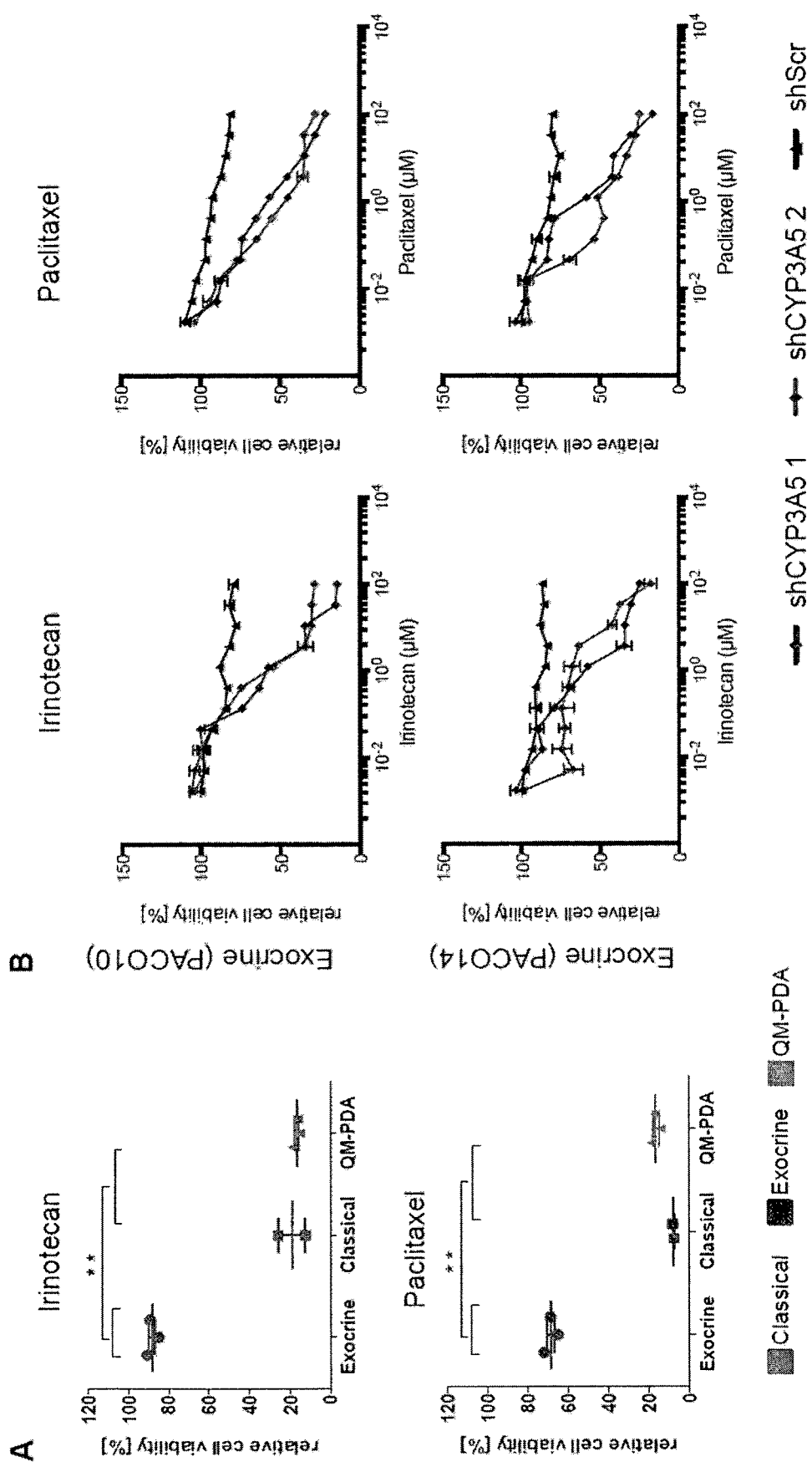

FIG. 15 shows that CYP3A5 has a broad implication in mediating drug resistance. (A) Scatter plots showing relative cell viability [%] in response to 10 µM irinotecan and paclitaxel after 48 h. Each dot represents an individual PACO cell line. Horizontal bars depict mean±SEM (n=2; ***p=0.001; grouped One-Way ANOVA, Bonferroni correction). (B) Dose response curves for shCYP3A5_1, shCYP3A5_2 and shScr exocrine-like PACO lines (PACO10, PACO14) treated with irinotecan or paclitaxel at the indicated concentrations. Relative cell viability [%] was determined 48 hours after drug treatment. Shown is one representative experiment out of three. (C) Representative CYP3A5 staining of human paraffin sections of nine different tumor entities from a tissue microarray containing 438 samples. Scale bar=100 µm. (D) Tables summarizing percentage of CYP3A5 positive patient samples per tumor entity: ++ strong staining; + weak staining; +/− unspecific staining; − no staining.

Figure 16:
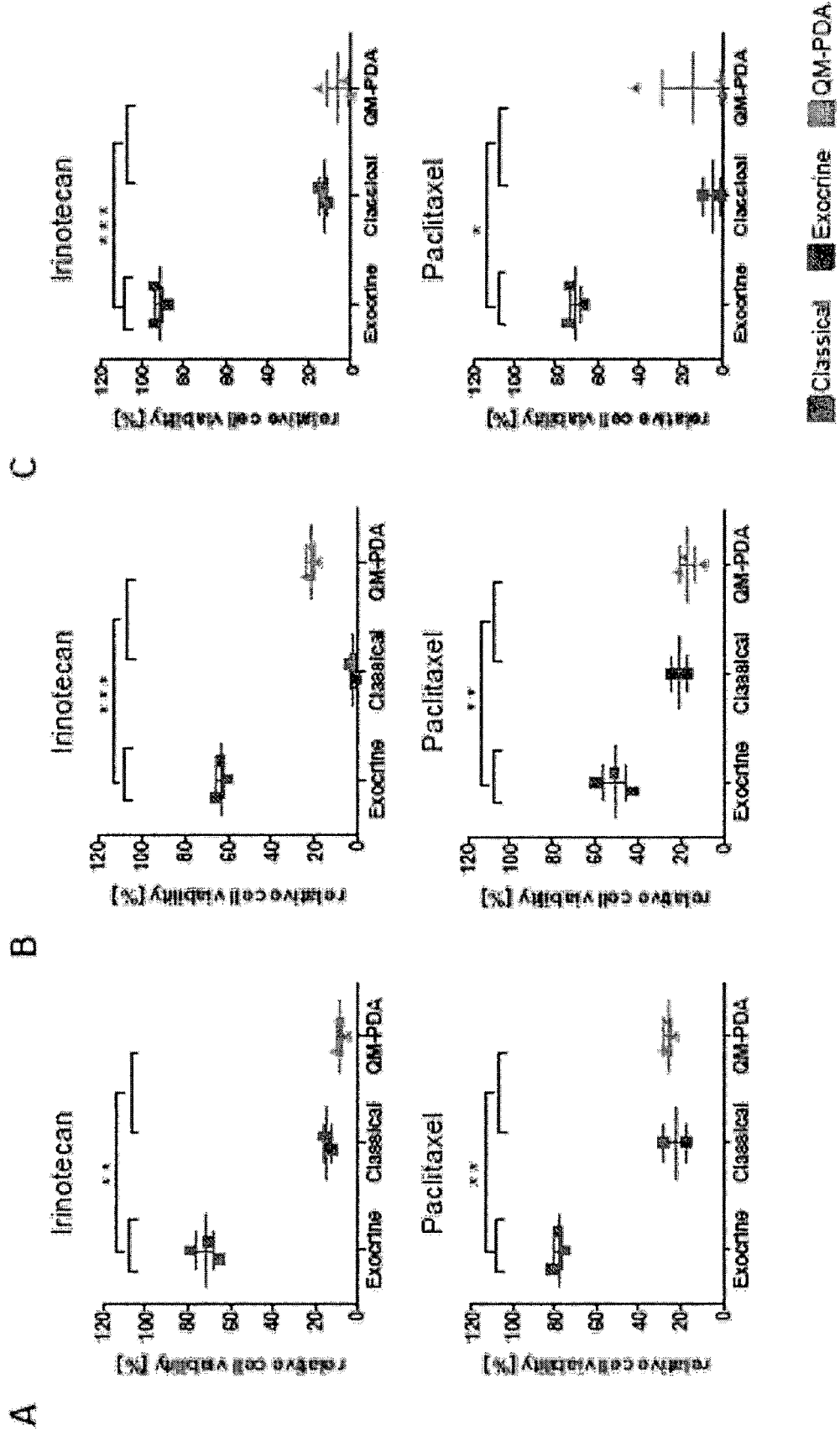

FIG. 16 shows additional data demonstrating that PDAC subtypes show differences in drug sensitivity to paclitaxel and irinotecan. (A-C) Scatter plots showing relative cell viability [%] in response to 10 µM irinotecan or paclitaxel, respectively, after 48 hours (A) and in response to 1 µM (B) and 10 µM (C) irinotecan or paclitaxel after 7 days. Each dot represents an individual PACO line. Horizontal bars depict mean±SEM (***p=0.001, grouped One-Way ANOVA, Bonferroni correction).

FIG. 17 shows the drug-sensitivity profiles and CYP3A-family member expression of drug-resistant cell lines. (A) Classical (PACO2) and QM-PDA (PACO7) cell lines that were treated for eight weeks with increasing concentrations of either erlotinib, dasatininb or paclitaxel show increased resistance to the respective drugs and (B) elevated expression of CYP3A5 but not CYP3A4 or CYP3A7, as determined by qRT-PCR.

FIG. 18 shows an increase in CYP3A5 expression after paclitaxel treatment in vivo. (A) Growth curve of xenograft tumors of the classical subtype in mice treated with paclitaxel or control vehicle, respectively. (B) Tumors derived from paclitaxel treated mice show an increased expression of CYP3A5, but not CYP3A4 or CYP3A7 as determined by qRT-PCR and (C) immunohistochemistry.

FIG. 19 shows the effect of siRNA-mediated knockdown of CYP3A5 on paclitaxel-sensitivity in drug-resistant non-exocrine cells. (A) Efficiency of the siRNA-mediated knockdown of CYP3A5 in PACO2 and PACO7 paclitaxel-resistant cell lines. (B) Knockdown of CYP3A5 sensitizes the paclitaxel resistant classical (PACO2PR) and QM-PDA (PACO7PR) cell lines. (C) Inhibition of CYP-activity by the pan-CYP inhibitor ketoconazole similarly sensitizes the paclitaxel-resistant cell lines PACO2PR and PACO7PR.

FIG. 20 shows that CYP3A5 mediates paclitaxel resistance in hepatocellular carcinoma. (A-C) The hepatocellular carcinoma cell line HepG2 expresses CYP3A5 at levels comparable to some exocrine PDAC cell lines and normal liver, but not CYP3A4 and CYP3A7 as determined by qRT-PCR. (D) CYP3A5 expression can be suppressed by siRNA-mediated knockdown in HepG2 cell. (E, F) Knockdown of CYP3A5 (E), or ketoconazole-mediated suppression of CYP activity (F), sensitizes HepG2 cells to paclitaxel treatment.

FIG. 21 shows that CYP3A5 is expressed in gastric cancers and that inhibition of CYP-activity sensitizes gastric cancer cells to paclitaxel treatment. (A) CYP3A5, CYP3A4 but not CYP3A7 are expressed in the gastric cancer line SNU5. (B) Inhibition of CYP-activity by ketoconazole sensitized gastric cancer cells to paclitaxel.

DETAILED DESCRIPTION OF THE INVENTION

The present invention may be understood more readily by reference to the following detailed description of the invention and the examples included therein.

In one aspect, the present invention relates to an in vitro method for the characterization of the metabolic status of tumor cells characterized by the step of measuring expression of cytochrome P450 3A5 (CYP3A5) in said tumor cells.

The present inventors surprisingly identified that certain cancer cells show an increased expression of cytochrome P450 3A5 (CYP3A5). In normal tissue, cytochromes such as cytochrome P450 3A5 (CYP3A5), which previously has been implicated in systemic drug metabolism, are usually only expressed in liver cells, while only minor amounts of these enzymes are expressed in other tissue types (Ding and Kaminsky, 2003; Pavek and Dvorak, 2008).

Kivistö et al. (1996) showed that CYP3A5 is the major enzyme of the CYP3A subfamily present at the mRNA level in both normal human lung and lung tumors, but reported that it remained unclear whether it was functionally active. As reported in Plummer et al., 2003, CYP3A5 is expressed in between about 10 and 30% of adult livers (14, 15, 16), but the expression pattern appears to be rather complex since there are several polymorphic variants that appear to have a functional effect on CYP3A5 activity. Downie et al. (2005) demonstrated that CYP3A5 was overexpressed in primary ovarian cancers. Castell et al. (2005) reported that CYP3A5 was widely expressed in lung tissues. Leclerc et al. (2010) analyzed the gene expression of the cytochrome P450 superfamily in human bronchial and peripheral lung tissues and found that CYP3A5 appeared to be expressed in pulmonary parenchyma, but not in bronchial mucosa. Maguire et al.

(2012) showed an increased expression of CYP3A5 in prostate cancer and suggested to stimulate expression of CYP3A5 to increase androgen-inactivation in castrate-resistant tumors. In summary, no clear picture is yet available about the expression of CYP3A5 in cells and tissues of healthy individuals or in patients suffering from cancer, the polymorphic nature of the expression products and/or about the functionality of CYP3A5 expression products.

Sensitivity to therapeutic agents may inter alia depend on drug metabolism, since drugs can be systemically inactivated by xenobiotic biotransformation (Nebert and Dalton, 2006). This mechanism can be divided into functionalization (phase I) and conjugation (phase II). Phase I is mediated by members of the cytochrome P450 (CYP) enzyme family, which increase metabolite reactivity by oxidation. During phase II, which is mainly facilitated by the uridine 5'-diphospho-glucuronosyltransferase (UGT) enzyme family members, the substrates are chemically conjugated, thus becoming more hydrophilic, allowing metabolite excretion (Nebert and Dalton, 2006). CYPs can be divided into those that metabolize endogenous molecules such as hormones, and into the once that process exogenous molecules such as drugs. Both classes offer potential targets for treatment (Bruno and Njar, 2007). Currently, studies of these enzymes are focused on their impact on systemic drug metabolism (Sanchez and Kauffman, 2010). Previous studies on the expression of CYP family members in various cancers have shown contradicting results (Michael and Doherty, 2005). Functionally, CYP17A1, which catalyzes the final steps of testosterone synthesis, was approved for treatment of prostate cancer (Bruno and Njar, 2007). In contrast, a functional demonstration that CYPs involved in exogenous metabolism contribute in cancer cells to drug resistance remains elusive (Bruno and Njar, 2007; Michael and Doherty, 2007). WO 03/057916 searched for correlations between gene expression and drug sensitivities of tumor cells and identified CYP3A5 as one potentially relevant gene for the detoxification and inactivation of anti-cancer drugs.

Thus, it was completely unexpected and surprising that RNA expression signatures could be identified that show an up-regulation of drug metabolism processes in the tumor cells, such as exocrine-like PDAC tumor cells. Thus, while the involvement of cytochromes in general in systemic drug metabolism, particularly in the liver, was of course known since long, the present invention for the first time identifies cytochrome P450 3A5 (CYP3A5) as playing a role in certain tumor cells in the tumor cells' defense mechanism, thus permitting novel approaches for diagnosis, patient stratification and treatment of cancer patients.

In certain embodiments, said tumor cells are selected from cells from a tumor selected from PDAC, particularly PDAC of the exocrine-like subtype; hepatocellular carcinoma, stomach adenocarcinoma, melanoma, and thyroid papillary carcinoma.

In the context of the present invention, the terms "tumor cells" and "cancer cells", or "tumor" and "cancer" are used interchangeably.

In one embodiment, said tumor cells are characterized as CYP3A5-positive tumor cells, when expression of CYP3A5 is at least two-fold higher than in a non-cancerous cells from the same tissue or cells of the same type, and as CYP3A5-negative cancer cell, when expression of CYP3A5 is less than two-fold higher than in non-cancerous cells from the same tissue or cells of the same type. In particular embodiments, tumor cells are characterized as CYP3A5-positive tumor cells, when expression of CYP3A5 is at least five-fold higher than in a non-cancerous cells from the same tissue or cells of the same type, in more particular embodiments, tumor cells are characterized as CYP3A5-positive tumor cells, when expression of CYP3A5 is at least ten-fold higher than in a non-cancerous cell from the same tissue or cells of the same type.

Expression of CYP3A5 in a sample can be determined by several methods. In the context of the present invention, a sample is considered CYP3A5-positive, if at least one of the following methods determines a sample as CYP3A5-positive.

In certain embodiments, the method of the present invention comprises the steps of: (a) determining the amount of cytochrome P450 3A5 (CYP3A5) mRNA in said tumor cells; and (b) determining the amount of cytochrome P450 3A5 (CYP3A5) mRNA in reference cells, wherein said reference cells are non-cancerous cells from the same tissue or cells of the same type.

Determination of CYP3A5 mRNA expression. In one embodiment, expression of CYP3A5 is the detection of a CYP3A5 or a CYP3A5-coding transcript in a sample compared to the corresponding presence in one or more comparator samples. The expression is considered at least two-fold higher when the normalized signal for the cancer cell containing sample divided by the normalized signal obtained from a non-cancerous cells from the same tissue or cells of the same type is $\geq 2$. Suitable methods include, but are not limited to, real-time quantitative PCR (q-RT-PCR), gene-expression profiling by gene-expression arrays or mRNA sequencing. Normalization of expression in a sample is achieved by dividing the signal obtained for CYP3A5 mRNA by the signal from one or the average of multiple mRNAs suitable for normalization of the specific sample. Examples of suitable mRNAs include, but are not limited to, PPIA and GAPDH.

In certain embodiments, the amount of cytochrome P450 3A5 (CYP3A5) mRNA is determined by quantitative real-time polymerase chain reaction (qRT-PCR).

In certain other embodiments, the method of the present invention comprises the steps of: (a) determining the presence of cytochrome P450 3A5 (CYP3A5) protein in said tumor cells; and (b) determining the presence of cytochrome P450 3A5 (CYP3A5) protein in reference cells, wherein said reference cells are non-cancerous cells from the same tissue or cells of the same type.

In certain embodiments, the presence of cytochrome P450 3A5 (CYP3A5) is determined by immunohistochemistry.

Determination of CYP3A5 protein expression can be performed by evaluation of the staining of cells. In the evaluation of the staining for subtype assignment. 500 tumor cells and 500 comparator cells from a non-cancerous sample from the same tissue or cells of the same type are evaluated in each specimen. All samples are reviewed by at least one pathologist, particularly independently by two pathologists, who is/are unaware of any clinical, seriological, or immunohistological findings, and who is/are blinded to the identity of the specimens. A signal is considered positive if the observed signal can be clearly distinguished from the background staining observed with an isotype control antibody on a comparable specimen. The specimen is considered positive for CYP3A5 if at least one tumor cell shows a clearly detectable intracellular signal. The expression is considered at least two-fold higher when the cancer cell containing sample shown at least the twofold number of CYP3A5-positive cells, when compared to the number of positive cells from a non-cancerous sample from the same tissue or cells of the same type.

In certain other embodiments, said tumor cells are characterized as CYP3A5-positive tumor cells, when expression of CYP3A5 is increased at least two-fold when said cells are contacted with a CYP3A5 substrate, in particular dasatinib, erlotinib, paclitaxel, or irinotecan, and as CYP3A5-negative cancer cell, when expression of CYP3A5 is increased less than two-fold when said cell is contacted with a CYP3A5 substrate, in particular dasatinib, erlotinib, paclitaxel, or irinotecan.

In certain other embodiments, the method of the present invention comprises the steps of: (a) contacting a first sample of said tumor cells with a CYP3A5 substrate, in particular dasatinib, erlotinib, paclitaxel, or irinotecan; (b) determining the amount of cytochrome P450 3A5 (CYP3A5) mRNA in said first sample of tumor cells; and (c) determining the amount of cytochrome P450 3A5 (CYP3A5) mRNA in a second sample of said tumor cells, wherein said second sample has not been contacted with said CYP3A5 substrate.

In certain embodiments, the amount of cytochrome P450 3A5 (CYP3A5) mRNA is determined by quantitative real-time polymerase chain reaction (qRT-PCR).

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components, or groups thereof. The term "comprising" thus includes the more restrictive terms "consisting of" and "consisting essentially of".

In certain embodiments, said tumor cells are cells from a tumor sample.

In certain embodiments, said sample is obtained from a mammal, particularly a human.

In certain embodiments, said tumor sample is from a patient suffering from cancer, particularly a cancer selected from: PDAC, particularly PDAC of the exocrine-like subtype; kidney carcinoma, particularly clear-cell carcinoma or kidney transitional cell carcinoma; ovarian cancer, particularly serous cystadenocarcinoma; uterine cervix adenocarcinoma; endometrium adenocarcinoma; rectum adenocarcinoma; colon adenoma; stomach carcinoma, particularly stomach adenocarcinoma; hepatocellular carcinoma; thyroid papillary carcinoma; adrenal gland cortical carcinoma; melanoma; and melanoma metastasis to lymph node.

In certain other embodiments, said tumor sample is from a patient that currently is, or has already been, under treatment of cancer with a therapeutically active substance, particularly wherein said cancer is recurring, refractory, and/or resistant to said therapeutically active substance. In particular embodiments, said patient that has been CYP3A5-negative at the beginning of said treatment.

In certain embodiments, said tumor sample is from PDAC, particularly PDAC of the exocrine-like subtype.

In certain other embodiments, said tumor sample is from a PDAC patient that currently is, or has already been, under treatment with a therapeutically active substance, particularly wherein said tumor is recurring, refractory, and/or resistant to said therapeutically active substance, particularly a PDAC patient that has been CYP3A5-negative at the beginning of said treatment.

In a particular embodiment, the sample to be tested contains pancreatic tissue.

In the context of the present invention, "PDAC" refers to pancreatic ductal adenocarcinoma, the most common type of pancreatic cancer, accounting for 95% of these tumors, arising within the exocrine component of the pancreas. It is typically characterized by moderately to poorly differentiated glandular structures on microscopic examination.

In the context of the present invention, "pancreatic cancer" refers to a cancer originating from transformed cells arising in tissues forming the pancreas.

In the context of the present invention, the terms "classical", "quasi-mesenchymal", and "exocrine-like subtype of PDAC" refer to the PDAC subtypes as identified by Collisson et al. (loc. cit.) based on their gene expression profiles. In this study, a 62-gene panel was devised that enables classification of tumor samples into one of the three subtypes. Furthermore, WO 2014/056626 provides a marker-based approach for identifying PDAC subtypes.

The exocrine-like PDAC subtype gives rise to tumors with a differentiated growth pattern of medium-sized neoplastic duct-structures with only moderate variation in nuclear size and chromatin structure.

In particular embodiments, the tumor sample is from a patient suffering from cancer selected from hepatocellular carcinoma, melanoma, thyroid papillary carcinoma, rectum adenocarcinoma, colon adenoma, and stomach carcinoma, particularly stomach adenocarcinoma; more particularly selected from hepatocellular carcinoma, melanoma, and stomach carcinoma, particularly stomach adenocarcinoma.

In certain such embodiments, said tumor sample is from a patient that currently is, or has already been, under treatment with a therapeutically active substance, particularly wherein said tumor is recurring, refractory, and/or resistant to said therapeutically active substance, particularly a PDAC patient that has been CYP3A5-negative at the beginning of said treatment.

In another aspect, the present invention relates to a method of stratifying (i) a patient suffering from cancer, particularly a cancer selected from: PDAC, particularly PDAC of the exocrine-like subtype; kidney carcinoma, particularly clear-cell carcinoma or kidney transitional cell carcinoma; ovarian cancer, particularly serous cystadenocarcinoma; uterine cervix adenocarcinoma; endometrium adenocarcinoma; rectum adenocarcinoma; colon adenoma; stomach carcinoma, particularly stomach adenocarcinoma; hepatocellular carcinoma; thyroid papillary carcinoma; adrenal gland cortical carcinoma; melanoma; and melanoma metastasis to lymph node, or (ii) a patient that is already, or has been, under treatment of cancer with a therapeutically active substance, particularly wherein said cancer is recurring, refractory, and/or resistant to said therapeutically active substance; into a treatment cohort, the method comprising the steps of (a) in vitro measuring expression of cytochrome P450 3A5 (CYP3A5) in tumor cells obtained from said patient; (b) determining the metabolic status of said tumor cells as either CYP3A5-positive or CYP3A5-negative; and (c) stratifying said patient into a drug treatment cohort based on the metabolic status determined in step (b).

In the context of the present invention, the term "stratifying" or "stratification" relates to the identification of a group of patients with shared "biological" characteristics by using molecular and biochemical diagnostic testing to select the optimal management for the patients.

In certain embodiments, the expression of cytochrome P450 3A5 (CYP3A5) is determined on the protein level by immunohistochemistry.

In certain embodiments, the expression of cytochrome P450 3A5 (CYP3A5) is determined on the mRNA level by quantitative real-time polymerase chain reaction (q RT-PCR).

In certain embodiments, said tumor cells are obtained by purifying tumor cells from a tumor sample from said patient, particularly wherein the purification comprises flow sorting or laser capture microdissection.

In a particular embodiment, the patient sample is selected from blood, serum, and plasma. In a particular embodiment, the patient sample is a collection of circulating tumor cells (CTCs), particularly isolated from the blood of a patient. In particular embodiments, the CTCs are isolated by apheresis.

In certain embodiments, said tumor cells are, or have been, (i) isolated from the blood of said patient; or (ii) isolated from a tumor sample, which is a tumor biopsy.

In certain embodiments, said tumor biopsy is, or has been, obtained by fine needle aspiration.

In a particular embodiment, the patient sample is selected from blood, serum, and plasma. In a particular embodiment, the patient sample is a collection of circulating tumor cells (CTCs), particularly isolated from the blood of a patient. In particular embodiments, the CTCs are, or have been, isolated by apheresis.

In particular embodiments, said tumor cells are selected from cells from a tumor selected from PDAC, particularly PDAC of the exocrine-like subtype; hepatocellular carcinoma, stomach adenocarcinoma, melanoma, and thyroid papillary carcinoma.

In particular embodiments, the patient sample originates from a resectable PDAC.

In another aspect, the present invention relates to an inhibitor of cytochrome P450 3A5 (CYP3A5), particularly a specific inhibitor of cytochrome P450 3A5 (CYP3A5), for use in the treatment of cancer, particularly a cancer comprising CYP3A5-positive cancer cells, particularly of PDAC, particularly PDAC of the exocrine-like subtype.

In another aspect, the present invention relates to a method for the treatment of cancer, particularly a cancer selected from: PDAC, particularly PDAC of the exocrine-like subtype; kidney carcinoma, particularly clear-cell carcinoma or kidney transitional cell carcinoma; ovarian cancer, particularly serous cystadenocarcinoma; uterine cervix adenocarcinoma; endometrium adenocarcinoma; rectum adenocarcinoma; colon adenoma; stomach carcinoma, particularly stomach adenocarcinoma; hepatocellular carcinoma; thyroid papillary carcinoma; adrenal gland cortical carcinoma; melanoma; and melanoma metastasis to lymph node; particularly a cancer comprising CYP3A5-positive cancer cells, particularly of PDAC, particularly PDAC of the exocrine-like subtype comprising the step of administering an inhibitor of cytochrome P450 3A5 (CYP3A5), particularly a specific inhibitor of cytochrome P450 3A5 (CYP3A5) to a patient in need thereof.

In certain embodiments, the present invention relates to a method for the treatment of cancer in a patient that is already, or has been, under treatment of cancer with a therapeutically active substance, particularly wherein said cancer is recurring, refractory, and/or resistant to said therapeutically active substance. In particular embodiments, said patient that has been CYP3A5-negative at the beginning of said treatment.

In another aspect, the present invention relates to a drug combination of (i) an inhibitor of cytochrome P450 3A5 (CYP3A5), particularly a specific inhibitor of cytochrome P450 3A5 (CYP3A5), and (ii) one or more additional therapeutic agents, for use in the treatment of cancer, particularly a cancer selected from: PDAC, particularly PDAC of the exocrine-like subtype; kidney carcinoma, particularly clear-cell carcinoma or kidney transitional cell carcinoma; ovarian cancer, particularly serous cystadenocarcinoma; uterine cervix adenocarcinoma; endometrium adenocarcinoma; rectum adenocarcinoma; colon adenoma; stomach carcinoma, particularly stomach adenocarcinoma; hepatocellular carcinoma; thyroid papillary carcinoma; adrenal gland cortical carcinoma; melanoma; and melanoma metastasis to lymph node. In particular embodiments, said cancer is a cancer comprising CYP3A5-positive cancer cells, particularly of PDAC, particularly PDAC of the exocrine-like subtype. In particular embodiments, the patient suffering from cancer is already, or has been, under treatment of cancer with a therapeutically active substance, particularly wherein said cancer is recurring, refractory, and/or resistant to said therapeutically active substance. In particular embodiments, said patient that has been CYP3A5-negative at the beginning of said treatment.

In another aspect, the present invention relates to a method for the combination treatment of cancer, particularly a cancer selected from: PDAC, particularly PDAC of the, exocrine-like subtype; kidney carcinoma, particularly clear-cell carcinoma or kidney transitional cell carcinoma; ovarian cancer, particularly serous cystadenocarcinoma; uterine cervix adenocarcinoma; endometrium adenocarcinoma; rectum adenocarcinoma; colon adenoma; stomach carcinoma, particularly stomach adenocarcinoma; hepatocellular carcinoma; thyroid papillary carcinoma; adrenal gland cortical carcinoma; melanoma; and melanoma metastasis to lymph node; particularly of PDAC of the exocrine-like subtype, comprising the step of administering an inhibitor of cytochrome P450 3A5 (CYP3A5), particularly a specific inhibitor of cytochrome P450 3A5 (CYP3A5), in combination with one or more additional therapeutic agents for use in the treatment of said cancer to a patient in need thereof. In particular embodiments, the patient suffering from cancer is already, or has been, under treatment of cancer with a therapeutically active substance, particularly wherein said cancer is recurring, refractory, and/or resistant to said therapeutically active substance. In particular embodiments, said patient that has been CYP3A5-negative at the beginning of said treatment.

In the context of the present invention, the term "inhibitor of cytochrome P450 3A5 (CYP3A5)" refers to a compound that inhibits the activity of cytochrome P450 3A5 (CYP3A5) in an in vitro experiment with an $IC_{50}$ value of $10^{-6}$ M or less, particularly of $10^{-7}$ M or less, more particularly of $10^{-8}$ M or less, and most particularly of $10^{-9}$ M or less. Examples of inhibitors of cytochrome P450 3A5 (CYP3A5) include ketoconazole, clarithromycin, indinavir, itraconazole, nefazodone, ritonavir, saquinavir, suboxone, and telithromycin.

In the context of the present invention, the term "specific inhibitor of cytochrome P450 3A5 (CYP3A5)" refers to a compound that inhibits the activity of cytochrome P450 3A5 (CYP3A5) in an in vitro experiment with an $IC_{50}$ value that is by a factor of at least 5, particularly a factor of at least 10, more particularly a factor of at least 20 lower than the $IC_{50}$ value for inhibition of each cytochrome P450 taken from the list of CYP3A4, and CYP3A7.

In certain embodiments, the specific inhibitor of cytochrome P450 3A5 (CYP3A5) is an siRNA molecule or an shRNA molecule, particularly an shRNA molecule.

In the context of the present invention, the term "siRNA" refers to small or short) interfering RNA molecules, which are a class of double-stranded RNA molecules having between 20 and 30, particularly between 20 and 25 base pairs in length. siRNA molecules interfere with the expression of the mRNA of genes with complementary nucleotide sequences and cause that mRNA to be cleaved after transcription resulting in no translation.

In the context of the present invention, the term "shRNA" refers to small RNA-based molecules comprising sequences that form a small (or short) hairpin. Such shRNA sequence can be used to silence target gene expression via RNA interference (RNAi). Expression of shRNA in cells is typically accomplished by delivery of plasmids or through viral or bacterial vectors.

In certain embodiments, said one or more additional therapeutic agents are one or more chemotherapeutic agents, particularly one or more chemotherapeutic agents selected from (i) a tyrosine kinase inhibitor, particularly (ia) a Src inhibitor, particularly a Src inhibitor selected from bosutinib, dasatinib (in any approved and/or commercially available form, including, but not limited to, Sprycel®), ponatinib and saracatinib, particularly dasatinib, and/or (ib) an EGF receptor inhibitor, particularly an EGF receptor inhibitor selected from erlotinib (in any approved and/or commercially available form, including, but not limited to, Tarceva®), gefitinib, afatinib, vandetanib, lapatinib, AZD9291, neratinib, pelitinib, dacomitinib, canertinib, icotinib, and varlitinib, particularly erlotinib, (ii) gemcitabine (in any approved and/or commercially available form, including, but not limited to, Gemzar®), (iii) irinotecan; and (iv) a taxane, particularly a taxane selected from paclitaxel (in any approved and/or commercially available form, including, but not limited to, taxol and nab-paclitaxel) and docetaxel (in any approved and/or commercially available form, including, but not limited to, Taxotere®).

In the context of the present invention, "Src" relates to a protein (also called c-Src for "cellular Src"), which is a tyrosine kinase encoded by the proto-oncogene SRC, which is frequently overexpressed and highly activated in malignancies. Src is a member of a kinase family (the so-called "Src family"). Additional members of that family are: Lyn, Fyn, Lck, Hck, Fgr, Blk, Yrk and c-Yes.

In the context of the present invention, "EGF receptor" relates to a receptor tyrosine kinases protein (also called EGFR; ErbB-1; or particularly HER1 in humans), which is a cell-surface receptor for members of the epidermal growth factor family (EGF family) of extracellular protein ligands.

In certain embodiments, the treatment is the treatment of a patient suffering from cancer, particularly a cancer comprising CYP3A5-positive cancer cells, particularly a cancer selected from: PDAC, particularly PDAC of the exocrine-like subtype; kidney carcinoma, particularly clear-cell carcinoma or kidney transitional cell carcinoma; ovarian cancer, particularly serous cystadenocarcinoma; uterine cervix adenocarcinoma; endometrium adenocarcinoma; rectum adenocarcinoma; colon adenoma; stomach carcinoma, particularly stomach adenocarcinoma; hepatocellular carcinoma; thyroid papillary carcinoma; adrenal gland cortical carcinoma; melanoma; and melanoma metastasis to lymph node. In particular embodiments, the cancer is selected from PDAC, particularly PDAC of the exocrine-like subtype; hepatocellular carcinoma, melanoma, thyroid papillary carcinoma, rectum adenocarcinoma, colon adenoma, and stomach carcinoma, particularly stomach adenocarcinoma; more particularly selected from PDAC, particularly PDAC of the exocrine-like subtype; hepatocellular carcinoma, melanoma, and stomach carcinoma, particularly stomach adenocarcinoma. In particular embodiments, the patient suffering from cancer is already, or has been, under treatment of cancer with a therapeutically active substance, particularly wherein said cancer is recurring, refractory, and/or resistant to said therapeutically active substance. In particular embodiments, said patient that has been CYP3A5-negative at the beginning of said treatment.

In certain embodiments, the treatment is the selected from: the treatment of PDAC, particularly PDAC of the exocrine-like subtype; the treatment of stomach adenocarcinoma; and the treatment of hepatocellular carcinoma; in particular the treatment of PDAC of the exocrine-like subtype.

In certain embodiments, the drug combination comprises (i) at least one Src inhibitor selected from bosutinib, dasatinib (in any approved and/or commercially available form, including, but not limited to, Sprycel®), ponatinib and saracatinib, particularly dasatinib, (ii) at least one EGF receptor inhibitor selected from Erlotinib (in any approved and/or commercially available form, including, but not limited to, Tarceva®), gefitinib, afatinib, vandetanib, lapatinib, AZD9291, neratinib, pelitinib, dacomitinib, canertinib, icotinib, and varlitinib, particularly erlotinib; (iii) irinotecan; and/or (iv) a taxane, particularly a taxane selected from paclitaxel (in any approved and/or commercially available form, including, but not limited to, taxol and nab-paclitaxel) and docetaxel (in any approved and/or commercially available form, including, but not limited to, Taxotere®). In particular embodiments, the drug combination comprises two compounds selected from (i) to (iv), in particular irinotecan and paclitaxel.

In the context of the present invention, the term "specific expression" refers to the detection of a protein or a transcript in a sample compared to one or more comparator samples. The expression of an investigated marker is considered specific to a sample if of 500 analyzed tumor cells at least one tumor cell shows a signal above that observed with an unspecific control antibody and in the comparator sample or comparator samples no positive signal for the investigated marker can be detected. In particular embodiments, the expression of an investigated marker is considered specific to a sample if of 500 analyzed tumor cells at least two, more particularly at least five, tumor cells show a signal above that observed with an unspecific control antibody.

In particular embodiments, said sample is, or has been, obtained from a mammal, particularly a human.

In a particular embodiment, the patient sample is selected from blood, serum, and plasma. In a particular embodiment, the patient sample is a collection of circulating tumor cells (CTCs), particularly isolated from the blood of a patient. In particular embodiments, the CTCs are, or have been, isolated by apheresis.

In particular embodiments, the patient sample originates from a resectable PDAC.

In another aspect, the present invention relates to a drug combination of (i) an inhibitor of cytochrome P450 3A5 (CYP3A5), particularly a specific inhibitor of cytochrome P450 3A5 (CYP3A5), and (ii) one or more additional therapeutic agents, wherein at least one of said additional therapeutic agents is a substrate for cytochrome P450 3A5 (CYP3A5), for use in the treatment of a patient suffering from cancer, particularly a cancer comprising CYP3A5-positive cancer cells, particularly a cancer selected from: PDAC, particularly PDAC of the exocrine-like subtype; kidney carcinoma, particularly clear-cell carcinoma or kidney transitional cell carcinoma; ovarian cancer, particularly serous cystadenocarcinoma; uterine cervix adenocarcinoma; endometrium adenocarcinoma; rectum adenocarcinoma; colon adenoma; stomach carcinoma, particularly stomach adenocarcinoma; hepatocellular carcinoma; thyroid papillary carcinoma; adrenal gland cortical carcinoma; melanoma; and melanoma metastasis to lymph node. In particular embodiments, the cancer is selected from PDAC, particularly PDAC of the exocrine-like subtype; hepatocellular carcinoma, melanoma, thyroid papillary carcinoma, rectum adenocarcinoma, colon adenoma, and stomach carcinoma, particularly stomach adenocarcinoma, more particularly selected from. PDAC, particularly PDAC of the exocrine-like subtype; hepatocellular carcinoma, stomach adenocarcinoma, melanoma, and thyroid papillary carcinoma; more particularly selected from PDAC, particularly PDAC of the exocrine-like subtype; hepatocellular carcinoma, stomach adenocarcinoma and melanoma. Most particularly the cancer is PDAC, particularly PDAC of the exocrine-like subtype. In particular embodiments, the patient suffering from cancer is already, or has been, under treatment of cancer with a therapeutically active substance, particularly wherein said cancer is recurring, refractory, and/or resistant to said therapeutically active substance. In particular embodiments, said patient that has been CYP3A5-negative at the beginning of said treatment.

In another aspect, the present invention relates to a method for the treatment of a patient suffering from cancer, particularly a cancer comprising CYP3A5-positive cancer cells, particularly a cancer selected from: PDAC, particularly PDAC of the exocrine-like subtype; kidney carcinoma, particularly clear-cell carcinoma or kidney transitional cell carcinoma; ovarian cancer, particularly serous cystadenocarcinoma; uterine cervix adenocarcinoma; endometrium adenocarcinoma; rectum adenocarcinoma; colon adenoma; stomach carcinoma, particularly stomach adenocarcinoma; hepatocellular carcinoma; thyroid papillary carcinoma; adrenal gland cortical carcinoma; melanoma; and melanoma metastasis to lymph node; comprising the step of administering an inhibitor of cytochrome P450 3A5 (CYP3A5), particularly a specific inhibitor of cytochrome P450 3A5 (CYP3A5), in combination with one or more additional therapeutic agents wherein at least one of said additional therapeutic agents is a substrate for cytochrome P450 3A5 (CYP3A5). In particular embodiments, the patient suffering from cancer is already, or has been, under treatment of cancer with a therapeutically active substance, particularly wherein said cancer is recurring, refractory, and/or resistant to said therapeutically active substance. In particular embodiments, said patient that has been CYP3A5-negative at the beginning of said treatment.

In particular embodiments, said one or more additional therapeutic agents are therapeutic agents for the treatment of the underlying cancer condition. In other particular embodiments, said one or more additional therapeutic agents are therapeutic agents for the treatment of a disease or disorder accompanying the underlying cancer condition.

In particular embodiments, said at least one of said additional therapeutic agents being a substrate for cytochrome P450 3A5 (CYP3A5) is selected from the list of: gefitinib, sorafenib, erlotinib, cyclophosphamide, vincristine, imatinib, tamoxifen, daunorubicin, irinotecan, etoposide, tacrolimus, sirolimus, thalidomide, ifosfamide, finasteride, paclitaxel, docetaxel, dasatinib, lapatinib, sunitinib, temsirolimus, crizotinib, ponatinib, cabazitaxel, and romidepsin, particularly selected from the list of erlotinib, dasatinib, paclitaxel, and irinotecan.

EXAMPLES

Example 1

Establishment of PDAC Models Representing Three PDAC Subtypes

We established a novel primary patient derived preclinical model system in vitro and in vivo, which recapitulates all three known PDAC subtypes (FIG. 1A). In detail, patient-derived PDAC specimens were surgically grafted onto the pancreas of immune-deficient NOD.Cg-Prkdc$^{scid}$ Il2rg$^{tm1Wjl}$ (NSG) mice (FIGS. 1A, 1B and 9A). Tumors from successful primary xenografts (PT) were then used to propagate stable, serum-free and adherent primary cell lines termed PACO (Pancreatic AdenoCarcinOma) (FIGS. 1A, 1B and 9A). PACO lines retained high in vivo tumorigenicity after orthotopic transplantation into secondary NSG mice. Comparison of the resulting PACO derived tumors (DT) with the original patient specimen (PT) showed conservation of all central histomorphological characteristics (FIGS. 1B and 9A). Pearson correlation analysis comparing RNA expression profiles across each step of our model system yielded consistently significant $R^2$ values (FIGS. 1C and 9C). In their initial description of the three molecular subtypes of PDAC defined by transcriptional profiling, Collisson et al. could not identify human cell lines or genetic mouse models, which matched the exocrine-like subtype (Collisson et al., 2011). Thus, we asked which of the described three subtypes were represented within our models. To this end, we used the 62-gene classifier for subtyping our first five PACO lines as well as for the respective DT and PT xenografts (Collisson et al., 2011). This analysis revealed that all three subtypes, including the exocrine-like subtype, are represented in our PDAC model (FIGS. 1D and 1E). Together, these results demonstrate that our PACO models not only faithfully preserve the patient phenotype, but for the first time provide in vivo and in vitro tools to comparatively study the biology of all three PDAC subtypes.

Example 2

Identification and Validation of a Novel Two-Marker Set for PDAC Subtypes

Although gene expression signatures are important tools for research, they are difficult to translate into clinical settings. Given that immunohistopathology is still the standard for tumor evaluation, we sought to identify protein markers for each of the PDAC subtypes, which could be applied for patient stratification. First, a list of genes showing strong (>5 fold, p<0.05) differential expression between the PACO subtypes was established. Then, this list was refined using the Protein Atlas database (Uhlen et al., 2010; FIG. 9A) and candidate markers were selected in case the corresponding antibody showed specific staining in only a subset of PDAC. In parallel, the GSEA motif module (Subramanian et al., 2005) was used to identify putative subtype-specific transcription factor activity. The latter analysis revealed an exclusive enrichment of genes containing binding-sites for the homeobox A transcription factor 1A (HNF1A) in the exocrine-like subtype. The list of all marker candidates tested and a summary of the results obtained is shown in FIG. 9A. Among them, nuclear expression of HNF1A was found to be specific for exocrine-like tumors, while Keratin-81 (KRT81) expression was specific for QM-PDA (FIGS. 2A-C). This marker set was validated on the initial five PACO lines (FIGS. 2A and 10B), the PACO derived xenografts (DT) (FIG. 2B) and primary patient tumors (FIG. 2C). Potential cross-reactions with murine or human stromal cells were not observed (FIGS. 2B and 2C). Therefore, we confirmed tumor specific expression for HNF1A and KRT81. None of the candidate antibodies analyzed for the classical subtype showed a reliable and exclusive signal in the corresponding tumor specimens (FIG. 9A). Nevertheless, the specificity of the identified two marker-set allowed us to define the classical subtype as double-negative (DN) for both markers (FIGS. 2A-C). This marker set was then used to classify any further PACO models we generated (FIGS. 9B and 10C). In summary, two of the cell lines and xenografts were of the classical subtype (PACO2 and 17), three of the exocrine-like (PACO10, 14, 18) and three of the QM-PDA subtype (PACO7, 9, 19) (FIGS. 9B and 10C). Next, we tested whether stratification of a PDAC patient cohort using those markers could reveal differences in clinical outcome. A tissue microarray (TMA) containing 251 specimens from PDAC patients that underwent surgical resection was analyzed by defining QM-PDA as KRT81+HNF1A−, exocrine-like tumors as KRT81−HNF1A+ and classical PDACs as DN (FIG. 10D). As a result, 45% of classical, 35% of QM-PDA and 20% of exocrine-like tumors were identified in this cohort. Survival data were available for 217 of the patients within the cohort. Log-rank analysis revealed significant differences in overall survival between the different PDAC subtypes (p<0.001) (FIG. 2D). Patients with an exocrine-like tumor had the best mean survival (43.5 months), followed by the classical (26.3 months), and then the QM-PDA subtype (16.5 months) (FIG. 2D). Moreover, cox proportional hazards multivariate analysis revealed that subtype defined by the novel two marker-set as an independent predictor for survival in addition to the known predictors age at diagnosis and lymph node status (Hruban et al., 2007; Wolfgang et al., 2013) (FIG. 2E). These data demonstrate not only that the two markers can be used to stratify PDAC patients according to the three subtypes, but also uncovered significant differences in overall survival, with exocrine-like patients having significantly better survival.

Example 3

Exocrine-Like PDAC Cells are Resistant Towards Small Molecule Inhibitors

Previous observations suggested that PDAC subtypes differ in drug sensitivity (Collisson et al., 2011). As no previous study included the exocrine-like subtype due to lack of model cell lines, we were especially interested in the drug-response of this subtype. To address this, the PACO lines were treated with gemcitabine, erlotinib and dasatinib at 1 µM (FIG. 3A) or 10 µM (FIG. 10A) and relative cell viability was determined after 48 hours. The classical and the QM-PDA subtype were sensitive towards all drugs tested (FIGS. 3A and 10A). In contrast, the exocrine-like subtype was almost completely resistant towards all three compounds at the concentrations tested (FIG. 3A and FIG. 10A). Thus, we aimed to identify the underlying mechanisms mediating the observed drug resistance. We used GSEA to compare the exocrine-like with the classical and QM-PDA subtype, both in the PACO lines (FIGS. 3B-3C and 11B) and in the xenografts (FIGS. 3D-E and 11C). This analysis revealed a significant enrichment of several signatures comprising genes involved in xenobiotic biotransformation. To validate our findings, we carried out the same analysis on an independent dataset generated from laser micro-dissected PDAC (Collisson et al., 2011). One of the signatures identified in our dataset was also found to be enriched in exocrine-like PDAC patients of this cohort (FIG. 10D). Taken together, these data indicate that drug detoxification mechanisms might be involved in mediating the observed drug resistance in the exocrine-like subtype.

Example 4

Subtype-Specific Expression and Induction of CYP3A5 In Vitro and In Vivo

To further investigate the mechanism of drug resistance, we asked whether any of the genes common to all identified signatures have been previously described to metabolize the compounds tested. Interestingly, we found that mRNA for the enzyme CYP3A5 was consistently highly enriched amongst all gene sets analyzed. Members of the CYP3A family (CYP3A4, CYP3A5 and CYP3A7) are known to significantly contribute to xenobiotic biotransformation of small molecule inhibitors, such as dasatinib and erlotinib in the liver (Guengrich, 2010). However, in contrast, these CYPs are not involved in gemcitabine detoxification (Mini et al., 2006). We performed qRT-PCR analysis for all three CYP3A family members in both the PACO cell lines as well as the derived xenografts. This confirmed that CYP3A5 is highly expressed in the exocrine-like subtype (FIGS. 4A and 4B), while mRNA expression of the other two enzymes was low to undetectable (FIGS. 12A-D). The relative abundance of CYP3A5 mRNA in the exocrine-like subtype was comparable or even higher than that of normal liver. In contrast, only small amounts of CYP3A5 mRNA were detectable in normal pancreas (FIGS. 4A and 4B). The high expression of CYP3A5, specifically in the exocrine-like subtype, was also confirmed at the protein level using Western blot analysis (FIG. 4C) and immunofluorescence (FIG. 9B). As the three CYP3A family members have related polypeptide sequences, we confirmed CYP3A5 antibody specificity by showing that it only recognizes recombinant CYP3A5, but not the two other family members (FIG. 11E). To further confirm the expression of CYP3A5 in PDAC, we carried out a retrospective immunohistochemical analysis of the patient cohort previously described (FIGS. 2D, 2E and 10C). CYP3A5 positive cells were detectable at varying intensities and frequencies in a subset of the patients (FIG. 4D). Univariate analysis revealed that CYP3A5 is predominantly found in those patients classified as exocrine-like (61.4% of cases; p<0.001) (FIGS. 4E and 12F) and did not significantly correlate with any of the other patient characteristics (FIG. 11F). In contrast, only 12.8% of the QM-PDA and only 11% of the classical subtype classified patients were CYP3A5 positive (FIGS. 4E and 12F). Moreover, Cox proportional hazards multivariate analysis revealed CYP3A5 expression as an independent predictor for PDAC patient survival (FIG. 11G). As CYP expression can be influenced by sex hormones (Thangavel et al., 2013), we tested for a possible association of CYP3A5 positivity and gender. However, Pearson chi-squared test revealed that CYP3A5 expression is independent of the patient's gender (FIG. 11H). One of the hallmarks of enzymes involved in xenobiotic biotransformation is their inducibility in response to their substrates, leading to a higher xenobiotic processing capacity upon drug exposure (Ding and Zhang, 2010). To test whether this regulatory mechanism is also functional in PDAC cells; we investigated CYP3A5 mRNA and protein expression at the basal level and in response to 10 µM dasatinib, erlotinib or gemcitabine in classical (PACO2), exocrine-like (PACO10, 14) and QM-PDA (PACO9) PACO cell lines (FIGS. 4F and 12I). Upon exposure to either dasatinib or erlotinib, CYP3A5 mRNA and CYP3A5 protein were strongly induced in the exocrine-like subtype. In contrast, treatment with gemcitabine did not lead to the induction of CYP3A5 (FIGS. 4F and 12I). Furthermore, treatment of the QM-PDA and the classical PACO lines with these compounds did not prompt CYP3A5 expression (FIGS. 4F and 12I). The expression of CYP3A4 and CYP3A7 was also not induced under any of these conditions (FIG. 11J). Taken together, these data show that CYP3A5 is highly expressed in tumors of the exocrine-like subtype in vitro and in vivo and its expression is further induced upon exposure to tyrosine-kinase inhibitors ("TKIs"), but not nucleoside-analogs, such as gemcitabine.

Example 5

Pan-Cytochrome P450 Inhibition Sensitizes Exocrine-Like PDAC Cells

In order to test this hypothesis we used the pan-cytochrome P450 inhibitor ketoconazole (Bruno and Njar, 2007). One PACO line of each subtype was pre-treated with 100 nM ketoconazole or vehicle for 2 hours, followed by the addition of serial dilutions of gemcitabine, erlotinib or dasatinib, respectively. Relative cell viability was determined after 48 hours (FIGS. 5A, 5B, and 13A). To compare drug effects across replicate experiments, we calculated the activity areas as described (Barretina et al., 2012) (FIG. 5B). Sensitivity towards all three tested compounds in the QM-PDA and the classical subtype remained unchanged by ketoconazole pre-treatment (FIGS. 5B, and 13A). Strikingly, cells of the exocrine-like subtype were significantly more sensitive towards erlotinib and dasatinib post ketoconazole treatment (FIGS. 5A, 5B). Thus, comparable sensitivities to the other two PDAC subtypes were achieved, completely reverting this drug resistant phenotype. Taken together, these results suggest that a member of the cytochrome P450 enzyme family is responsible for the observed drug resistance.

Example 6

CYP3A5 Metabolizes Erlotinib and Dasatinib in Exocrine-Like PDAC Cells

Enzymes of the cytochrome P450 family have previously been shown to metabolize small molecule substrates such as dasatinib and erlotinib by oxidation, potentially inactivating these molecules (Li et al., 2007; Wang et al., 2008). We hypothesized that due to its high expression, CYP3A5 could be the key enzyme metabolizing erlotinib and dasatinib. To test this, we used a siRNA-mediated knockdown approach to silence CYP3A5 expression. Knockdown efficiency was approximately 80% both at the mRNA and the protein level (FIGS. 6A, 6B and 14A, 14B). To test for CYP3A5-dependent metabolism we measured chemical modification of these small molecule inhibitors in two different (PACO14, 18) exocrine-like PACO lines, both in non-targeting (NT) and CYP3A5 siRNA transfected cells. The cells were then treated with 1 μM (FIG. 13D) and 10 μM (FIG. 6C) erlotinib or dasatinib, and supernatants were collected at six different time points. Quantitative LC-MS/MS analysis revealed a rapid conversion of erlotinib and dasatinib as illustrated by the disappearance of their unmodified structures from the supernatant (FIGS. 6C and 14D). (Li et al., 2007; Wang et al., 2008) In the absence of CYP3A5, metabolism of the natively bioactive erlotinib and dasatinib was completely abolished as shown by LC-MS/MS analysis of supernatants from both exocrine-like PACO lines (FIGS. 6C and 14D). Together, these data show that CYP3A5 is a key mediator of the metabolism of the small molecule inhibitors, erlotinib and dasatinib, in exocrine-like PDAC cells.

Example 7

CYP3A5 Plays a Role in Treatment-Induced Drug Resistance in PDAC

A common problem encountered in treatment of PDAC is the acquisition of drug-resistance, for which several mechanisms have been described (Sheik et al, 2010). We asked if CYP3A5 is upregulated in previously CYP3A5 low expressing or negative tumor cells of the QM-PDA or Classical subtype after drug treatment, and thus may contribute to treatment-induced drug resistance. To that end, we treated cells of the classical (PACO2) and of the QM-PDA (PACO7) subtypes with increasing doses of paclitaxel, erlotinib or dasatinib over a period of 8 weeks. Re-assessment of the sensitivity of the resulting drug-resistant sublines to the drugs used for long-term treatment confirmed that they had a significantly higher resistance compared to their DMSO-control treated parental lines (FIG. 17A). Analysis of the expression of CYP3A5 mRNA levels in the resistant cell lines revealed that the expression of CYP3A5 was significantly higher in the drug-resistant cell lines as compared to the control cell lines while expression of the related enzymes CYP3A4 and CYP3A7 was not detectable (FIG. 17B). We also tested if in a more physiological in vivo setting, treatment of tumor xenografts resulted in a similar upregulation of CYP3A5 in previously CYP3A5 low or negative tumors. Growth curves of the xenografts of the classical subtype (PACO17) treated with paclitaxel are shown in (FIG. 18A). Analysis of the xenografts after 18 days of treatment revealed that also in vivo, treatment with paclitaxel resulted in an upregulation of CYP3A5, compared to tumors from mice that were treated with vehicle, while expression of the related enzymes CYP3A4 and CYP3A7 was not upregulated (FIG. 18B). Staining of tissue sections for CYP3A5 demonstrated that the increase in CYP3A5 in drug-treated tumors is also detectable by immunhistochemistry (FIG. 18C).

We next tested of if the elevated expression of CYP3A5 indeed contributes to the treatment-induced resistance. As a proof-of principle compound we chose paclitaxel. Knockdown of CYP3A5 (FIG. 19A) indeed restored sensitivity of both the classical (PACO2) and QM-PDA (PACO7) paclitaxel-resistant sublines to levels comparable to the original cell line (FIG. 19B). Similarly, co-treatment of the cells with the pan-CYP inhibitor ketoconazole resulted in a comparable sensitization of the drug-resistant cell lines (FIG. 19C). Together, we conclude that treatment-induced drug resistance in PDAC can be mediated by upregulated CYP3A5, also in non exocrine-like PDAC and that inhibition of CYP3A5 expression or activity provides a novel strategy to overcome drug resistance in PDAC.

Example 8

CYP3A5 Mediates Drug Resistance in Exocrine-Like PDAC Cells

Chemical modifications can either activate or inactivate small molecule inhibitors (Janne et al., 2009). If CYP3A5 inactivates these compounds, the presence of high amounts of this enzyme would explain the observed resistance towards erlotinib and dasatinib in exocrine-like PDAC cells. Therefore, we tested whether knockdown of CYP3A5 in these cells altered their drug response. Gemcitabine was included as a control treatment, as it is not metabolized by a P450-dependent pathway (Mini et al., 2006). Non-targeting (NT-control) or CYP3A5 siRNA transfected cells were treated with serial dilutions of gemcitabine, erlotinib or dasatinib and relative cell viabilities were determined 48 hours post drug treatment. Knockdown of CYP3A5 dramatically sensitized the exocrine-like PACO cells towards erlotinib and dasatinib as evidenced by low cell viabilities post treatment (FIGS. 7A and 15A). To compare drug effects across the three independent biological replicates, we calculated the activity areas as described (Barretina et al., 2012) (FIG. 7B). The observed drug sensitization in the exocrine-like PACO cells was verified for two independent siRNAs (FIGS. 15A-15C). As expected, the CYP3A5 siRNA had no effect on cell lines of the classical and the QM-PDA subtypes that do not express CYP3A5 (FIGS. 15B and 15C). Furthermore, sensitivity to gemcitabine remained unchanged (FIGS. 7A, 7B, and 15A). As this deoxycytidine analogue is not metabolized by CYP3A5, these data exclude a general drug sensitization by the CYP3A5 knockdown. We next asked if ablation of CYP3A5 expression could sensitize established tumors for drug treatment in vivo. To that end, stable knockdown of CYP3A5 in PACO10 and 14 using two different hairpins (shCYP3A5_1 and _2) or scrambled control (shScr) were established. Knockdown efficiency of was confirmed by qRT-PCR and Western immunoblot (FIG. 7C). To verify drug sensitization in vitro, knockdown cells were treated with serial dilutions of gemcitabine, erlotinib or dasatinib and relative cell viabilities were determined 48 hours post drug treatment (FIG. 14D). Control or knockdown cell lines were established by subcutaneous injection into NSG mice. Once an average tumor volume of 200 mm$^3$ was achieved, mice were randomized and either treated with erlotinib or vehicle. No differences in growth between control and CYP3A5 knockdown tumors could be observed prior to randomization (data not shown) and in the vehicle treated animals (FIG. 7D), suggesting that CYP3A5 does not affect tumor growth under these conditions. While treatment with erlotinib had no effect on growth of the control tumors, growth of the CYP3A5 knockdown tumors was completely inhibited (FIG. 7D). In summary, our results confirm a central role of CYP3A5 in mediating resistance of the exocrine-like PDAC subtype to TKIs in vitro and in vivo.

Example 9

A More General Role of CYP3A5 Mediated Drug Resistance

Having shown that CYP3A5 plays a major role in the resistance to erlotinib and dasatinib, we next asked whether its expression might also impact recently introduced treatments for PDAC, such as nab-Paclitaxel or the FOLFIRINOX scheme (Conroy et al., 2011; von Hoff et al., 2013). Both, paclitaxel and the irinotecan component of the FOLFIRINOX scheme have been described to be substrates for CYP3A family members (Haaz et al., 1998; Sonnichsen and Relling, 1994). Treatment of PACO lines with both compounds at 1 µM and 10 µM for treatment durations of 48 h and 7 d, revealed that the exocrine-like subtype was highly resistant compared to the other two subtypes (FIG. 16A and FIG. 17A-C). As for erlotinib and dasatinib, knockdown of CYP3A5 rendered the exocrine-like PACO cells sensitive to irinotecan and paclitaxel, confirming a central role of this enzyme in mediating also resistance to those drugs (FIG. 16B). CYP family member expression has been described in a range of tumors (Guengrich 2010; Michael and Doherty, 2005). Given the important role of CYP3A5 in mediating resistance to a variety of clinically important drugs, we asked which other tumor entities might be impacted by the CYP3A5 expression. Staining of a TMA composed of 438 patient samples from 33 different tumor entities, revealed that 9 out of the 33 tumor types tested contained a fraction of CYP3A5 positive patients (FIGS. 16C and D). Together, these data suggest a more general role of CYP3A5 mediated in drug resistance, both in terms of substrates and tumor entities.

Example 10

CYP3A5 Plays a Role in Treatment Resistance of Hepatocellular Carcinoma and Gastric Cancer To determine if indeed CYP3A5 plays a role in tumor entities other than PDAC, we tested other cell lines derived from other tumor types for the expression of CYP3A5 and its possible role in drug-resistance. In particular, we found that the hepatocellular carcinoma cell line HepG2 expressed CYP3A5 mRNA and protein, as well as CYP3A4 and CYP3A7 mRNA (FIG. 20A-C). An siRNA-mediated knockdown of CYP3A5 significantly reduced the levels of CYP3A5 mRNA (FIG. 20D). While HepG2 cells treated with the non-targeting control siRNA were almost completely resistant to paclitaxel, knockdown of CYP3A5 significantly sensitized the cells to this treatment (FIG. 20E). Hence, knockdown of CYP3A5, even in the presence of the related enzymes CYP3A4 and CYP3A7 can significantly sensitize hepatocellular carcinoma cells to treatment with paclitaxel. Moreover, inhibition of CYP function by ketoconazole resulted in an even stronger sensitization (FIG. 20F). Similarly, the gastric cancer cell line SNU5 expresses mRNA for CYP3A5 and CYP3A4 (FIG. 21A) and inhibition of CYP activity by ketoconazole strongly sensitized this cell line to treatment with paclitaxel (FIG. 21B). Together, these data reveal that CYP3A5 is not only expressed but also contributes to treatment resistance in cancers other than PDAC.

Summary

Stratification of patients combined with subtype-specific therapeutic approaches is becoming increasingly important in clinical oncology, improving the efficacy of treatments in several cancer types (Mendelsohn, 2013). However, stratification of PDAC patients into meaningful therapy groups has so far been difficult and has not been implemented into clinical practice (Costello et al., 2012). This could be attributed in part to the presence of at least three molecular subtypes, which have recently been identified by Collisson et al. (Collisson et al., 2011). Although conventional tumor cell lines for the classical and the QM-PDA subtype have been identified, cell lines representing the exocrine-like subtype have been lacking thus far. As there are many genes commonly expressed between the exocrine-like subtype and acinar cells, the question was raised if the exocrine-like gene signature was the result of contaminating acinar cells. Our data now not only confirm the existence of the exocrine-like subtype in in vivo xenografts, but we have also established the first exocrine-like cell lines from this tumor type. Additionally, all our models show the hallmark mutations typically found in PDAC, such as KRAS and TP53 among others (Biankin et al., 2012; Jones et al., 2008; Yachida and Iacobuzio-Donahue, 2013) (data not shown). This excludes the possibility of a contamination with normal cells or the propagation of non-PDAC tumor types. Our models thus enabled us, for the first time, to functionally investigate the molecular and biological characteristics of the exocrine-like subtype.

As PDAC is characterized by an extensive stroma comprising up to 90% of the primary tumor mass, subtype stratification by gene expression analysis is prone to variation and thus a potential skewing of results (Feig et al., 2012). Hence, the use of these two markers, HNF1A and KRT81, which allow immunohistochemical stratification of PDAC samples by a specific in-situ evaluation restricted to the tumor cells, can overcome this problem. In support of our data, application of these markers to a cohort of 251 PDAC patients confirmed subtype stratification as an independent prognostic factor for survival and qualified this two-marker set for further exploration in prospective clinical trials.

But why would subtype stratification be of clinical interest for PDAC patient treatment? For pancreatic cancer, several promising drug candidates have failed in Phase III clinical trials (Hidalgo, 2010). However, drugs may be only effective in a subset of PDAC patients and thus may have been deemed unsuccessful due to the heterogeneity of the patient cohorts. Furthermore, the survival benefit provided by clinically available treatment regimens are often moderate (Werner et al., 2013). Hence, patient stratification by marker expression might lead to a more efficient and tailored drug use. Using the PACO lines as a platform to study differential drug sensitivities between PDAC subtypes, we have shown that the exocrine-like subtype is resistant to the TKIs erlotinib and dasatinib, as well as to paclitaxel and irinotecan. As PDAC patients with the exocrine-like subtype have the best survival, these findings might be perceived contradictory at first. However, patient survival is likely to be not only determined by drug response, but also by the growth rate of the primary tumor as well as the propensity for and the pattern of metastasis (Yachida and Iacobuzio-Donahue, 2013). Although patients with exocrine-like PDAC survive longer, the majority of patients die after a considerably short time interval. Therefore, overcoming drug resistance in the exocrine-like subtype will lead to improvements in clinical outcome in this patient subgroup.

Drug response in patients is strongly influenced by the expression of different CYPs that mediate substrate activation, detoxification and subsequent excretion. The hepatocellular cells mainly mediate systemic drug metabolism, while only minor amounts of these enzymes are expressed in other tissue types (Ding and Kaminsky, 2003; Pavek and Dvorak, 2008). Therefore, it was unexpected to identify RNA expression signatures that suggested an up-regulation of drug metabolism processes in the exocrine-like tumor cells. Xenobiotic biotransformation normally consists of several enzymatic steps with the rate-limiting step usually being CYP-mediated oxidation (Nebert and Dalton, 2006). Enzymes of the CYP family have a wide range of substrate affinities, thus metabolism of a given drug depends on the expression levels and patterns of CYPs (Nebert and Dalton, 2006). Amongst the CYP enzymes known to mediate the metabolism of erlotinib and dasatinib (Li et al., 2007; Wang et al., 2008), we identified CYP3A5 to be consistently highly expressed in the exocrine-like subtype and even further induced several fold by exposure to these drugs. The basal expression levels exceed even those found in the liver. Currently, promising efforts are focused on inhibiting CYPs responsible for hormone metabolism (Bruno and Njar, 2007), exemplified by the approval of the CYP17A1 inhibitor abiraterone for prostate cancer (Pezaro et al., 2012). Nonetheless, to date, a role for CYPs in drug detoxification restricted to tumor cells has never been functionally demonstrated and thus the high expression of CYP3A5 in the exocrine-like tumor cells is striking. Furthermore, we show that CYP3A5 actively and rapidly metabolizes dasatinib and erlotinib, leading to a resistance, which can be reverted by CYP3A5 knockdown or inhibition with ketoconazole.

Enzymes of the CYP family are also frequently induced by their substrates or related substances (Guengrich, 2010; Tompkins and Wallace, 2007). Interestingly, in exocrine-like PDAC cells only CYP3A5, but not the closely related family members CYP3A4 and CYP3A7, is expressed or induced in response to TKIs. As these enzymes can be co-regulated (Dvorak, 2012; Lin et al., 2002) specific transcriptional regulation may be functional in PDAC. Consequently, to fully understand CYP3A5 expression and function, the regulation of this enzyme in PDAC cells should be further investigated. This would not only add to a more complete understanding of this novel resistance mechanism, but may also offer additional drug target candidates. Systemic inhibition of the cytochrome P450 system is most likely not feasible in a therapeutic setting due to an expected high toxicity. However, specific inhibition of CYP3A5 may bear significant therapeutic potential, as low or absent expression of CYP3A5 in carriers of the CYP3A5*3 polymorphism leads to no apparent phenotype, suggesting that CYP3A5 fulfills a non-essential or redundant role (Kuehl et al., 2001; Westlind-Johnsson et al., 2003). The report of a CYP3A4 specific inhibitor demonstrates the feasibility to design inhibitors that distinguish between the closely related members of the CYP3A family (Walsky et al., 2012). Hence, a specific CYP3A5 inhibitor could likely be formulated and subsequently co-administered with TKIs to sensitize tumor cells towards compounds that are CYP3A5 substrates.

Our results also suggest that CYP3A5 expression should be taken into consideration when interpreting clinical studies of novel drugs for PDAC treatment. Known metabolic targets of this enzyme would be predicted to have decreased efficacy in patients expressing CYP3A5. One example is dasatinib, for which several clinical trials are registered, but despite encouraging pre-clinical data (Nagaraj et al., 2011; Trevino et al., 2006) have so far displayed negative results (Ghee et al., 2013). Moreover, a paclitaxel derivative and irinotecan containing treatment scheme have recently shown encouraging results and are entering clinical practice (Conroy et al., 2011; von Hoff et al., 2013). Hence, patient stratification might be required to uncover subtype-specific drug effects in clinical trials and to optimize patient care. Using our two-marker set, PDAC stratification into the exocrine (HNF1A$^+$), the quasi-mesenchymal (KRT81$^+$) and the classic (double-negative) subtype is now possible in a clinical setting. While we have found a significant association between the HNF1A positive exocrine-like subtype and CYP3A5 positivity, we also detected some potentially HNF1A negative tumors that were CYP3A5 positive. We also demonstrate a surprising role of CYP3A5 in treatment-induced drug resistance, also in tumors of the classical and QM-PDA subtypes, suggesting that determination of CYP3A5 status upon tumor-recurrence and development of therapy resistance might help to guide further therapeutic choices also in those patients. Hence, the inclusion of the CYP3A5 status as an additional marker might refine the prediction of drug response in PDAC patients.

In conclusion, our data demonstrate that CYP3A5, previously only implicated in systemic drug metabolism in hepatocytes, plays a critical role in mediating tumor tissue derived resistance to TKIs and other drugs such as paclitaxel and irinotecan. Our data uncover a novel mechanism of drug resistance employed by cancer cells, which is mediated by a targetable enzyme. Hence, these findings open new avenues for understanding and treating this disease, which may ultimately advance personalized treatment by enabling marker-based patient selection strategies in combination with tailored drug use.

Materials and Methods

Human Tissue Specimens

The study was performed with tissue samples obtained from the patients admitted to the Department of General, Visceral and Transplantation Surgery, University of Heidelberg (Prof. Dr. M. W. Büchler). The study was approved by the ethical committee of the University of Heidelberg (case number 301/2001) and conducted in accordance with the Helsinki Declaration; written informed consent was obtained from all patients. Primary patient and tumor characteristics are summarized in FIG. 8B.

Xenografts of Primary Tumor Specimens and PACO Cell Lines

To establish primary xenografts, tumors were cut into pieces of 1-2 mm$^3$ and implanted onto the pancreas of NOD.Cg-Prkdcscid Il2rgtm1Wjl (NSG) mice, which were bred in the animal facility of the German Cancer Research Center. For the generation of xenografts from the PACO lines, a suspension of 105-106 cultured cells in Matrigel (2 mg/ml) (BD) was injected into the pancreas of NSG mice. Successful engrafted tumors and subsequent growth was monitored by regular palpation of the implantation site. Animal care and all procedures followed the German legal regulations and were previously approved by the governmental review board of the state of Baden-Wuerttemberg, Regierungspräsidium Karlsruhe authorization number G64/10 and G39/13.

Generation of PACO Cultures

For the generation of PACO cultures, primary xenografts were resected after attaining a volume of approximately 1 cm3. Tumor pieces were first minced using sterile scalpels and dissociated into single cells by incubation with 1 µg/ml collagenase IV (Sigma) for 2 h at 37° C. The resulting suspension was filtered through a 100 µm mesh, and cell debris and dead cells were removed by density centrifugation (FiColl Paque Plus, Amersham). Remaining erythrocytes were removed using the ACK Buffer (Lonza). For establishing PACO cultures, single cells (5×106) were seeded in T75 flasks (Primaria, BD) in serum-free medium (referred to as PACO medium) as described before (Vermeulen et al., 2008). Adherent monolayer cultures were maintained at 37° C. and 5% $CO_2$. After the outgrowth of tumor cells, contaminating fibroblasts were removed by trypsinization. Established PACO lines were monthly authenticated (Multiplexion) and tested for mycoplasma contaminations.

siRNA Transfection of PACO Cells

PACO cells were grown to 80% confluence. The transfection reagent Dharmafect 4 (Thermo Scientific), non-targeting (NT) and CYP3A5 siRNA (On-Target plus SMARTpool/Set of 4; Thermo Scientific, see Table 2 for sequences) were pre-incubated at room temperature (RT) for 5 min at ratio of 1:4 in IMDM culture medium (Gibco). Dharmafect 4 was then combined with the siRNA and incubated for further 20 min at RT. The mixture was then added to the PACO culture medium. The culture medium was aspirated from the cells and the transfection agent-RNA complex mixture was added to the monolayer. Flasks were incubated at 37° C. for 72 h until further analysis.

Generation of Stable Knockdown Cells

Stable shRNA-mediated knockdown of CYP3A5 was achieved by targeting TTGATTTCAACATCTTTCT (shCYP3A5_1) and TGACTAAGTTGAAATCTCT (shCYP3A5_2) in pGIPZ vector (GE Healthcare, Thermo Scientific). In addition the non-silencing control pGIPZ vector (shScr) was used as negative control (GE Healthcare, Thermo Scientific). Lentiviral particles were produced in HEK 293T cells. Viral particles were concentrated and PACO cells were transduced at a multiplicity of infection of 1 to 5. Successfully transduced cells were selected by cell sorting for GFP. Knockdown efficiency was confirmed by qRT-PCR and Western immunoblotting.

Drug Treatment Assays

Gemcitabine and ketoconazole were obtained from Sigma Aldrich, dasatinib, paclitaxel, irinotecan and erlotinib from LC Laboratories. Gemcitabine was dissolved in sterile saline buffer (NaCl 0.9%), and dasatinib, paclitaxel, irinotecan and erlotinib in water-free DMSO. For the determination of the relative cell viability, serial dilutions of the three drugs were screened in quadruplicates. In brief, 8,000 cells/well were seeded in 96-well plates 24 h prior to the addition of individual compounds. For the co-treatment experiments, the siRNA protocol was carried out as earlier described or the cells were pretreated with 100 nM ketoconazole for 4 h and then treated in the presence of ketoconazole. After incubation for 48 h or 7 days, cell viability was assessed using CellTiterBlue (Promega) following manufacturer's instructions. Vehicle (saline buffer or DMSO) was use as negative control. Treatment with 10 µM staurosporine (LC Laboratories) was used as positive control. Relative cell viability curves were plotted using GraphPad Prism v 6.04 (Graph Pad Software).

Measurement of Conversion of Erlotinib and Dasatinib

In brief, the amount of unmodified dasatinib and erlotinib in the supernatant of cells was monitored by quantitative LC-MS/MS analysis on an AB Sciex QTrap 5500 tandem mass spectrometer.

Gene-Expression Analysis

Total RNA was isolated from different PACO lines at early and late passages at 80% confluence, or from 50 mg of tumor tissue using the miRNeasy kit (Qiagen) according to manufacturer's instructions. Gene expression analysis was performed using Illumina HumanHT-12v4 BeadChips at the Genomics and Proteomics Core Facility of DKFZ (GPCF DKFZ, Heidelberg). Correlation plots and respective Pearson coefficients ($R^2$) between samples were generated using 'R' (R Development Core Team. (Vienna, Austria, 2008)). Supervised hierarchical clustering (Pearson correlation, average linkage) and heatmap representation of differentially expressed genes at a p-value<0.05 of eight PACO lines was performed using the R/Bioconductor through the graphical user interface, Chipster (v2.12.0, build 1424; Finland, http://chipstercsc.fi/) (Kallio et al., 2011). Gene expression data were quantile-normalized, followed by a several groups test. Bonferroni correction was performed for p-value adjustments. In addition, Significant Analysis of Microarray (SAM) (Tusher et al., 2001) was used to identify differentially regulated genes at a FDR<0.05 with a fold change of >2.

Subtype Assignment

Gene Set Enrichment Analysis (GSEA) was conducted on quantile normalized data from the PACO datasets (PACO lines, PT and PACO-DT) in order to assign the corresponding PDAC subtypes to the individual samples. Previously, described PDAssigner signatures were used to derive genesets for each individual subtype (Collisson et al., 2011). GSEA was based on ranking genes according to their fold change for the indicated variables. The output of GSEA is an enrichment score (ES), a normalized enrichment score (NES) which accounts for the size of the gene set being tested, a p-value and an estimated False Discovery rate (FDR). We computed p-values using 1,000 permutations for each geneset and adjusted them with the FDR method (Nagaraj et al., 2011). Subtype assignment for eight samples was performed by comparing each individual sample against the remaining seven (denoted as 'REST') for each geneset. A sample was assigned to a subtype when FDR<2 for the corresponding geneset. When FDR was <0.2 for more than one signature, samples were assigned to the signature with the lowest p-val.

Real-Time Quantitative PCR

Total RNA was extracted using the miRNeasy mini kit (Qiagen) and reverse transcribed using the high capacity cDNA reverse transcription kit (Applied Biosystems). cDNA corresponding to 10 ng of starting RNA was used for relative RNA quantification. TaqMan probes (Applied Biosystems) for CYP3A5 (HS00241417_m1), CYP3A4 (HS0060406_m1), CYP3A7 (Hs00426361_m1) PPIA (HS04194521_s1) and GAPDH (HS9999905_m1) were used to acquire expression data with the Viia™ 7 Real-Time PCR System (Applied Biosystems). The ViiA™ 7 software 1.1 was used for data acquisition and analysis. As positive control RNA from normal liver and pancreas was used (Novus).

Immunohistochemistry

Tumor specimens were fixed in 10% formalin overnight and embedded in paraffin. For immunohistochemistry, slides were de-paraffinized and rehydrated. Antigen retrieval was enhanced by boiling in a steam pot at pH 6 (Dako target retrieval solution, Dako) for 15 min, after that, slides were allowed to cool for 30 min and washed in distilled water. Nonspecific binding was blocked using the Linaris Avidin/Biotin blocking Kit (Vector Labs) according to the manufacturers' instructions. Slides were incubated with primary antibodies for 30 min, rinsed in PBS-T (PBS with 0.5% Tween-20), incubated for 20 min with the appropriate secondary antibody using the Dako REAL Detection System and rinsed in PBS-T. After blocking of endogenous peroxidase and incubation with Streptavidin HRP (20 min at RT), slides were developed with AEC (Dako) and counterstained with Hematoxylin. Primary antibodies were used as described in the antibody section (see Table 1 below). All antibodies were diluted in Dako antibody diluent. Two pathologists evaluated all sections independently; discordant cases were discussed using a multiheaded microscope until consensus was achieved. For Analysis and statistics were performed using GraphPad Prism (v6.04, GraphPad Software).

Tissue Microarray

The tissue microarray was constructed from patients that received partial pancreatoduodenectomy for PDAC between 1991 and 2006 at the Charité University Hospital Berlin. The use of this tumor cohort for biomarker analysis has been approved by the Charité University ethics committee (EA1/06/2004). Formalin-fixed and paraffin-embedded tissue samples were used to generate tissue microarrays as described previously (Weichert et al., 2008). Briefly, three morphologically representative regions of the paraffin 'donor' blocks were chosen. From these regions, tissue cylinders of 1.5 mm diameter were punched from each donor sample and arrayed into a new 'recipient' paraffin block using a semiautomated tissue microarrayer (Beecher Instruments, Silver Spring, Md., USA). The human various cancers high density TMA, which is composed of VA2-SBC, VB2-SBC and VC2-SBC (n=438), was purchased from Super Bio Chips (Korea) via BioCat (Heidelberg).

Immunohistochemistry

For a list of all marker candidates tested and a summary of the results obtained see FIG. 9A. Tumor specimens were fixed in 10% formalin overnight and embedded in paraffin. For immunohistochemistry, slides were de-paraffinized and rehydrated. Antigen retrieval was enhanced by boiling in a steam pot at pH 6 (Dako target retrieval solution, Dako) for 15 min, followed by cooling for 30 min and washing in distilled water. Nonspecific binding was blocked using the Linaris Avidin/Biotin blocking Kit (Vector Labs) according to the manufacturers' instructions. Slides were incubated with primary antibodies for 30 min, rinsed in PBS-T (PBS with 0.5% Tween-20), incubated for 20 min with the appropriate secondary antibody using the Dako REAL Detection System and rinsed in PBS-T. After blocking of endogenous peroxidase and incubation with Streptavidin HRP (20 min at RT), slides were developed with AEC (Dako) and counterstained with Hematoxylin. Primary antibodies were used as described in the antibody section (see Table 1 below). All antibodies were diluted in Dako antibody diluent. Two pathologists evaluated all sections independently; discordant cases were discussed using a multiheaded microscope until consensus was achieved. The study was carried out blinded to the identity of the specimens. A case was considered positive for a given marker (CYP3A5, KRT81, HNF1A), if the tumor cells in the respective tissue microarray spots showed a detectable staining regardless of the strength of the signal or the number of positive cells. However, in those instances, in which staining of tumor cells was detectable for any of the markers the respective staining was usually strong. Stromal cells were negative in all instances; normal acinar pancreatic cells (when present) expressed HNF1A homogenously to a moderate degree but were consistently negative for the other two markers.

Immunofluorescence

PACO cells were seeded on T75 flasks (Primaria, BD) and grown to 60-70% confluence. Cells were fixed in 4% freshly depolymerized formaldehyde for 15 min, permeabilized with 0.25% (v/v) Triton X-100 (Sigma) for 45 min and blocked with 1% BSA for 1 h. Primary antibodies (see Table 1) were incubated O/N at 4° C. and detected by fluorescence using secondary antibodies coupled to fluorochromes diluted 1:1000 (Life Technologies) for 1 h in the dark. Isotype-matched secondary antibodies conjugated with Alexa-Fluor-488 or PE were incubated for 1 h at RT. Slides were mounted using ProLong Antifade GOLD with DAPI (Life Technologies) as described by the manufacturer.

Western Blot Analysis

Whole cell lysates from PACO cells were prepared using RIPA buffer (Cell Signaling), 1 mM PMSF (Sigma), 1 mM EDTA and Halt Protease/Phosphatase Inhibitor Cocktail (Pierce). Protein lysates were resolved on 4-12% Bis/Tris NuPage gels with MOPS running buffer (Life Technologies) and blotted on nitrocellulose membranes (Amersham International). Membranes were blocked for 1 h in TBS containing 0.1% (v/v) Tween-20 with 20% (w/v) nonfat dry milk powder (blocking solution). Primary antibodies (see Materials and Methods) were incubated O/N at 4° C. in blocking solution. Secondary were diluted 1:10000 in blocking solution and incubated for 1 h at RT. Membranes were washed in TBS-Tween 0.1% and immunocomplexes were detected using the ECL kit (Amersham International). As positive control recombinant CYP3A5, CYP3A4, CYP3A7 (Abnova) and total human liver lysates (Novus) were used.

In Vivo Drug Treatment

Tumors were established by subcutaneously injecting $5 \times 10^5$ shCYP3A5 or shScr PACO cells into female NOD.Cg-Prkdc$^{scid}$ Il2rg$^{tm1Wjl}$ (NSG) mice (n=48) using Matrigel (2 mg/ml) in a total injection volume of 100 µl. After the tumors reached a size of approximately 200 mm$^3$, mice were randomized into eight groups (n=6 each) for drug administration. Erlotinib was prepared in 0.5% methylcellulose, 0.1% Tween 80 and 99.4% water for injection (WFI). Erlotinib (100 mg/kg) or vehicle were then administrated by oral gavage at 5 consecutive days followed by 2 days of rest, for duration of 14 days. Tumor volume was determined twice weekly by calliper measurements and calculated according to the formula (length×height×width)×(π/6). Tumor growth was calculated for each individual tumor by normalizing to the tumor volume at day 0. After two weeks of treatment, mice were sacrificed and tumors were resected for further analysis.

Statistical Analysis

Quantitative results were analyzed by one-way analysis of variance (multiple groups/grouped analysis) and Student's t test (two groups), using GraphPad Prism (Graph Pad Software). Survival analysis was performed using Mantel-Cox log-rank test as well as Cox proportional hazards multivariate analysis using the Statistical Package for the Social Sciences (IPM SPSS software). Additionally, Pearson chi-squared test was used for comparative data analysis, using SPSS. We considered p<0.05 (two-sided) as statistically significant. For GSEA a False Discovery Rate (FDR) of <0.2 was considered statistically significant. Treatment data were evaluated by determining the activity area (Barretina et al., 2012) from each dose response curve by adding max (100-mean response, 0) for every concentration. Activity areas from the same biological replicate were compared by paired t-test. Calculations were performed in R Version 3.1.0 (Chee et al., 2013).

LC-MS/MS Analysis (S)-(−)-Propranolol hydrochloride (Internal Standard) was purchased from Sigma-Aldrich (Taufkirchen, Germany). Acetonitrile was from Bernd Kraft (Duisburg, Germany), ammonium acetate, formic acid from Merck (Darmstadt, Germany), methanol from VWR International (Darmstadt, Germany) and dimethylsulfoxide from Applichem (Darmstadt, Germany).

500 µl of reaction media were quenched with 1,000 µL of acetonitrile at each time point and mixed. After centrifugation clear supernatants were pre-diluted with PACO media and acetonitrile at a ratio 1:25. 100 µL of the sample were transferred into a new vial, followed by addition of 10 µL of (S)-(−)-Propranolol hydrochloride solution (105 µg/L) and finally vigorously mixed. 10 µL were injected onto column. Calibration and quality control samples were prepared by spiking either dasatinib or erlotinib to the PACO media. The sample was injected onto a PerfectSil Target ODS-3, 3 µm, 100×2.1 mm HPLC column (MZ-Analysentechnik, Mainz, Germany), using an Agilent 1100 (Agilent, Waldbrunn, Germany) binary pump and degasser, with a CTC PAL sampler (CTC Analytics, Zwingen, Switzerland). The column temperature was 35° C. Chromatographic separation was performed by gradient elution at a constant flow rate of 250 µL/min for 15 minutes. The gradient consisted of 20 mM NH$_4$OAc plus 0.1% formic acid (mobile phase A) and 400 mM NH$_4$OAc/methanol/acetonitrile 5:5:90 plus 0.1% formic acid (mobile phase B). The gradient applied was 0.0 min, 70% A/30% B; 1.5 min 70% A/30% B; 3.0 min 5% A/95% B; 11.0 min 5% A/95% B; 11.5 min 70% A/30% B and 15 min 70% A/30% B. The eluate was directed to an AB Sciex QTrap 5500 tandem mass spectrometer (AB Sciex, Darmstadt, Germany) with an electron spray ionization (ESI) source from 4 to 8 min runtime. Mass transitions of 488.1 to 401.1 for dasatinib, 394.0 to 278.1 for erlotinib and 260.1 to 116.1 for (S)-(−)-Propranolol were monitored. Ionization was achieved at 5.5 kV and a temperature of 400° C. Nitrogen was produced by a high purity nitrogen generator (CMC Instruments) and applied to curtain, collision and drying gasses. De-clustering potentials, collision energy and collision exit potential were as follows: 26 V, 39 V and 12 V for dasatinib, 16 V, 43 V and 26 V for erlotinib and 61 V, 23 V and 14 V for (S)-(−)-Propranolol.

The following primary antibodies were used for immunohistochemistry, immunofluorescence and Western blot analysis at the indicated dilutions.

TABLE 1

Antibodies:

| Antigen | Manufacturer (Clone) | Technique and dilution |
| --- | --- | --- |
| HNF-1 | Santa Cruz (H-205) | IHC (1:50); IF (1:500) |
| Keratin 81 | Santa Cruz (36-Z) | IHC (1:100); IF (1:500) |
| CYP3A5 | Abcam (EPR4396) | WB (1:1000); IF (1:500) |
| Vinculin | Cell Signaling (E1E9V) | WB (1:1000) |

TABLE 2 siRNA and shRNA Sequences:

| Oligonucleotides | Sequence | |
| --- | --- | --- |
| CYP3A5-siRNA1 | 5' CCUUGAAAUUAGACACGCA 3' | (SEQ ID NO. 1) |
| CYP3A5-siRNA2 | 5' CGUGAUCAGAACAGUGCUA 3' | (SEQ ID NO. 2) |
| CYP3A5-siRNA3 | 5' GGUCAAUGGUGGUGAUUCC 3' | (SEQ ID NO. 3) |
| CYP3A5-siRNA4 | 5' CUAUUAGACUUGAGAGGAC 3' | (SEQ ID NO. 4) |
| Non-targeting control siRNA 1 | 5' UGGUUUACAUGUCGACUAA 3' | (SEQ ID NO. 5) |
| Non-targeting control siRNA 2 | 5' UGGUUUACAUGUUGUGUGA 3' | (SEQ ID NO. 6) |
| Non-targeting control siRNA 3 | 5' UGGUUUACAUGUUUUCUGA 3' | (SEQ ID NO. 7) |
| Non-targeting control siRNA 4 | 5' UGGUUUACAUGUUUUCCUA 3' | (SEQ ID NO. 8) |
| CYP3A5_V3LHS_367932_antisense_shRNA1 | 5' TTGATTTCAACATCTTTCT 3' | (SEQ ID NO. 9) |
| CYP3A5_V3LHS_409651_antisense_shRNA2 | 5' TGACTAAGTTGAAATCTCT 3' | (SEQ ID NO. 10) |

REFERENCES

Barretina, J., Caponigro, G., Stransky, N., Venkatesan, K., Margolin, A. A., Kim, S., Wilson, C. J., Lehar, J., Kryukov, G. V., Sonkin, D., et al. (2012). The Cancer Cell Line Encyclopedia enables predictive modelling of anticancer drug sensitivity. Nature 483, 603-607.

Biankin, A. V., Waddell, N. Kassahn, K. S., Gingras, M. C., Muthuswamy, L. B. Johns, A. L, et al., Pancreatic cancer genomes reveal aberrations in axon guidance pathway genes. Nature 491, 399-405 (2012).

Bruno, R. D., and Njar, V. C. O. (2007). Targeting cytochrome P450 enzymes: A new approach in anticancer drug development. Bioorganic & Medicinal Chemistry 15, 5047-5060.

Burris, H. A., 3rd, Moore, M. J., Andersen, J., Green, M. R., Rothenberg, M. L., Modiano, M. R., Cripps, M. C., Portenoy, R. K., Storniolo, A. M., Tarassoff, P., et al. (1997). Improvements in survival and clinical benefit with Gemcitabine as first-line therapy for patients with advanced pancreas cancer: a randomized trial. Journal of clinical oncology: official journal of the American Society of Clinical Oncology 15, 2403-2413.

Castell J. V., Donato M. T., Gómez-Lechón M. J. (2005). Metabolism and bioactivation of toxicants in the lung. The in vitro cellular approach. Exp Toxicol Pathol. 57 Suppl 1: 189-204.

Chee, C. E., Krishnamurthi, S., Nock, C. J., Meropol, N. J., Gibbons, J., Fu, P., Bokar, J., Teston, L., O'Brien, T., Gudena, V., Reese, A., Bergman, M., Saltzman, J., Wright, J. J., Dowlati, A., Brell, J., Phase II study of dasatinib (BMS-354825) in patients with metastatic adenocarcinoma of the pancreas. The Oncologist 18, 1091-1092 (2013).

Collisson, E. A., Sadanandam, A., Olson, P., Gibb, W. J., Truitt, M., Gu, S. D., Cooc, J., Weinkle, J., Kim, G. E., Jakkula, L., et al. (2011). Subtypes of pancreatic ductal adenocarcinoma and their differing responses to therapy. Nat Med 17, 500-503.

Conroy, T., Desseigne, F., Ychou, M., Bouche, O., Guimbaud, R., Becouarn, Y., Adenis, A., Raoul, J. L., Gourgou-Bourgade, S., de la Fouchardiere, C., et al. (2011). FOLFIRINOX versus Gemcitabine for metastatic pancreatic cancer. The New England Journal of Medicine 364, 1817-1825.

Costello, E., Greenhalf, W., and Neoptolemos, J. P. (2012). New biomarkers and targets in pancreatic cancer and their application to treatment. Nature Reviews Gastroenterology & Hepatology 9, 435-444.

Ding, X., and Kaminsky, L. S. (2003). Human extrahepatic cytochromes P450: function in xenobiotic metabolism and tissue-selective chemical toxicity in the respiratory and gastrointestinal tracts. Annual Review of Pharmacology and Toxicology 43, 149-173.

Ding, X., and Zhang, Q. Y. (2010). 4.02—Enzyme Regulation. In Comprehensive Toxicology (Second Edition), C. A. McQueen, ed. (Oxford: Elsevier), pp. 9-29.

Downie D., McFadyen M. C., Rooney P. H., Cruickshank M. E., Parkin D. E., Miller I. D., Telfer C., Melvin W. T., Murray G. I. (2005). Profiling cytochrome P450 expression in ovarian cancer: identification of prognostic markers. Clin Cancer Res. 11:7369-75.

Dvorak, Z., in Metabolism of Drugs and Other Xenobiotics. (Wiley-VCH Verlag GmbH & Co. KGaA, 2012), pp. 223-258.

Feig, C., Gopinathan, A., Neesse, A., Chan, D. S., Cook, N., and Tuveson, D. A. (2012). The pancreas cancer microenvironment. Clin Cancer Res 18, 4266-4276.

George, T. J., Jr., Trevino, J. G., Liu, C., Src inhibition is still a relevant target in pancreatic cancer. The Oncologist 19, 211 (2014).

Guengrich, F. P. (2010). Cytochrome P450 Enzymes. In Comprehensive Toxicology (Second Edition), C. A. McQueen, ed. (Elsevier Ltd.), pp. 43-76.

Haaz, M. C., Rivory, L., Riche, C., Vernillet, L., Robert, J., Metabolism of irinotecan (CPT-11) by human hepatic microsomes: participation of cytochrome P-450 3A and drug interactions. Cancer Research 58, 468-472 (1998).

Hidalgo, M. (2010). Pancreatic cancer. The New England Journal of Medicine 362, 1605-1617.

Hong, D. S., Choe, J. H., Naing, A., Wheler, J. J., Falchook, G. S., Piha-Paul, S., Moulder, S. L., George, G. C., Choe, J. M., Strauss, L. C., Gallick, G. E., Kurzrock, R., A phase 1 study of gemcitabine combined with dasatinib in patients with advanced solid tumors. Investigational New Drugs 31, 918-926 (2013).

Hruban, R. H., Pitman, M. B., Klimstra, D. S., Tumors of the pancreas: AFIP atlas of tumor pathology. Fourth series (American Registry of Pathology in collaboration with the Armed Forces Institute of Pathology, Washington, D.C., 2007).

Janne, P. A., Gray, N., and Settleman, J. (2009). Factors underlying sensitivity of cancers to small-molecule kinase inhibitors. Nature Reviews Drug Discovery 8, 709-723.

Jones, S., Zhang, X., Parsons, D. W., Lin, J. C., Leary, R. J., Angenendt, P., Mankoo, P., Carter, H., Kamiyama, H., Jimeno, A., Hong, S. M., Fu, B., Lin, M. T., Calhoun, E. S., Kamiyama, M., Walter, K., Nikolskaya, T., Nikolsky, Y., Hartigan, J., Smith, D. R., Hidalgo, M., Leach, S. D., Klein, A. P., Jaffee, E. M., Goggins, M., Maitra, A., Iacobuzio-Donahue, C., Eshleman, J. R., Kern, S. E., Hruban, R. H., Karchin, R., Papadopoulos, N., Parmigiani, G., Vogelstein, B., Velculescu, V. E., Kinzler, K. W., Core signaling pathways in human pancreatic cancers revealed by global genomic analyses. Science 321, 1801-1806 (2008).

Kallio, M. A., Tuimala. J. T., Hupponen, T., Klemela, P., Gentile, M., Scheinin, I., Koski, M., Kaki, J., Korpelainen, E. I., Chipster: user-friendly analysis software for microarray and other high-throughput data. BMC Genomics 12, 507 (2011).

Kivistö K. T., Griese E.-U., Fritz P., Linder A., Hakkola J., Raunio H., Beaune P., Kroemer H. K. (1996). Expression of cytochrome P 450 3A enzymes in human lung: a combined RT-PCR and immunohistochemical analysis of normal tissue and lung tumours. Naunyn Schmiedebergs Arch Pharmacol. 353:207-12.

Kuehl, P., Zhang, J., Lin, Y., Lamba, J., Assem, M., Schuetz, J., Watkins, P. B., Daly, A., Wrighton, S. A., Hall, S. D., et al. (2001). Sequence diversity in CYP3A promoters and characterization of the genetic basis of polymorphic CYP3A5 expression. Nature Genetics 27, 383-391.

Leclerc J., Tournel G., Courcot-Ngoubo Ngangue E., Pottier N., Lafitte J. J., Jaillard S., Mensier E., Lhermitte M., Broly F., Lo-Guidice J. M. (2009). Profiling gene expression of whole cytochrome P450 superfamily in human bronchial and peripheral lung tissues: Differential expression in non-small cell lung cancers. Biochimie 92:292-306.

Li, J., Zhao, M., He, P., Hidalgo, M., and Baker, S. D. (2007). Differential metabolism of gefitinib and Erlotinib by human cytochrome P450 enzymes. Clin Cancer Res 13, 3731-3737.

Lin, Y. S., Dowling, A. L. S., Quigley, S. D., Farin, F. M., Zhang, J., Lamba, J., Schuetz, E. G., Thummel, K. E. (2002). Co-Regulation of CYP3A4 and CYP3A5 and Contribution to Hepatic and Intestinal Midazolam Metabolism. Molecular Pharmacology 62, 162-172.

Maguire O., Pollock C., Martin P., Owen A., Smyth T., Doherty D., Campbell M. J., McClean S., Thompson P. (2012). Regulation of CYP3A4 and CYP3A5 expression and modulation of "intracrine" metabolism of androgens in prostate cells by liganded vitamin D receptor. Mol Cell Endocrinol. 364:54-64.

Malvezzi, M., Bertuccio, P., Levi, F., La Vecchia, C., and Negri, E. (2014). European cancer mortality predictions for the year 2014. Annals of Oncology: Official Journal of the European Society for Medical Oncology/ESMO.

Mendelsohn, J., Personalizing Oncology: Perspectives and Prospects. Journal of Clinical Oncology 31, 1904-1911 (2013).

Michael, M., and Doherty, M. M. (2005). Tumoral drug metabolism: Overview and its implications for cancer therapy. Journal of Clinical Oncology 23, 205-229.

Michael, M., and Doherty, M. M. (2007). Drug metabolism by tumours: its nature, relevance and therapeutic implications. Expert Opinion on Drug Metabolism & Toxicology 3, 783-803.

Mini, E., Nobili, S., Caciagli, B., Landini, I., and Mazzei, T. (2006). Cellular pharmacology of Gemcitabine. Annals of Oncology: Official Journal of the European Society for Medical Oncology/ESMO 17 Suppl 5, v7-12.

Moore, M. J., Goldstein, D., Hamm, J., Figer, A., Hecht, J. R., Gallinger, S., Au, H. J., Murawa, P., Walde, D., Wolff, R. A., et al. (2007). Erlotinib plus Gemcitabine compared with Gemcitabine alone in patients with advanced pancreatic cancer: a phase Ill trial of the National Cancer Institute of Canada Clinical Trials Group. Journal of Clinical Oncology: Official Journal of the American Society of Clinical Oncology 25, 1960-1966.

Nagaraj, N. S., Washington, M. K., Merchant, N. B., Combined blockade of Src kinase and epidermal growth factor receptor with gemcitabine overcomes STAT3-mediated resistance of inhibition of pancreatic tumor growth. Clin Cancer Res 17, 483-493 (2011).

Nebert, D. W., and Dalton, T. P. (2006). The role of cytochrome P450 enzymes in endogenous signaling pathways and environmental carcinogenesis. Nature Reviews Cancer 6, 947-960.

Pavek, P., and Dvorak, Z. (2008). Xenobiotic-induced transcriptional regulation of xenobiotic metabolizing enzymes of the cytochrome P450 superfamily in human extrahepatic tissues. Curr Drug Metab 9, 129-143.

Pezaro, C. J., Mukherji, D., and De Bono, J. S. (2012). Abiraterone acetate: redefining hormone treatment for advanced prostate cancer. Drug Discovery Today 17, 221-226.

Plummer S. J., Conti D. V., Paris P. L., Curran A. P., Casey G., and Witte J. S. (2003). CYP3A4 and CYP3A5 genotypes, haplotypes, and risk of prostate cancer. Cancer Epidemiol Biomarkers Prev. 12:928-32.

R Development Core Team (2008). R: A Language and Environment for Statistical Computing. In, (Vienna, Austria).

Sanchez, R. I., and Kauffman, F. C. (2010). Regulation of Xenobiotic Metabolism in the Liver. In Comprehensive Toxicology (Second Edition), C. A. McQueen, ed. (Elesvier Ltd.), pp. 109-128.

Schilsky, R. L. (2010). Personalized medicine in oncology: the future is now. Nature Reviews Drug Discovery 9, 363-366.

Sheikh, R., Walsh, N., Clynes, M., O'Connor, R., and McDermott, R. (2010). Challenges of drug resistance in the management of pancreatic cancer. Expert Review of Anticancer Therapy 10, 1647-1661.

Siegel, R., Naishadham, D., and Jemal, A. (2013). Cancer statistics, 2013. CA: a cancer journal for clinicians 63, 11-30.

Sonnichsen, D. S. and Relling, M. V., Clinical pharmacokinetics of paclitaxel. Clinical Pharmacokinetics 27, 256-269 (1994).

Stenzinger, A., Endris, V., Klauschen, F., Sinn, B., Lorenz, K., Warth, A., Goeppert, B., Ehemann, V., Muckenhuber, A., Kamphues, C., Bahra, M., Neuhaus, P., Weichert, W., High SIRT1 expression is a negative prognosticator in pancreatic ductal adenocarcinoma. BMC Cancer 13, 450 (2013).

Subramanian, A., Tamayo, P., Mootha, V. K., Mukherjee, S., Ebert, B. L., Gillette, M. A., Paulovich, A., Pomeroy, S. L., Golub, T. R., Lander, E. S., and Mesirov, J. P. (2005). Gene set enrichment analysis: a knowledge-based approach for interpreting genome-wide expression profiles. Proceedings of the National Academy of Sciences of the United States of America 102, 15545-15550.

Thangavel, C., Boopathi, E., and Shapiro, B. H. (2013). Inherent sex-dependent regulation of human hepatic CYP3A5. British Journal of Pharmacology 168, 988-1000.

Tompkins, L. M., and Wallace, A. D. (2007). Mechanisms of cytochrome P450 induction. Journal of Biochemical and Molecular Toxicology 21, 176-181.

Trevino, J. G., Summy, J. M., Lesslie, D. P., Parikh, N. U., Hong, D. S., Lee, F. Y., Donato, N. J., Abbruzzese, J. L., Baker, C. H., Gallick, G. E., Inhibition of SRC expression and activity inhibits tumor progression and metastasis of human pancreatic adenocarcinoma cells in an orthotopic nude mouse model. The American Journal of Pathology 168, 962-972 (2006).

Tusher, V. G., Tibshirani, R., and Chu, G. (2001). Significance analysis of microarrays applied to the ionizing radiation response. Proceedings of the National Academy of Sciences of the United States of America 98, 5116-5121.

Uhlen, M., Oksvold, P., Fagerberg, L., Lundberg, E., Jonasson, K., Forsberg, M., Zwahlen, M., Kampf, C., Wester, K., Hober, S., et al. (2010). Towards a knowledge-based Human Protein Atlas. Nature Biotechnology 28, 1248-1250.

Vanneman, M., and Dranoff, G. (2012). Combining immunotherapy and targeted therapies in cancer treatment. Nature Rviews Cancer 12, 237-251.

Vermeulen, L., Todaro, M., de Sousa Mello, F., Sprick, M. R., Kemper, K., Perez Alea, M., Richel, D. J., Stassi, G., and Medema, J. P. (2008). Single-cell cloning of colon cancer stem cells reveals a multi-lineage differentiation capacity. Proceedings of the National Academy of Sciences of the United States of America 105, 13427-13432.

Vincent, A., Herman, J., Schulick, R., Hruban, R. H., and Goggins, M. (2011). Pancreatic cancer. Lancet 378, 607-620.

Von Hoff, D. D., Ervin, T., Arena, E P., Chiorean, E. G., Infante, J., Moore, M., Seay, T., Tjulandin, S. A., Ma, W. W., Saleh, M. N., et al. (2013). Increased survival in pancreatic cancer with nab-paclitaxel plus Gemcitabine. The New England Journal of Medicine 369, 1691-1703.

Walsky, R. L., Obach, R. S., Hyland, R., Kang, P., Zhou, S., West, M., Geoghegan, K. F., Helal, C. J., Walker, G. S., Goosen, T. C., and Zientek, M. A. (2012). Selective mechanism-based inactivation of CYP3A4 by CYP3cide (PF-04981517) and its utility as an in vitro tool for delineating the relative roles of CYP3A4 versus CYP3A5 in the metabolism of drugs. Drug metabolism and disposition: the biological fate of chemicals 40, 1686-1697.

Wang, L., Christopher, L. J., Cui, D., Li, W., Iyer, R., Humphreys, W. G., and Zhang, D. (2008). Identification of the human enzymes involved in the oxidative metabolism of Dasatinib: an effective approach for determining metabolite formation kinetics. Drug metabolism and disposition: the biological fate of chemicals 36, 1828-1839.

Weichert, W., Roske, A., Gekeler, V., Beckers, T., Ebert, M. P., Pross, M., Dietel, M., Denkert, C., and Rocken, C. (2008). Association of patterns of class I histone deacetylase expression with patient prognosis in gastric cancer: a retrospective analysis. The Lancet Oncology 9, 139-148.

Werner, J., Combs, S. E., Springfeld, C., Hartwig, W., Hackert, T., and Buchler, M. W. (2013). Advanced-stage pancreatic cancer: therapy options. Nature Reviews Clinical Oncology 10, 323-333.

Westlind-Johnsson, A., Malmebo, S., Johansson, A., Otter, C., Andersson, T. B., Johansson, I., Edwards, R. J., Boobis, A. R., and Ingelman-Sundberg, M. (2003). Comparative analysis of CYP3A expression in human liver suggests only a minor role for CYP3A5 in drug metabolism. Drug Metabolism and Disposition 31, 755-761.

Wolfgang, C. L., Herman, J. M., Laheru, D. A., Klein, A. P., Erdek, M. A., Fishman, E. K., Hruban, R. H., Recent progress in pancreatic cancer. CA: a Cancer Journal for Clinicians 63, 318-348 (2013).

Yachida, S., and Iacobuzio-Donahue, C. A. (2013). Evolution and dynamics of pancreatic cancer progression. Oncogene 32, 5253-5260.

Zhang, J., Yang, P. L., and Gray, N. S. (2009). Targeting cancer with small molecule kinase inhibitors. Nature reviews Cancer 9, 28-39.

---

We claim:

1. A method of treating cancer, wherein the cancer has been determined to comprise CYP3A5-positive cancer cells, wherein a tumor cell is positive for CYP3A5, when expression of CYP3A5 in said tumor cell is at least two-fold higher than in non-cancerous cells from the same tissue or cells of the same type, wherein the cancer is exocrine-like subtype PDAC cancer, comprising administering to a patient having said cancer a drug combination of (i) a specific inhibitor of cytochrome P450 3A5 (CYP3A5) and (ii) one or more additional chemotherapeutic agents.

2. The method of claim 1, wherein the drug combination comprises (i) at least one Src inhibitor selected from bosutinib, dasatinib, ponatinib and saracatinib, (ii) at least one EGF receptor inhibitor selected from erlotinib, gefitinib, afatinib, vandetanib, lapatinib, AZD9291, neratinib, pelitinib, dacomitinib, canertinib, icotinib, and varlitinib; (iii) irinotecan; and/or (iv) a taxane.

3. The method of claim 1, wherein the specific inhibitor of cytochrome P450 3A5 (CYP3A5) is an siRNA molecule or an shRNA molecule.

4. The method of claim 1, wherein said patient currently is, or has already been, under treatment of cancer with a therapeutically active substance.

5. The method of claim 1, wherein the one or more additional chemotherapeutic agents are selected from (i) a tyrosine kinase inhibitor, (ii) gemcitabine, (iii) irinotecan; and (iv) a taxane.

6. The method of claim 5, wherein the tyrosine kinase inhibitor is a Src inhibitor and/or an EGF receptor inhibitor.

7. The method of claim 6, wherein the Src inhibitor is selected from bosutinib, dasatinib, ponatinib and saracatinib.

8. The method of claim 7, wherein the Src inhibitor is dasatinib.

9. The method of claim 6, wherein the EGF receptor inhibitor is selected from erlotinib, gefitinib, afatinib, vandetanib, lapatinib, AZD9291, neratinib, pelitinib, dacomitinib, canertinib, icotinib, and varlitinib.

10. The method of claim 9, wherein the EGF receptor inhibitor is erlotinib.

11. The method of claim 5, wherein the taxane is selected from paclitaxel and docetaxel.

12. The method of claim 2, wherein the at least one Src inhibitor is dasatinib.

13. The method of claim 2, wherein the at least one EGF receptor inhibitor is erlotinib.

14. The method of claim 2, wherein the taxane is selected from paclitaxel and docetaxel.

15. The method of claim 2, wherein the drug combination comprises two compounds selected from (i) to (iv).

16. The method of claim 15, wherein the two compounds are irinotecan and paclitaxel.

17. The method of claim 4, wherein said cancer is recurring, refractory, and/or resistant to said therapeutically active substance.

\* \* \* \* \*

SEQUENCE LISTING

```
<160> NUMBER OF SEQ ID NOS: 10

<210> SEQ ID NO 1
<211> LENGTH: 19
<212> TYPE: RNA
<213> ORGANISM: Artificial sequence
<220> FEATURE:
<223> OTHER INFORMATION: artificial siRNA sequence

<400> SEQUENCE: 1
ccuugaaauu agacacgca                                                   19

<210> SEQ ID NO 2
<211> LENGTH: 19
<212> TYPE: RNA
<213> ORGANISM: Artificial sequence
<220> FEATURE:
<223> OTHER INFORMATION: artificial siRNA sequence

<400> SEQUENCE: 2
cgugaucaga acagugcua                                                   19

<210> SEQ ID NO 3
<211> LENGTH: 19
<212> TYPE: RNA
<213> ORGANISM: Artificial sequence
<220> FEATURE:
<223> OTHER INFORMATION: artificial siRNA sequence

<400> SEQUENCE: 3
ggucaauggu ggugauucc                                                   19

<210> SEQ ID NO 4
<211> LENGTH: 19
<212> TYPE: RNA
<213> ORGANISM: Artificial sequence
<220> FEATURE:
<223> OTHER INFORMATION: artificial siRNA sequence

<400> SEQUENCE: 4
cuauuagacu ugagaggac                                                   19

<210> SEQ ID NO 5
<211> LENGTH: 19
<212> TYPE: RNA
<213> ORGANISM: Artificial sequence
<220> FEATURE:
<223> OTHER INFORMATION: artificial siRNA sequence
```

```
<400> SEQUENCE: 5
ugguuuacau gucgacuaa                                          19

<210> SEQ ID NO 6
<211> LENGTH: 19
<212> TYPE: RNA
<213> ORGANISM: Artificial sequence
<220> FEATURE:
<223> OTHER INFORMATION: artificial siRNA sequence

<400> SEQUENCE: 6
ugguuuacau guuguguga                                          19

<210> SEQ ID NO 7
<211> LENGTH: 19
<212> TYPE: RNA
<213> ORGANISM: Artificial sequence
<220> FEATURE:
<223> OTHER INFORMATION: artificial siRNA sequence

<400> SEQUENCE: 7
ugguuuacau guuuucuga                                          19

<210> SEQ ID NO 8
<211> LENGTH: 19
<212> TYPE: RNA
<213> ORGANISM: Artificial sequence
<220> FEATURE:
<223> OTHER INFORMATION: artificial siRNA sequence

<400> SEQUENCE: 8
ugguuuacau guuuuccua                                          19

<210> SEQ ID NO 9
<211> LENGTH: 19
<212> TYPE: DNA
<213> ORGANISM: Artificial sequence
<220> FEATURE:
<223> OTHER INFORMATION: artificial antisense shRNA sequence

<400> SEQUENCE: 9
ttgatttcaa catctttct                                          19

<210> SEQ ID NO 10
<211> LENGTH: 19
<212> TYPE: DNA
<213> ORGANISM: Artificial sequence
<220> FEATURE:
<223> OTHER INFORMATION: artificial antisense shRNA sequence

<400> SEQUENCE: 10
tgactaagtt gaaatctct                                          19
```